(12) United States Patent
Strugnell et al.

(10) Patent No.: US 10,584,148 B2
(45) Date of Patent: Mar. 10, 2020

(54) ENGINEERED INFLUENZA ANTIGENIC POLYPEPTIDES AND IMMUNOGENIC COMPOSITIONS THEREOF

(71) Applicant: SANOFI PASTEUR INC., Swiftwater, PA (US)

(72) Inventors: Tod Strugnell, Cambridge, MA (US); Eliud Oloo, Cambridge, MA (US); Raymond Oomen, Cambridge, MA (US)

(73) Assignee: SANOFI PASTEUR INC., Swiftwater, PA (US)

( * ) Notice: Subject to any disclaimer, the term of this patent is extended or adjusted under 35 U.S.C. 154(b) by 0 days.

(21) Appl. No.: 15/578,880

(22) PCT Filed: Jun. 2, 2016

(86) PCT No.: PCT/US2016/035594
§ 371 (c)(1),
(2) Date: Dec. 1, 2017

(87) PCT Pub. No.: WO2016/196846
PCT Pub. Date: Dec. 8, 2016

(65) Prior Publication Data
US 2018/0298063 A1    Oct. 18, 2018

Related U.S. Application Data

(60) Provisional application No. 62/344,862, filed on Jun. 2, 2016, provisional application No. 62/169,814, filed on Jun. 2, 2015.

(51) Int. Cl.
| | |
|---|---|
| *A61K 39/145* | (2006.01) |
| *A61K 39/00* | (2006.01) |
| *A61K 39/12* | (2006.01) |
| *A61K 39/42* | (2006.01) |
| *C07K 14/11* | (2006.01) |
| *C07K 14/005* | (2006.01) |
| *A61K 9/00* | (2006.01) |
| *A61K 39/39* | (2006.01) |
| *C12N 9/24* | (2006.01) |

(52) U.S. Cl.
CPC .......... *C07K 14/005* (2013.01); *A61K 9/0019* (2013.01); *A61K 9/0053* (2013.01); *A61K 39/145* (2013.01); *A61K 39/39* (2013.01); *C12N 9/2402* (2013.01); *C12Y 302/01018* (2013.01); *A61K 2039/5258* (2013.01); *A61K 2039/54* (2013.01); *C07K 2319/00* (2013.01); *C12N 2760/16022* (2013.01); *C12N 2760/16023* (2013.01); *C12N 2760/16034* (2013.01); *C12N 2760/16052* (2013.01); *C12N 2760/16062* (2013.01); *C12N 2760/16071* (2013.01); *C12N 2760/16122* (2013.01); *C12N 2760/16123* (2013.01); *C12N 2760/16134* (2013.01); *C12N 2760/16152* (2013.01); *C12N 2760/16162* (2013.01); *C12N 2760/16171* (2013.01); *C12N 2760/16222* (2013.01); *C12N 2760/16223* (2013.01); *C12N 2760/16234* (2013.01); *C12N 2760/16252* (2013.01); *C12N 2760/16262* (2013.01); *C12N 2760/16271* (2013.01)

(58) Field of Classification Search
CPC .................. A61K 39/145; A61K 39/12; C12N 2760/16134; C12N 2760/16122; C07K 14/005
See application file for complete search history.

(56) References Cited

FOREIGN PATENT DOCUMENTS

| | | | |
|---|---|---|---|
| WO | 2008094200 | A2 | 8/2008 |
| WO | 2009026397 | A2 | 2/2009 |
| WO | WO2009026397 | * | 2/2009 |
| WO | 2009076778 | A1 | 6/2009 |
| WO | WO2009026397 | * | 12/2009 |
| WO | 2010003225 | A1 | 1/2010 |
| WO | 2013044203 | A2 | 3/2013 |
| WO | 2013119683 | A1 | 8/2013 |
| WO | 2013148164 | A1 | 10/2013 |
| WO | WO2013148164 | * | 10/2013 |

(Continued)

OTHER PUBLICATIONS

Carter, Donald M. et al., "Design and Characterization of a Computationally Optimized Broadly Reactive Hemagglutinin Vaccine for H1N1 Influenza Viruses", Journal of Virology (Online), American Society for Microbiology, US, 90(9): 4720-4734 (2016).

(Continued)

*Primary Examiner* — Barry A Chestnut
(74) *Attorney, Agent, or Firm* — Proskauer Rose LLP; Fangli Chen

(57) ABSTRACT

The present invention provides, among other things, a novel and improved method for generating "mosaic" influenza antigenic polypeptides including hemagglutinin (HA) and neuraminidase (NA) polypeptides based on unique combination of epitope patterns that maximize exposure to epitopes present across multiple HA or NA sequences and therefore improved influenza strain coverage. In particular, the present invention provides engineered H1N1 influenza hemagglutinin (HA) polypeptides that are comprised of novel combinations of protective epitopes and antigenic regions from multiple H1N1 viral strains. Such engineered HA polypeptides have improved properties over HA polypeptides developed through conventional approaches that rely on consensus alignments of viral sequences.

28 Claims, 21 Drawing Sheets

Specification includes a Sequence Listing.

(56) References Cited

FOREIGN PATENT DOCUMENTS

WO     2015184272 A2     3/2015
WO     2016100926 A1     6/2016

OTHER PUBLICATIONS

Kleanthous, Harry; Sanofi Pasteur, "Re-eingeneering HA as a strategy to develop universal influenza vaccines", (2013), URL: http://apps.who.int/vaccine_research/meetings/Harold_Kleanthous.pdf.

* cited by examiner

Figure 1

|  | MSA |  | MSA epitopes |
|---|---|---|---|
| A/Novosibirsk/151/2009 | ILGNSECELLISKESWSYIVEK | A/Novosibirsk/151/2009 | LISKES |
| A/Melbourne/1/1946 | ILGNPECDSLLPASSWSYIVET | A/Melbourne/1/1946 | LLPASS |
| A/FortWorth/1950 | VLGNPECESLLSNRSWSYIAET | A/FortWorth/1950 | LLSNRS |
| A/PuertoRico/8/1934 | LLGNPECDPLLPVRSWSYIVET | A/PuertoRico/8/1934 | LLPVRS |
| A/Melbourne/1935 | LLGNPECDSLLPASSWSYIVET | A/Melbourne/1935 | LLPASS |
| A/Novosibirsk/4/2009 | ILGNPECELLVSKESWSYIVEK | A/Novosibirsk/4/2009 | LVSKES |
| A/Denver/1957 | VLGNPECESLLSNRSWSYIAET | A/Denver/1957 | LLSNRS |
| A/Henry/1936 | LLGNPECDPLLPARSWSYIVET | A/Henry/1936 | LLPARS |
| A/UnitedKingdom/1/1933 | LLGNPECDSLLPARSWSYIVET | A/UnitedKingdom/1/1933 | LLPARS |
| A/PuertoRico/8/1934 | LLGNPECDPLLPVRSWSYIVET → | A/PuertoRico/8/1934 | LLPVRS |
| A/Mongolia/153/88 | LLGNPECDPLLPVRSWSYIVET | A/Mongolia/153/88 | LLPVRS |
| A/PuertoRico/8/1934 | LLGNPECDPLLPVRSWSYIVET | A/PuertoRico/8/1934 | LLPVRS |
| A/Tokyo/3/1967 | LLGNPECDSLLPARSWSYIVET | A/Tokyo/3/1967 | LLPARS |
| A/Wilson-Smith/1933 | LLGNPECDSLLPARSWSYIVET | A/Wilson-Smith/1933 | LLPARS |
| A/NewJersey/11/1976 | LLGNPECELLLTVSSWSYIVET | A/NewJersey/11/1976 | LLTVSS |
| A/NewJersey/1976 | LLGNPECELLLTVSSWSYIVET | A/NewJersey/1976 | LLTVSS |
| A/Maryland/12/1991 | LLGNPECELLFTASSWSYIVET | A/Maryland/12/1991 | LFTASS |
| A/Ohio/3559/1988 | LLGNPECELLFTASSWSYIVET | A/Ohio/3559/1988 | LFTASS |
| A/Wisconsin/4755/1994 | LLGNPECELLFTASSWSYIVET | A/Wisconsin/4755/1994 | LFTASS |
| A/Ohio/01/2007 | LLGNPECESLSTASSWSYIVET | A/Ohio/01/2007 | LSTASS |
| A/Wisconsin/301/1976 | LLGNPECELLFTVSSWSYIVET | A/Wisconsin/301/1976 | LFTVSS |

Unique epitope sets

LISKES
LLPASS
LLSNRS
LLPVRS
LVSKES
LLPARS
LLTVSS
LFTASS
LSTASS
LFTVSS

⇒

Epitope cassettes

| LISKES | LLPVRS | LLTVSS |
| LLPASS | LVSKES | LFTASS |
| LLSNRS | LLPARS | LSTASS |
| LLPVRS | LLTVSS | LFTVSS |
| LVSKES | LFTASS | LLPVRS |
| ... | ... | ... |

✚

Other epitope cassettes

⇩

>mosaic_AF4362_1 Ca12009:VNNKESSNEPG   Ca22009:SHARKSRN   138194:LLPARSWS ...
...LLPARSWS.......................................EIFP ...SWPN.ETN.......SHARKS...
>mosaic_AF4362_2 Ca12009:INDKGTSREPG   Ca22009:PHAGAKRD   138194:LSTASSWS ...
...LSTASSWS.......................................EIFP ...SWPN.TVT.......PHAGAK...

⇩

>mosaic_AF4362_1 Ca12009:VNNKESSNEPG   Ca22009:SHARKSRN   138194:LLPARSWS ...
...LLPARSWSYIVETPNPENGTCYPGYFADYEELREQLSSVSSFERFEIFPKESSWPNHETNGVSASCSHARKS...
>mosaic_AF4362_2 Ca12009:INDKGTSREPG   Ca22009:PHAGAKRD   138194:LSTASSWS ...
...LSTASSWSYIVETPNPENGTCYPGYFADYEELREQLSSVSSFERFEIFPKESSWPNHTVTGVSASCPHAGAK...

Figure 8

ENGINEERED INFLUENZA ANTIGENIC POLYPEPTIDES AND IMMUNOGENIC COMPOSITIONS THEREOF

CROSS REFERENCE TO RELATED APPLICATIONS

This application is a 35 U.S.C. § 371 National Stage Application of International Application No. PCT/US16/35594, filed Jun. 2, 2016, which claims priority to United States Provisional Patent Application Ser. Nos. 62/169,814 filed Jun. 2, 2015; the entirety of which is hereby incorporated by reference. This application relates to U.S. provisional application 62/344,862 filed on Jun. 2, 2016; the entirety of which is hereby incorporated by reference.

INCORPORATION-BY-REFERENCE OF SEQUENCE LISTING

The content of the text file named "SPR-004US_ST25.txt", which was created on Nov. 30, 2017 and is 103 KB in size, hereby incorporated by reference in its entirety.

BACKGROUND

Influenza has a long standing history of pandemics, epidemics, resurgences and outbreaks. Vaccines have been the most effective defense against influenza. However, the effort to design and manufacture vaccines that induce strain-specific immunity year-over-year has been difficult and influenza continues to cause significant health problems across the globe. Indeed, currently marketed influenza vaccines must be updated annually based on predicted strains that will be present in human populations in the impending season.

Current influenza vaccines are based on inducing immunity to the hemagglutinin antigen present on the surface of influenza viruses. Hemagglutinin (HA) is a glycoprotein responsible for the binding of the influenza virus to cells with sialic acid-containing on surface structures on their membranes, and is highly variable across influenza virus strains. Among the current strategies for vaccination against influenza, the development of a universal vaccine holds the promise to increase the breadth of current strain-specific vaccines by focusing on relatively conserved regions of HA.

SUMMARY

The present invention provides, among other things, a novel and improved method for generating "mosaic" influenza antigenic polypeptides including hemagglutinin (HA) and neuraminidase (NA) polypeptides based on unique combination of epitope patterns that maximize exposure to epitopes present across multiple HA or NA sequences and therefore improved influenza strain coverage. In particular, the present invention provides engineered influenza A hemagglutinin (HA) polypeptides that provide for improved protective immunity (e.g., a broad reactive immune response) to multiple influenza A virus isolates. The engineered HA polypeptides were developed by using a unique combination of epitope patterns to create "mosaic" HA polypeptides that maximize exposure to epitopes present across multiple HA sequences and therefore improved influenza strain coverage.

In one aspect, the present invention provides a method of engineering a mosaic influenza hemagglutinin (HA) polypeptide, comprising obtaining HA amino acid sequences from multiple circulating strains of a particular type and/or subtype of influenza virus; aligning the HA amino acid sequences to generate an alignment; identifying the positions of amino acids comprising known epitopes and antigenic regions; compiling the amino acid residues across the alignment at the identified positions for each epitope and antigenic region; defining a set of amino acid sequence patterns within the compiled sequences for each epitope and antigenic region, wherein each amino acid sequence pattern in the set is represented only once; selecting a sequence from the set for each epitope or antigenic region; and inserting selected sequences into corresponding locations in a structural backbone of HA to generate a mosaic influenza HA polypeptide.

As used herein, "corresponding locations", in the context of an influenza HA or NA polypeptide sequence, generally refer to the locations that correspond to the location of the known epitopes and antigenic regions. Typically, "corresponding locations" in a polypeptide of interest (e.g., an HA polypeptide) are designated using a canonical numbering system based on a reference related polypeptide. Residues at "corresponding locations" of different HA or NA polypeptides need not actually be at the same locations.

In another aspect, the present invention provides a method of engineering a mosaic influenza hemagglutinin (HA) polypeptide, comprising obtaining HA amino acid sequences from multiple circulating strains of a particular type and/or subtype of influenza virus; aligning the HA amino acid sequences to generate an alignment; identifying the positions of amino acids comprising known epitopes and antigenic regions across the alignment; compiling the amino acid residues at the identified positions for each epitope and antigenic region; defining a set amino acid sequence patterns within the compiled sequences for each epitope and antigenic region, wherein each amino sequence pattern in the set is represented only once; generating a consensus sequence from each set for each epitope or antigenic region; and inserting the consensus sequences into corresponding locations in a structural backbone of HA to generate a mosaic influenza HA polypeptide.

In some embodiments, the methods described herein may be performed computationally. In particular embodiments, the methods may be performed using an algorithm.

In some embodiments, the locations in the structural model do not overlap.

In some embodiments, the steps of various methods according to the present invention are performed in silico by a suitably programmed computer system.

In some embodiments, a method of the present invention further comprises measuring the stability of the mosaic influenza HA polypeptide.

In some embodiments, measuring the stability comprises calculating the folding energy of each mosaic influenza HA polypeptide and selecting polypeptides that are likely to fold into a native-like conformation.

In some embodiments, the selecting step used in a method of the present invention further comprises ranking the selected sequences by sequence identity, geographical location and/or isolation date of the type or subtype of influenza virus. In some embodiments, the selecting step is random. In some embodiments, the sequences are selected so the mosaic influenza HA polypeptide elicits a broadly neutralizing immune response against multiple circulating influenza strains.

In some embodiments, prior to the selecting step, the patterns in the set are weighted by their frequency of occurrence. In some embodiments, the selecting step comprises selecting the most frequently occurring sequence for each of the epitopes or antigenic regions. In some embodiments, the selecting step comprises selecting the second most frequently occurring sequence for each of the epitopes or antigenic regions. In some embodiments, the selecting step comprises selecting the third most frequently occurring sequence for each of the epitopes or antigenic regions.

In some embodiments, the obtaining step further comprises identifying redundant sequences by screening the HA amino acid sequences for those with 100%, or greater than 99.9%, 99% 98%, 97%, or 96% sequence identity, and removing all but one of the redundant sequences.

In some embodiments, the obtaining step according to a method of the present invention further comprises identifying and removing redundant sequences.

In some embodiments, the obtaining step comprises obtaining 100-5000 HA amino acid sequences from multiple circulating influenza strains.

In some embodiments, the obtaining step comprises obtaining all publicly available HA amino acid sequences.

In some embodiments, a method according to the present invention further comprises: generating a nucleic acid sequence corresponding to the mosaic influenza HA polypeptide; cloning the nucleic acid sequence into a mammalian expression vector; and transfecting a mammalian host cell with the mammalian expression vector. In some embodiments, the mammalian host cell is a vero cell.

In some embodiments, the epitopes are neutralizing epitopes. In some embodiments, the epitopes are discontinuous epitopes. In some embodiments, the epitopes are continuous epitopes. In some embodiments, the epitopes are B cell epitopes.

In some embodiments, a method according to the present invention involves obtaining HA amino acid sequences from multiple circulating strains of a particular type and/or subtype of influenza virus which is a type A influenza virus. In some embodiments, the influenza A virus is selected from subtypes H1, H2, H3, H4, H5, H6, H7, H8, H9, H10, H11, H12, H13, H14, H15, or H16. In some embodiments, the influenza virus is elected from the group consisting of H1N1, H3N2, H5N1, and H7N9. In some embodiments, the type A virus is a seasonal strain. In particular embodiments, a method according to the present invention involves obtaining HA amino acid sequences from multiple circulating strains including/Texas/36/1991, A/Singapore/1986, A/New Caledonia/20/1999, A/Solomon Islands/03/2006, and A/Brisbane/59/2007 and A/Wisconsin/67/2005. In some embodiments, the type A virus is a pandemic strain. In some embodiments, a method according to the present invention involves obtaining HA amino acid sequences from multiple circulating strains including A/California/07/2009, A/California/04/2009, A/Belgium/145/2009, A/South Carolina/01/1918 and A/New Jersey/1976.

In some embodiments, a method according to the present invention involves obtaining HA amino acid sequences from multiple circulating strains of a particular type and/or subtype of influenza virus is a type B influenza virus. In some embodiments, the influenza B virus is a Yamagata lineage strain. In some embodiments, the influenza B virus is a Victoria lineage strain. In some embodiments, the influenza B virus strain circulated prior to the split into distinct lineages and is therefore neither a Yamagata nor Victoria lineage. In some embodiments, a method according to the present invention involves obtaining HA amino acid sequences from the influenza B virus selected from B/Hong Kong/330/2001, B/Hong Kong/05/1972, B/Lee/40, B/Massachusetts/02/2012, B/Panama/45/1990, B/Singapore/222/79, B/Victoria/02/1987, B/Yamagata/16/1988, or B/Brisbane/60/2008.

In yet another aspect, the present invention provides a method of engineering a mosaic influenza neuraminidase (NA) polypeptide, comprising: obtaining NA amino acid sequences from multiple circulating strains of a particular type and/or subtype of influenza virus; aligning the NA amino acid sequences to generate an alignment; identifying the positions of amino acids comprising known epitopes and antigenic regions; compiling the amino acid residues across the alignment at the identified positions for each epitope and antigenic region; defining a set of amino acid sequence patterns within the compiled sequences for each epitope and antigenic region, wherein each amino sequence pattern in the set is represented only once; selecting a sequence from the set for each epitope or antigenic region; and inserting selected sequences into corresponding locations in a structural backbone of NA to generate a mosaic influenza NA polypeptide.

In still another aspect, the present invention provides a method of engineering a mosaic influenza neuraminidase (NA) polypeptide, comprising: obtaining NA amino acid sequences from multiple circulating strains of a particular type and/or subtype of influenza virus; aligning the NA amino acid sequences to generate an alignment; identifying the positions of amino acids comprising known epitopes and antigenic regions across the alignment; compiling the amino acid residues at the identified positions for each epitope and antigenic region; defining a set amino acid sequence patterns within the compiled sequences for each epitope and antigenic region, wherein each amino sequence pattern in the set is represented only once; generating a consensus sequence from each set for each epitope or antigenic region; and inserting the consensus sequences into corresponding locations in a structural backbone of NA to generate a mosaic influenza NA polypeptide.

In some embodiments, the locations in the structural model do not overlap.

In some embodiments, the steps according to various methods described herein are performed in silico by a suitably programmed computer system.

In some embodiments, a method according to the present invention further comprises measuring the stability of the mosaic influenza NA polypeptide. In some embodiments, measuring the stability comprises calculating the folding energy of each mosaic influenza NA polypeptide and selecting polypeptides that are likely to fold into a native-like conformation.

In some embodiments, the selecting step further comprises ranking the selected sequences by sequence identity, geographical location and/or isolation date of the type or subtype of influenza virus. In some embodiments, the selecting step is random. In some embodiments, the sequences are selected so the mosaic influenza NA polypeptide elicits a broadly neutralizing immune response against the multiple circulating influenza strains.

In some embodiments, prior to the selecting step, the patterns in the set are weighted by their frequency of occurrence. In some embodiments, the selecting step comprises selecting the most frequently occurring sequence for each of the epitopes or antigenic regions. In some embodiments, the selecting step comprises selecting the second most frequently occurring sequence for each of the epitopes or antigenic regions. In some embodiments, the selecting step comprises selecting the third most frequently occurring sequence for each of the epitopes or antigenic regions.

In some embodiments, the obtaining step according to a method of the present invention further comprises identifying redundant sequences by screening the NA amino acid sequences for those with 100%, or greater than 99.9%, 99% 98%, 97%, or 96% sequence identity, and removing all but one of the redundant sequences.

In some embodiments, the obtaining step according to a method of the present invention further comprises identifying and removing redundant sequences.

In some embodiments, the obtaining step comprises obtaining 100-5000 NA amino acid sequences from multiple circulating influenza strains.

In some embodiments, the obtaining step comprises obtaining all publicly available NA amino acid sequences.

In some embodiments, a method of the present invention further comprises generating a nucleic acid sequence corresponding to the mosaic influenza HA polypeptide; cloning the nucleic acid sequence into a mammalian expression vector; and transfecting a mammalian host cell with the mammalian expression vector. In some embodiments, the mammalian host cell is a vero cell.

In some embodiments, the epitopes are neutralizing epitopes. In some embodiments, the epitopes are discontinuous epitopes.

Among other things, the present invention provides an engineered mosaic influenza HA or NA polypeptide according to various methods described here in, or a combination thereof.

In some embodiments, the present invention provides an engineered influenza hemagglutinin (HA) polypeptide comprising an amino acid sequence that is at least 90% (e.g., at least 91%, 92%, 93%, 94,%, 95%, 96%, 97%, 98% or 99%) identical to an engineered influenza HA polypeptide that appears in Table 1 (e.g., SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, or SEQ ID NO:10).

In some embodiments, the present invention provides an engineered influenza HA polypeptide comprising an amino acid sequence that is substantially identical to an engineered influenza HA polypeptide that appears in Table 1.

In some embodiments, the present invention provides an engineered influenza HA polypeptide comprising an amino acid sequence that is identical to an engineered influenza HA polypeptide that appears in Table 1.

In some embodiments, the present invention provides an engineered influenza HA polypeptide comprising an amino acid sequence selected from SEQ ID NO: 1, SEQ ID NO:2, SEQ ID NO:3, SEQ ID NO:4, SEQ ID NO:5, SEQ ID NO:6, SEQ ID NO:7, SEQ ID NO:8, SEQ ID NO:9 and SEQ ID NO:10.

In some embodiments, the present invention provides an engineered influenza HA polypeptide comprising an antigenic region that is associated with, adjacent to and/or encompasses a receptor binding site, wherein the antigenic region comprises an amino acid sequence, or subset thereof, that is at least 90% (e.g., at least 91%, 92%, 93%, 94,%, 95%, 96%, 97%, 98% or 99%) identical to an antigenic region sequence, or subset thereof, that appears in Table 2.

In some embodiments, the present invention provides an engineered influenza HA polypeptide comprising an antigenic region that is associated with, adjacent to and/or encompasses a receptor binding site, wherein the antigenic region comprises an amino acid sequence, or subset thereof, that is substantially identical to an antigenic region sequence, or subset thereof, that appears in Table 2.

In some embodiments, the present invention provides an engineered influenza HA polypeptide comprising an antigenic region that is associated with, adjacent to and/or encompasses a receptor binding site, wherein the antigenic region comprises an amino acid sequence, or subset thereof, that is identical to an antigenic region sequence, or subset thereof, that appears in Table 2.

In some embodiments, the present invention provides an engineered influenza HA polypeptide comprising an antigenic region that is associated with, adjacent to and/or encompasses a receptor binding site, wherein the antigenic region comprises an amino acid sequence, or subset thereof, selected from SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38 and SEQ ID NO:39.

In some certain embodiments, the present invention provides an engineered influenza HA polypeptide comprising an antigenic region that is associated with, adjacent to and/or encompasses a receptor binding site, wherein the antigenic region comprises an amino acid sequence, or subset thereof, wherein the engineered HA polypeptide comprises a backbone HA sequence derived from a pre-pandemic, pandemic, or consensus HA sequence. In some embodiments, backbone sequences are derived from an A/New Caledonia/20/99 influenza sequence, A/California/07/2009, or HA consensus sequence spanning viral isolates 1918-2011.

In some embodiments, the present invention provides an isolated nucleic acid molecule encoding an engineered HA polypeptide as described herein. In some certain embodiments, an isolated nucleic acid sequence encoding an engineered HA polypeptide as described herein is codon-optimized for expression in mammalian cells, microalgae, plants, yeast, fungi or bacteria.

In related aspects, the present invention provides an isolated nucleic acid molecule encoding an engineered mosaic HA polypeptide according to various methods described herein.

In some embodiments, the present invention provides a vector comprising a nucleic acid molecule encoding an engineered mosaic HA polypeptide as described herein.

In some embodiments, the present invention provides an isolated cell comprising a vector as described herein. In some embodiments, the isolated cell is a mammalian cell. In some embodiments, the isolated cell is a human cell.

In some embodiments, the present invention provides a fusion protein comprising an influenza HA polypeptide as described herein.

In some embodiments, the present invention provides an influenza virus-like particle (VLP) comprising an influenza HA polypeptide as described herein. In some certain embodiments, an influenza VLP of the present invention further comprises an influenza neuraminidase (NA) protein, a human immunodeficiency virus (HIV) gag protein, or both.

In some embodiments, the present invention provides a pharmaceutical composition comprising an influenza HA polypeptide, a fusion protein, or an influenza VLP as described herein.

In some embodiments, the present invention provides a method for producing an influenza VLP comprising an influenza HA polypeptide as described herein, the method comprising transfecting a host cell with (i) a vector encoding the influenza HA polypeptide, (ii) a vector encoding an influenza NA protein, and (iii) a vector encoding a viral structural protein (e.g., an influenza M1 protein, an HIVgag protein, etc.) under conditions sufficient to allow for expression of the HA, NA and viral structural proteins. In some certain embodiments, the viral structural protein is an HIV-gag protein. In some certain embodiments, the host cell is a human cell.

In further aspects, the present invention provides a vaccine composition comprising an engineered mosaic HA polypeptide or a fusion protein thereof described herein. In some embodiments, the vaccine composition is a split inactivated virus.

In further aspects, the vaccine composition comprises a VLP.

In some embodiments, the present invention provides a method of immunizing a subject against influenza virus, the method comprising administering to the subject a pharmaceutical composition as described herein. In some embodiments, the pharmaceutical composition further comprises an adjuvant.

In some embodiments, the present invention provides a method of inducing an immune response in a subject, the method comprising administering to the subject an influenza HA polypeptide, a fusion protein or an influenza VLP as described herein. In some embodiments, a method of the present invention further comprises administering an adjuvant.

In some embodiments, a pharmaceutical composition, an influenza HA polypeptide, a fusion protein or an influenza VLP as described herein, is administered intramuscularly, intranasally, intradermally, subcutaneously, orally, or intravenously.

In still other aspects, the present invention provides a method of immunizing a subject against influenza virus, comprising administering to the subject a vaccine composition comprising an engineered mosaic HA polypeptide or a fusion protein thereof. In some embodiments, the pharmaceutical composition further comprises an adjuvant. In some embodiments, a pharmaceutical composition, an influenza HA polypeptide, a fusion protein or an influenza VLP or split inactivated virus thereof as described herein, is administered intramuscularly, intranasally, intradermally, subcutaneously, orally, or intravenously.

It is to be understood that both the foregoing general description and the following detailed description are exemplary and explanatory only and are not restrictive of the invention, as claimed.

BRIEF DESCRIPTION OF THE DRAWING

The Drawing included herein, which is comprised of the following Figures, is for illustration purposes only not for limitation.

FIG. 1 shows a general illustration of the approach for designing engineered hemagglutinin (HA) polypeptides via structural mapping of antigenic repertoires. Mosaic antigen designs are constructed into a single HA molecule based on combinations of epitope patterns observed in HA sequences from circulating strains. Engineered HA molecules as described herein contain repertoires of neutralizing epitopes and antigenic sites or surface regions, which are computationally assembled from diverse strains and carefully selected to collectively, elicit broadly neutralizing antibodies in a host.

FIG. 8 shows an exemplary detailed sequence overview of the mosaic approach.

Figure 2:
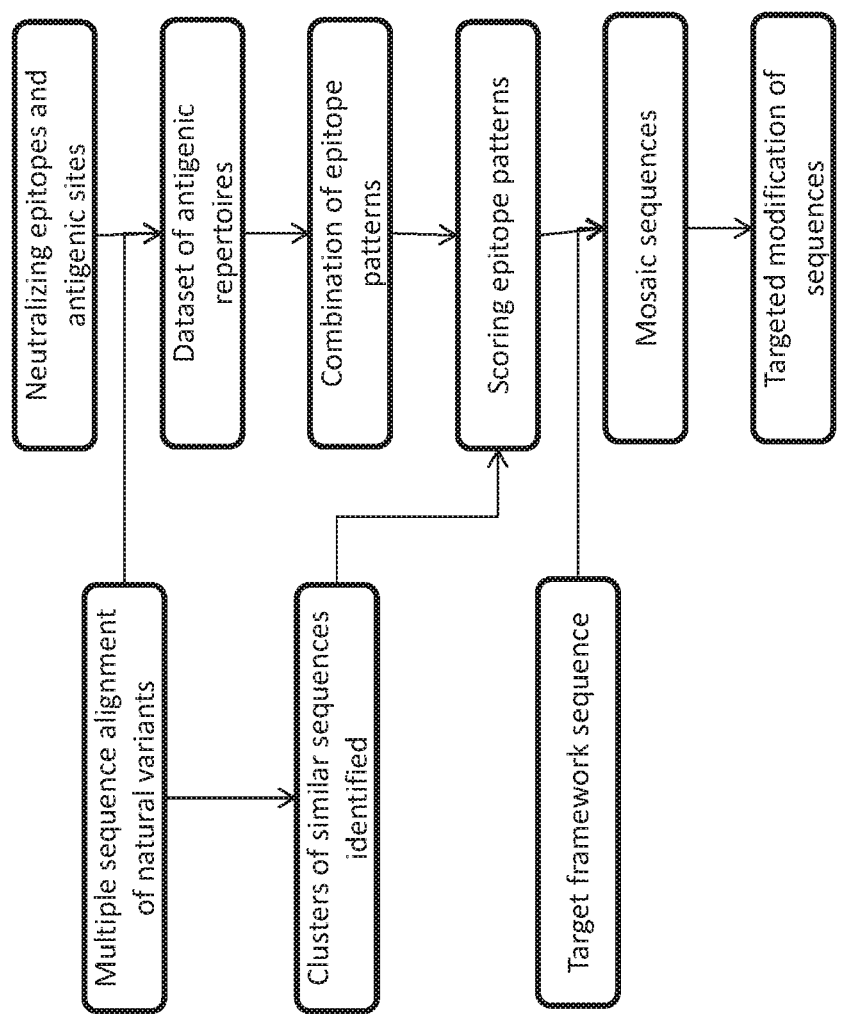
FIG. 2 shows an exemplary flowchart for the design and production of engineered HA polypeptides using structural mapping of antigenic repertoires. Antigenic repertoires of multiple epitopes were identified and organized into alignment coverage optimized repertoire subsets. Mosaic sequences were generated through combination of different epitopes. Mosaic combinations of epitopes were evaluated for alignment coverage based on geographic regions, viral isolate years, viral sub-family clusters or other measures to identify high scoring designs. Generated mosaic sequences were optimized by structural refinement and could be further refined through targeted sequence modifications.

Antigen: As used herein, the term "antigen", refers to an agent that elicits an immune response; and/or (ii) an agent that is bound by a T cell receptor (e.g., when presented by an MHC molecule) or to an antibody (e.g., produced by a B cell) when exposed or administered to an organism. In some embodiments, an antigen elicits a humoral response (e.g., including production of antigen-specific antibodies) in an organism; alternatively or additionally, in some embodiments, an antigen elicits a cellular response (e.g., involving T-cells whose receptors specifically interact with the antigen) in an organism. It will be appreciated by those skilled in the art that a particular antigen may elicit an immune response in one or several members of a target organism (e.g., mice, rabbits, primates, humans), but not in all members of the target organism species. In some embodiments, an antigen elicits an immune response in at least about 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99% of the members of a target organism species. In some embodiments, an antigen binds to an antibody and/or T cell receptor, and may or may not induce a particular physiological response in an organism. In some embodiments, for example, an antigen may bind to an antibody and/or to a T cell receptor in vitro, whether or not such an interaction occurs in vivo. In some embodiments, an antigen reacts with the products of specific humoral or cellular immunity, including those induced by heterologous immunogens. In some embodiments of the disclosed compositions and methods, influenza HA protein is an antigen.

Approximately: As used herein, the term "approximately" or "about," as applied to one or more values of interest, refers to a value that is similar to a stated reference value. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

Associated with: Two events or entities are "associated" with one another, as that term is used herein, if the presence, level and/or form of one is correlated with that of the other. For example, a particular entity (e.g., polypeptide) is considered to be associated with a particular disease, disorder, or condition, if its presence, level and/or form correlates with incidence of and/or susceptibility of the disease, disorder, or condition (e.g., across a relevant population). In some embodiments, two or more entities are physically "associated" with one another if they interact, directly or indirectly, so that they are and remain in physical proximity with one another. In some embodiments, two or more entities that are physically associated with one another are covalently linked to one another; in some embodiments, two or more entities that are physically associated with one another are not covalently linked to one another but are non-covalently associated, for example by means of hydrogen bonds, van der Waals interaction, hydrophobic interactions, magnetism, and combinations thereof.

Binding: It will be understood that the term "binding", as used herein, typically refers to a non-covalent association between or among two or more entities. "Direct" binding involves physical contact between entities or moieties; indirect binding involves physical interaction by way of physical contact with one or more intermediate entities. Binding between two or more entities can be assessed in any of a variety of contexts—including where interacting entities or moieties are studied in isolation or in the context of more complex systems (e.g., while covalently or otherwise associated with a carrier entity and/or in a biological system or cell).

Carrier: As used herein, the term "carrier" refers to a diluent, adjuvant, excipient, or vehicle with which a composition is administered. In some exemplary embodiments, carriers can include sterile liquids, such as, for example, water and oils, including oils of petroleum, animal, vegetable or synthetic origin, such as, for example, peanut oil, soybean oil, mineral oil, sesame oil and the like. In some embodiments, carriers are or include one or more solid components.

Characteristic Portion: As used herein, the term "characteristic portion" is used, in the broadest sense, to refer to a portion of a substance whose presence (or absence) correlates with presence (or absence) of a particular feature, attribute, or activity of the substance. In some embodiments, a characteristic portion of a substance is a portion that is found in the substance and in related substances that share the particular feature, attribute or activity, but not in those that do not share the particular feature, attribute or activity.

Characteristic sequence element: As used herein, the phrase "characteristic sequence element" refers to a sequence element found in a polymer (e.g., in a polypeptide or nucleic acid) that represents a characteristic portion of that polymer. In some embodiments, presence of a characteristic sequence element correlates with presence or level of a particular activity or property of the polymer. In some embodiments, presence (or absence) of a characteristic sequence element defines a particular polymer as a member (or not a member) of a particular family or group of such polymers. A characteristic sequence element typically comprises at least two monomers (e.g., amino acids or nucleotides). In some embodiments, a characteristic sequence element includes at least 2, 3, 4, 5, 6, 7, 8, 9, 10, 11, 12, 13, 14, 15, 20, 25, 30, 35, 40, 45, 50, or more monomers (e.g., contiguously linked monomers). In some embodiments, a characteristic sequence element includes at least first and second stretches of continuous monomers spaced apart by one or more spacer regions whose length may or may not vary across polymers that share the sequence element.

Codon-optimized: As used herein, a "codon-optimized" nucleic acid sequence refers to a nucleic acid sequence that has been altered such that translation of the nucleic acid sequence and expression of the resulting protein is improved optimized for a particular expression system. A "codon-optimized" nucleic acid sequence encodes the same protein as a non-optimized parental sequence upon which the "codon-optimized" nucleic acid sequence is based. For example, a nucleic acid sequence may be "codon-optimized" for expression in mammalian cells (e.g., CHO cells, human cells, mouse cells etc.), bacterial cells (e.g., E. coli), insect cells, yeast cells or plant cells.

Comparable: The term "comparable", as used herein, refers to two or more agents, entities, situations, sets of conditions, etc. that may not be identical to one another but that are sufficiently similar to permit comparison there between so that conclusions may reasonably be drawn based on differences or similarities observed. Those of ordinary skill in the art will understand, in context, what degree of identity is required in any given circumstance for two or more such agents, entities, situations, sets of conditions, etc. to be considered comparable.

Corresponding to: As used herein, the term "corresponding to" is often used to designate the position/identity of an amino acid residue in a polypeptide of interest (e.g., an HA polypeptide). Those of ordinary skill will appreciate that, for purposes of simplicity, residues in a polypeptide are often designated using a canonical numbering system based on a reference related polypeptide, so that an amino acid "corresponding to" a residue at position 190, for example, need not actually be the 190th amino acid in a particular amino acid chain but rather corresponds to the residue found at 190 in the reference polypeptide; those of ordinary skill in the art readily appreciate how to identify "corresponding" amino acids. Typically, residues in HA polypeptides are designated with reference to a canonical wild type HA, and reference in a polypeptide of interest that correspond to resides in the canonical wild type HA are described using the numbering of the residues to which they correspond.

Determine: Many methodologies described herein include a step of "determining". Those of ordinary skill in the art, reading the present specification, will appreciate that such "determining" can utilize any of a variety of techniques available to those skilled in the art, including for example specific techniques explicitly referred to herein. In some embodiments, a determination involves manipulation of a physical sample. In some embodiments, a determination involves consideration and/or manipulation of data or information, for example utilizing a computer or other processing unit adapted to perform a relevant analysis. In some embodiments, a determination involves receiving relevant information and/or materials from a source. In some embodiments, determining involves comparing one or more features of a sample or entity to a comparable reference.

Engineered: The term "engineered", as used herein, describes a polypeptide whose amino acid sequence has been designed by man and/or whose existence and production require human intervention and/or activity. For example, an engineered HA polypeptide has an amino acid sequence that is intentionally designed to elicit a particular effect and that differs from the amino acid sequences of HA polypeptides found in natural influenza isolates. In some embodiments, an engineered HA polypeptide has an amino acid sequence that differs from the amino acid sequence of HA polypeptides included in the NCBI database.

Epitope: As used herein, the term "epitope" includes any moiety that is specifically recognized by an immunoglobulin (e.g., antibody or receptor) binding component in whole or in part. In some embodiments, an epitope is comprised of a plurality of amino acids in an antigen. In some embodiments, such amino acid residues are surface-exposed when the antigen adopts a relevant three-dimensional conformation. In some embodiments, the amino acid residues are physically near to or contour with each other in space when the antigen adopts such a conformation. In some embodiments, at least some of the amino acids are physically separated from one another when the antigen adopts an alternative conformation (e.g., is linearized; eg., a non-linear epitope).

Excipient: As used herein, the term "excipient" refers to a non-therapeutic agent that may be included in a pharmaceutical composition, for example to provide or contribute to a desired consistency or stabilizing effect. Suitable pharmaceutical excipients include, for example, starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like.

Expression: The term "expression" or "expressed", when used in reference to a nucleic acid herein, refers to one or more of the following events: (1) production of an RNA transcript of a DNA template (e.g., by transcription); (2) processing of an RNA transcript (e.g., by splicing, editing, 5' cap formation, and/or 3' end formation); (3) translation of an RNA into a polypeptide; and/or (4) post-translational modification of a polypeptide.

Fusion protein: As used herein, the term "fusion protein" refers to a protein encoded by a nucleic acid sequence engineered from nucleic acid sequences encoding at least a portion of two different (e.g., heterologous) proteins. As persons of skill are no doubt aware, to create a fusion protein nucleic acid sequences are joined such that the resulting reading does not contain an internal stop codon. In some embodiments, fusion proteins as described herein include an influenza HA polypeptide or fragment thereof.

Hemagglutinin (HA) polypeptide: As used herein, the term "hemagglutinin polypeptide" (or "HA polypeptide") refers to a polypeptide whose amino acid sequence includes at least one characteristic sequence an influenza type A or type B HA. A wide variety of HA sequences from influenza isolates are known in the art; indeed, the National Center for Biotechnology Information (NCBI) maintains a database (ncbi.nlm.nih.gov/genomes/FLU/) that, as of the filing of the present application includes approximately 40,000 HA sequences (for type A and B influenza viruses). Those of ordinary skill in the art, referring to this database, can readily identify sequences that are characteristic of HA polypeptides generally, and/or of particular HA polypeptides (e.g., H1, H2, H3, H4, H5, H6, H7, H8, H9, H10, H11, H12, H13, H14, H15, or H16 polypeptides; or of HAs that mediate infection of particular hosts, e.g., avian, camel, canine, cat, civet, environment, equine, human, leopard, mink, mouse, seal, stone martin, swine, tiger, whale, etc.). For example, in some embodiments, an HA polypeptide includes one or more characteristic sequence elements found between about residues 97 and about 185, about 324 and about 340, about 96 and about 100, and/or about 130 and about 230 of an HA protein found in a natural isolate of an influenza virus.

H1N1 HA polypeptide: An "H1N1 HA polypeptide", as that term is used herein, is an HA polypeptide whose amino acid sequence includes at least one sequence element that is characteristic of H1N1 and distinguishes H1N1 from other HA subtypes. Representative sequence elements can be determined by alignments as will be understood by those skilled in the art.

Host: The term "host" is used herein to refer to a system (e.g., a cell, organism, etc.) in which a polypeptide of interest is present. In some embodiments, a host is a system that is susceptible to infection with a particular infectious agent. In some embodiments, a host is a system that expresses a particular polypeptide of interest.

Host cell: As used herein, the phrase "host cell" refers to a cell into which exogenous DNA (recombinant or otherwise) has been introduced. For example, host cells may be used to produce the engineered influenza hemagglutinin polypeptides described herein by standard recombinant techniques. Persons of skill upon reading this disclosure will understand that such terms refer not only to the particular subject cell, but, to the progeny of such a cell. Because certain modifications may occur in succeeding generations due to either mutation or environmental influences, such progeny may not, in fact, be identical to the parent cell, but are still included within the scope of the term "host cell" as used herein. In some embodiments, host cells include any prokaryotic and eukaryotic cells suitable for expressing an exogenous DNA (e.g., a recombinant nucleic acid sequence). Exemplary cells include those of prokaryotes and eukaryotes (single-cell or multiple-cell), bacterial cells (e.g., strains of *E. coli, Bacillus* spp., *Streptomyces* spp., etc.), mycobacteria cells, fungal cells, yeast cells (e.g., *S. cerevisiae, S. pombe, P. pastoris, P. methanolica*, etc.), plant cells, insect cells (e.g., SF-9, SF-21, baculovirus-infected insect cells, *Trichoplusia ni*, etc.), non-human animal cells, human cells, or cell fusions such as, for example, hybridomas or quadromas. In some embodiments, the cell is a human, monkey, ape, hamster, rat, or mouse cell. In some embodiments, the cell is eukaryotic and is selected from the following cells: CHO (e.g., CHO K1, DXB-11 CHO, Veggie-CHO), COS (e.g., COS-7), retinal cell, Vero, CV1, kidney (e.g., HEK293, 293 EBNA, MSR 293, MDCK, HaK, BHK), HeLa, HepG2, WI38, MRC 5, Colo205, HB 8065, HL-60, (e.g., BHK21), Jurkat, Daudi, A431 (epidermal), CV-1, U937, 3T3, L cell, C127 cell, SP2/0, NS-0, MMT 060562, Sertoli cell, BRL 3A cell, HT1080 cell, myeloma cell, tumor cell, and a cell line derived from an aforementioned cell. In some embodiments, the cell comprises one or more viral genes, e.g., a retinal cell that expresses a viral gene (e.g., a PER.C6™ cell).

Immune response: As used herein, the term "immune response" refers to a response of a cell of the immune system, such as a B cell, T cell, dendritic cell, macrophage or polymorphonucleocyte, to a stimulus such as an antigen or vaccine. An immune response can include any cell of the body involved in a host defense response, including for example, an epithelial cell that secretes an interferon or a cytokine. An immune response includes, but is not limited to, an innate and/or adaptive immune response. As used herein, a protective immune response refers to an immune response that protects a subject from infection (prevents infection or prevents the development of disease associated with infection). Methods of measuring immune responses are well known in the art and include, for example, measuring proliferation and/or activity of lymphocytes (such as B or T cells), secretion of cytokines or chemokines, inflammation, antibody production and the like.

Immunogen: As used herein, the term "immunogen" refers to a compound, composition, or substance which is capable, under appropriate conditions, of stimulating an immune response, such as the production of antibodies or a T cell response in an animal, including compositions that are injected or absorbed into an animal. As used herein, an "immunogenic composition" is an administerable composition comprising an immunogen (such as an HA polypeptide). "Immunogenic compositions" include, for example, vaccines. As used herein, "immunize" means to render a subject protected from an infectious disease, such as by vaccination.

In vitro: As used herein, the term "in vitro" refers to events that occur in an artificial environment, e.g., in a test tube or reaction vessel, in cell culture, etc., rather than within a multi-cellular organism.

In vivo: As used herein, the term "in vivo" refers to events that occur within a multi-cellular organism, such as a human and a non-human animal. In the context of cell-based systems, the term may be used to refer to events that occur within a living cell (as opposed to, for example, in vitro systems).

Influenza virus: As used herein, the term "influenza virus" refers to a segmented negative-strand RNA virus that belongs to the Orthomyxoviridae family. There are three types of Influenza viruses, A, B, and C. Influenza A viruses infect a wide variety of birds and mammals, including humans, horses, marine mammals, pigs, ferrets, and chickens. In animals, most influenza A viruses cause mild localized infections of the respiratory and intestinal tract. However, highly pathogenic influenza A strains, such as H5N1, cause systemic infections in poultry in which mortality may reach 100%. In 2009, H1N1 influenza was the most common cause of human influenza. A new strain of swine origin H1N1 emerged in 2009 and was declared pandemic by the World Health Organization. This strain was referred to as "swine flu." H1N1 influenza A viruses were also responsible for the Spanish flu pandemic in 1918, the Fort Dix outbreak in 1976, and the Russian flu epidemic in 1977-1978.

Influenza vaccine: As used herein, the term "influenza vaccine" refers to an immunogenic composition capable of stimulating an immune response, administered for the prevention, amelioration, or treatment of influenza virus infection. An influenza vaccine may include, for example, attenuated or killed influenza virus, virus-like particles (VLPs) and/or antigenic polypeptides (e.g., the engineered hemagglutinins described herein) or DNA derived from them, or any recombinant versions of such immunogenic materials.

Isolated: As used herein, the term "isolated" refers to a substance and/or entity that has been (1) separated from at least some of the components with which it was associated when initially produced (whether in nature and/or in an experimental setting), and/or (2) designed, produced, prepared, and/or manufactured with human intervention. Isolated substances and/or entities may be separated from about 10%, about 20%, about 30%, about 40%, about 50%, about 60%, about 70%, about 80%, about 90%, about 91%, about 92%, about 93%, about 94%, about 95%, about 96%, about 97%, about 98%, about 99%, or more than about 99% of the other components with which they were initially associated. In some embodiments, isolated agents are about 80%, about 85%, about 90%, about 91%, about 92%, about 93%, about 94%, about 95%, about 96%, about 97%, about 98%, about 99%, or more than about 99% pure. As used herein, a substance is "pure" if it is substantially free of other components. In some embodiments, as will be understood by those skilled in the art, a substance may still be considered "isolated" or even "pure", after having been combined with certain other components such as, for example, one or more carriers or excipients (e.g., buffer, solvent, water, etc.); in such embodiments, percent isolation or purity of the substance is calculated without including such carriers or excipients. To give but one example, in some embodiments, a biological polymer such as a polypeptide or polynucleotide that occurs in nature is considered to be "isolated" when, a) by virtue of its origin or source of derivation is not associated with some or all of the components that accompany it in its native state in nature; b) it is substantially free of other polypeptides or nucleic acids of the same species from the species that produces it in nature; c) is expressed by or is otherwise in association with components from a cell or other expression system that is not of the species that produces it in nature. Thus, for instance, in some embodiments, a polypeptide that is chemically synthesized or is synthesized in a cellular system different from that which produces it in nature is considered to be an "isolated" polypeptide. Alternatively or additionally, in some embodiments, a polypeptide that has been subjected to one or more purification techniques may be considered to be an "isolated" polypeptide to the extent that it has been separated from other components a) with which it is associated in nature; and/or b) with which it was associated when initially produced.

Nucleic acid: As used herein, the phrase "nucleic acid", in its broadest sense, refers to any compound and/or substance that is or can be incorporated into an oligonucleotide chain. In some embodiments, a nucleic acid is a compound and/or substance that is or can be incorporated into an oligonucleotide chain via a phosphodiester linkage. As will be clear from context, in some embodiments, "nucleic acid" refers to individual nucleic acid residues (e.g., nucleotides and/or nucleosides); in some embodiments, "nucleic acid" refers to an oligonucleotide chain comprising individual nucleic acid residues. In some embodiments, a "nucleic acid" is or comprises RNA; in some embodiments, a "nucleic acid" is or comprises DNA. In some embodiments, a nucleic acid is, comprises, or consists of one or more natural nucleic acid residues. In some embodiments, a nucleic acid is, comprises, or consists of one or more nucleic acid analogs. In some embodiments, a nucleic acid analog differs from a nucleic acid in that it does not utilize a phosphodiester backbone. For example, in some embodiments, a nucleic acid is, comprises, or consists of one or more "peptide nucleic acids", which are known in the art and have peptide bonds instead of phosphodiester bonds in the backbone, are considered within the scope of the present invention. Alternatively or additionally, in some embodiments, a nucleic acid has one or more phosphorothioate and/or 5'-N-phosphoramidite linkages rather than phosphodiester bonds. In some embodiments, a nucleic acid is, comprises, or consists of one or more natural nucleosides (e.g., adenosine, thymidine, guanosine, cytidine, uridine, deoxyadenosine, deoxythymidine, deoxyguanosine, and deoxycytidine). In some embodiments, a nucleic acid is, comprises, or consists of one or more nucleoside analogs (e.g., 2-aminoadenosine, 2-thiothymidine, inosine, pyrrolo-pyrimidine, 3-methyl adenosine, 5-methylcytidine, C-5 propynyl-cytidine, C-5 propynyl-uridine, 2-aminoadenosine, C5-bromouridine, C5-fluorouridine, C5-iodouridine, C5-propynyl-uridine, C5-propynyl-cytidine, C5-methylcytidine, 2-aminoadenosine, 7-deazaadenosine, 7-deazaguanosine, 8-oxoadenosine, 8-oxoguanosine, O(6)-methylguanine, 2-thiocytidine, methylated bases, intercalated bases, and combinations thereof). In some embodiments, a nucleic acid comprises one or more modified sugars (e.g., 2'-fluororibose, ribose, 2'-deoxyribose, arabinose, and hexose) as compared with those in natural nucleic acids. In some embodiments, a nucleic acid has a nucleotide sequence that encodes a functional gene product such as an RNA or protein. In some embodiments, a nucleic acid includes one or more introns. In some embodiments, nucleic acids are prepared by one or more of isolation from a natural source, enzymatic synthesis by polymerization based on a complementary template (in vivo or in vitro), reproduction in a recombinant cell or system, and chemical synthesis. In some embodiments, a nucleic acid is at least 3, 4, 5, 6, 7, 8, 9, 10, 15, 20, 25, 30, 35, 40, 45, 50, 55, 60, 65, 70, 75, 80, 85, 90, 95, 100, 110, 120, 130, 140, 150, 160, 170, 180, 190, 20, 225, 250, 275, 300, 325, 350, 375, 400, 425, 450, 475, 500, 600, 700, 800, 900, 1000, 1500, 2000, 2500, 3000, 3500, 4000, 4500, 5000 or more residues long. In some embodiments, a nucleic acid is single stranded; in some embodiments, a nucleic acid is double stranded. In some embodiments a nucleic acid has a nucleotide sequence comprising at least one element that encodes, or is the complement of a sequence that encodes, a polypeptide. In some embodiments, a nucleic acid has enzymatic activity.

Pandemic strain: A "pandemic" influenza strain is one that has caused or has capacity to cause pandemic infection of human populations. In some embodiments, a pandemic strain has caused pandemic infection. In some embodiments, such pandemic infection involves epidemic infection across multiple territories; in some embodiments, pandemic infection involves infection across territories that are separated from one another (e.g., by mountains, bodies of water, as part of distinct continents, etc.) such that infections ordinarily do not pass between them.

Pharmaceutically acceptable vehicles: The pharmaceutically acceptable carriers (vehicles) useful in this disclosure are conventional. Remington's Pharmaceutical Sciences, by E. W. Martin, Mack Publishing Co., Easton, Pa., $15^{th}$ Edition (1975), describes compositions and formulations suitable for pharmaceutical delivery of one or more therapeutic compositions, such as one or more influenza vaccines, and additional pharmaceutical agents. In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (for example, powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Polypeptide: A "polypeptide", generally speaking, is a string of at least two amino acids attached to one another by a peptide bond. In some embodiments, a polypeptide may include at least 3-5 amino acids, each of which is attached to others by way of at least one peptide bond. Those of ordinary skill in the art will appreciate that polypeptides sometimes include "non-natural" amino acids or other entities that nonetheless are capable of integrating into a polypeptide chain, optionally. In some embodiments, the term "polypeptide" is used to refer to specific functional classes of polypeptides, such as, HA polypeptides, etc. For each such class, the present specification provides and/or the art is aware of several examples of amino acid sequences of known exemplary polypeptides within the class; in some embodiments, one or more such known polypeptides is/are reference polypeptides for the class. In such embodiments, the term "polypeptide" refers to any member of the class that shows sufficient sequence homology or identity with a relevant reference polypeptide that one skilled in the art would appreciate that it should be included in the class. In many embodiments, such member also shares significant activity with the reference polypeptide. For example, in some embodiments, a member polypeptide shows an overall degree of sequence homology or identity with a reference polypeptide that is at least about 30-40%, and is often greater than about 50%, 60%, 70%, 80%, 90%, 91%, 92%, 93%, 94%, 95%, 96%, 97%, 98%, 99% or more and/or includes at least one region (i.e., a conserved region, often including a characteristic sequence element) that shows very high sequence identity, often greater than 90% or even 95%, 96%, 97%, 98%, or 99%. Such a conserved region usually encompasses at least 3-4 and often up to 20 or more amino acids; in some embodiments, a conserved region encompasses at least one stretch of at least 2, 3, 4, 5, 6, 7, 8, 9, 10, 11, 12, 13, 14, 15 or more contiguous amino acids. In some embodiments, a useful polypeptide (e.g., an engineered HA polypeptide as described herein) may comprise or consist of a fragment of a parent polypeptide (e.g., an epitope). In some embodiments, a useful polypeptide as may comprise or consist of multiple (e.g., two, three, four, etc.) fragments (e.g., epitopes), each of which is found in the same parent polypeptide in a different spatial arrangement relative to one another than is found in the polypeptide of interest (e.g., fragments that are directly linked in the parent may be spatially separated in the polypeptide of interest or vice versa, and/or fragments may be present in a different order in the polypeptide of interest than in the parent), so that the polypeptide of interest is a derivative of its parent polypeptide. Alternatively, in some embodiments, a useful polypeptide may comprise or consist of multiple (e.g., two, three, four, etc.) fragments (e.g., epitopes), each of which is found in different parent polypeptides than the polypeptide of interest (e.g., fragments that originate in different parent polypeptides, and/or fragments may be present in a different order in the polypeptide of interest than in the parent polypeptides), so that the polypeptide of interest is a derivative of its parent polypeptides.

Prevention: The term "prevention", as used herein, refers to prophylaxis, avoidance of disease manifestation, a delay of onset, and/or reduction in frequency and/or severity of one or more symptoms of a particular disease, disorder or condition (e.g., infection for example with influenza virus). In some embodiments, prevention is assessed on a population basis such that an agent is considered to "prevent" a particular disease, disorder or condition if a statistically significant decrease in the development, frequency, and/or intensity of one or more symptoms of the disease, disorder or condition is observed in a population susceptible to the disease, disorder, or condition.

Pure: As used herein, an agent or entity is "pure" if it is substantially free of other components. For example, a preparation that contains more than about 90% of a particular agent or entity is typically considered to be a pure preparation. In some embodiments, an agent or entity is at least 91%, at least 92%, at least 93%, at least 94%, at least 95%, at least 96%, at least 97%, at least 98%, or at least 99% pure.

Receptor-Binding Site (RBS): As used herein, the term "receptor-binding site" or "RBS" comprises contiguous or non-contiguous amino acid residues of the head region of an influenza HA polypeptide, which include amino acids involved in direct binding of sialic acid on the target cell receptor proteins. Amino acid residues that make up a "receptor-binding site" or "RBS" of an influenza HA polypeptide may be described from crystal structures of HA polypeptides complexed with sialic acid analogs and identifying amino acid residues within a certain proximity to the analog or may be described in reference to an HA polypeptide sequence from a particular viral strain (e.g., B/Victoria/02/1987, B/Yamagata/16/1988, B/Brisbane/60/2008; A/New Caledonia/20/99 or A/California/07/2009). Thus, in some embodiments, the "receptor-binding site" or "RBS" of an engineered HA polypeptide as described herein may be determined using a reference HA polypeptide sequence. In some embodiments, the "receptor-binding site" or "RBS" of an engineered HA polypeptide as described herein may be determined using the crystal structures of HA polypeptide sequence in complex with human and avian receptor analogs (ex. LSTa, LSTc). An exemplary reference crystal structure of HA polypeptide sequence in complex with LSTc includes A/Puerto Rico/8/1934 (H1N1) pdbl1RVZ.

Recombinant: As used herein, the term "recombinant" is intended to refer to polypeptides (e.g., HA polypeptides as described herein) that are designed, engineered, prepared, expressed, created or isolated by recombinant means, such as polypeptides expressed using a recombinant expression vector transfected into a host cell, polypeptides isolated from a recombinant, combinatorial polypeptide library or polypeptides prepared, expressed, created or isolated by any other means that involves splicing selected sequence elements to one another. In some embodiments, one or more of such selected sequence elements is found in nature. In some embodiments, one or more of such selected sequence elements and/or combinations thereof is designed in silico. In some embodiments, one or more such selected sequence elements results from the combination of multiple (e.g., two or more) known sequence elements that are not naturally present in the same polypeptide (e.g., two epitopes from two separate HA polypeptides).

Recombinant influenza vaccine: As used herein, the term "recombinant influenza vaccine" refers to influenza-specific immunogenic composition comprising one or more of the engineered influenza hemagglutinins described herein, including, but not limited to whole influenza virus, subunit preparations thereof, virus-like particles, recombinant protein (i.e., preparations composed of recombinant HA purified to varying degree), and DNA- and viral vector-based vaccines. Recombinant influenza vaccines as described herein may optionally contain one or more adjuvants.

Reference: The term "reference" is often used herein to describe a standard or control agent, individual, population, sample, sequence or value against which an agent, individual, population, sample, sequence or value of interest is compared. In some embodiments, a reference agent, individual, population, sample, sequence or value is tested and/or determined substantially simultaneously with the testing or determination of the agent, individual, population, sample, sequence or value of interest. In some embodiments, a reference agent, individual, population, sample, sequence or value is a historical reference, optionally embodied in a tangible medium. Typically, as would be understood by those skilled in the art, a reference agent, individual, population, sample, sequence or value is determined or characterized under conditions comparable to those utilized to determine or characterize the agent, individual, population, sample, sequence or value of interest.

Subject: As used herein, the term "subject" means any mammal, including humans. In certain embodiments of the present invention the subject is an adult, an adolescent or an infant. In some embodiments, terms "individual" or "patient" are used and are intended to be interchangeable with "subject". Also contemplated by the present invention are the administration of the pharmaceutical compositions and/or performance of the methods of treatment in-utero.

Substantially: As used herein, the term "substantially" refers to the qualitative condition of exhibiting total or near-total extent or degree of a characteristic or property of interest. One of ordinary skill in the biological arts will understand that biological and chemical phenomena rarely, if ever, go to completion and/or proceed to completeness or achieve or avoid an absolute result. The term "substantially" is therefore used herein to capture the potential lack of completeness inherent in many biological and chemical phenomena.

Transformation: As used herein, refers to any process by which exogenous DNA is introduced into a host cell. Transformation may occur under natural or artificial conditions using various methods well known in the art. Transformation may rely on any known method for the insertion of foreign nucleic acid sequences into a prokaryotic or eukaryotic host cell. In some embodiments, a particular transformation methodology is selected based on the host cell being transformed and may include, but is not limited to, viral infection, electroporation, mating, lipofection. In some embodiments, a "transformed" cell is stably transformed in that the inserted DNA is capable of replication either as an autonomously replicating plasmid or as part of the host chromosome. In some embodiments, a transformed cell transiently expresses introduced nucleic acid for limited periods of time.

Vaccination: As used herein, the term "vaccination" refers to the administration of a composition intended to generate an immune response, for example to a disease-causing agent. Vaccination can be administered before, during, and/or after exposure to a disease-causing agent, and/or to the development of one or more symptoms, and in some embodiments, before, during, and/or shortly after exposure to the agent. In some embodiments, vaccination includes multiple administrations, appropriately spaced in time, of a vaccinating composition.

Vector: As used herein, the term "vector" refers to a nucleic acid molecule capable of transporting another nucleic acid to which it has been linked. One type of vector is a "plasmid", which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "expression vectors."

Virus-like particle (VLP): As used herein, the phrase "virus-like particle" or "VLP" refers to particles that resemble a virus yet lack any viral genetic material and, therefore, are not infectious. A "virus-like particle" or "VLP" may be produced by heterologous expression in a variety of cell culture systems including mammalian cell lines, insect cell lines, yeast, and plant cells. In addition, VLPs can be purified by methods known in the art. In some embodiments, an influenza VLP as described herein comprises hemagglutinin (HA) polypeptides and neuraminidase (NA) polypeptides. In some embodiments, influenza VLPs as described herein comprise HA polypeptides, NA polypeptides and/or viral structural polypeptides (e.g., an influenza structural protein such as influenza M1). In some certain embodiments, influenza VLPs as described herein comprise HA polypeptides, NA polypeptides and/or M1 polypeptides. In some embodiments, influenza VLPs as described herein comprise HA polypeptides, NA polypeptides and/or HIVgag polypeptides. Influenza VLPs can be produced by transfection of host cells (e.g., mammalian cells) with plasmids encoding HA and NA proteins, and optionally HIV gag proteins. After incubation of the transfected cells for an appropriate time to allow for protein expression (such as for approximately 72 hours), VLPs can be isolated from cell culture supernatants. In some embodiments, influenza VLPs as described herein are produced by transient transfection in mammalian cells (e.g., human cells). In some embodiments, influenza VLPs are analyzed by the use of one or more assays. To give but a few examples, influenza VLPs may be analyzed for hemagglutinin activity, dynamic light scattering and hemmagglutinin content quantitation by protein staining. Other assays will be readily apparent to persons of skill upon reviewing the present disclosure.

Wild type: As is understood in the art, the phrase "wild type" generally refers to a normal form of a protein or nucleic acid, as is found in nature. For example, wild type HA polypeptides are found in natural isolates of influenza virus. A variety of different wild type HA sequences can be found in the NCBI influenza virus sequence database, available through the world wide web at ncbi.nlm.nih.gov/genomes/FLU/FLU.

DETAILED DESCRIPTION OF CERTAIN EMBODIMENTS

The present invention is not limited to particular methods, and experimental conditions described, as such methods and conditions may vary. It is also to be understood that the terminology used herein is for the purpose of describing particular embodiments only, and is not intended to be limiting unless indicated, since the scope of the present invention will be limited only by the appended claims.

Unless stated otherwise, all technical and scientific terms and phrases used herein have the same meaning as commonly understood by one of ordinary skill in the art. Although any methods and materials similar or equivalent to those described herein can be used in the practice or testing of the present invention, the preferred methods and materials are now described. All publications mentioned herein are incorporated herein by reference.

Standard techniques may be used for recombinant DNA, oligonucleotide synthesis, and tissue culture and transformation (e.g., electroporation, lipofection). Enzymatic reactions and purification techniques may be performed according to manufacturer's specifications or as commonly accomplished in the art or as described herein. The foregoing techniques and procedures may be generally performed according to conventional methods well known in the art and as described in various general and more specific references that are cited and discussed throughout the present specification. See e.g., Sambrook et al. Molecular Cloning: A Laboratory Manual (2d ed., Cold Spring Harbor Laboratory Press, Cold Spring Harbor, N.Y. (1989)), which is incorporated herein by reference for any purpose.

Generation of Engineered Mosaic Influenza Antigens

Influenza viruses are members of the family Orthomyxoviridae and are divided into three genera, A, B, and C. Influenza A and B viruses cause respiratory infections in humans. Despite the availability of highly effective vaccines, influenza infection still results in up to 5,000,000 hospitalizations and 500,000 deaths annually worldwide. Current vaccines are designed to induce immunity to hemagglutinin, one of two glycoproteins present on the surface of influenza viruses. Available vaccines against influenza include up to four influenza hemagglutinin components intended to provide protection against H1N1, H3N2, and influenza B strains.

Hemagglutinin (HA) is responsible for the binding of influenza virus to target cells with sialic acid on their membranes. Over time, HA accumulates mutations in its sequence in a process termed 'antigenic drift', allowing the virus to evade the human immune response.

Vaccine compositions are reassessed annually by the World Health Organization (WHO) to accommodate antigenic shift and drift in circulating virus strains. Such a strategy requires diligent surveillance of circulating influenza strains from year to year, and vaccine mismatches resulting from inaccurate predictions or unpredictable HA or NA mutations arising during vaccine manufacture, which can result in increased morbidity and mortality even in vaccinated populations.

Engineered HA polypeptides as described herein address the shortcomings of the currently available vaccines. In some embodiments, engineered HA polypeptides as described herein achieve a greater efficacy against mismatched strains and/or strains associated with an increased morbidity and/or mortality. In some embodiments, engineered HA polypeptides as described herein provide enhanced protection against influenza during mismatch years thereby reducing reliance on accurate strain predictions from year to year. In some embodiments, engineered HA polypeptides as described herein are used in vaccines and allow for less frequent immunizations by providing sufficient breadth of immunity to cover antigenic drift that generally accumulates between seasons of influenza infection.

Engineered HA polypeptides of the present invention, in some embodiments, address the lack of breadth and cross-protection observed in current influenza vaccine formulations. For example, in some embodiments, engineered HA polypeptides as described herein provide a cross protective immune response against Influenza A subtypes including H1N1 and H3N5. In some embodiments, engineered HA polypeptides as described herein may be used alone or in combination with other influenza antigens, including wild type influenza antigens. In some embodiments, engineered HA polypeptides of the present invention may be used as a component of seasonal and pandemic influenza vaccines and/or as part of influenza vaccination regimens intended to confer long-lasting, multi-season protection.

Structural Mapping of Antigenic Repertoires

Figure 1:
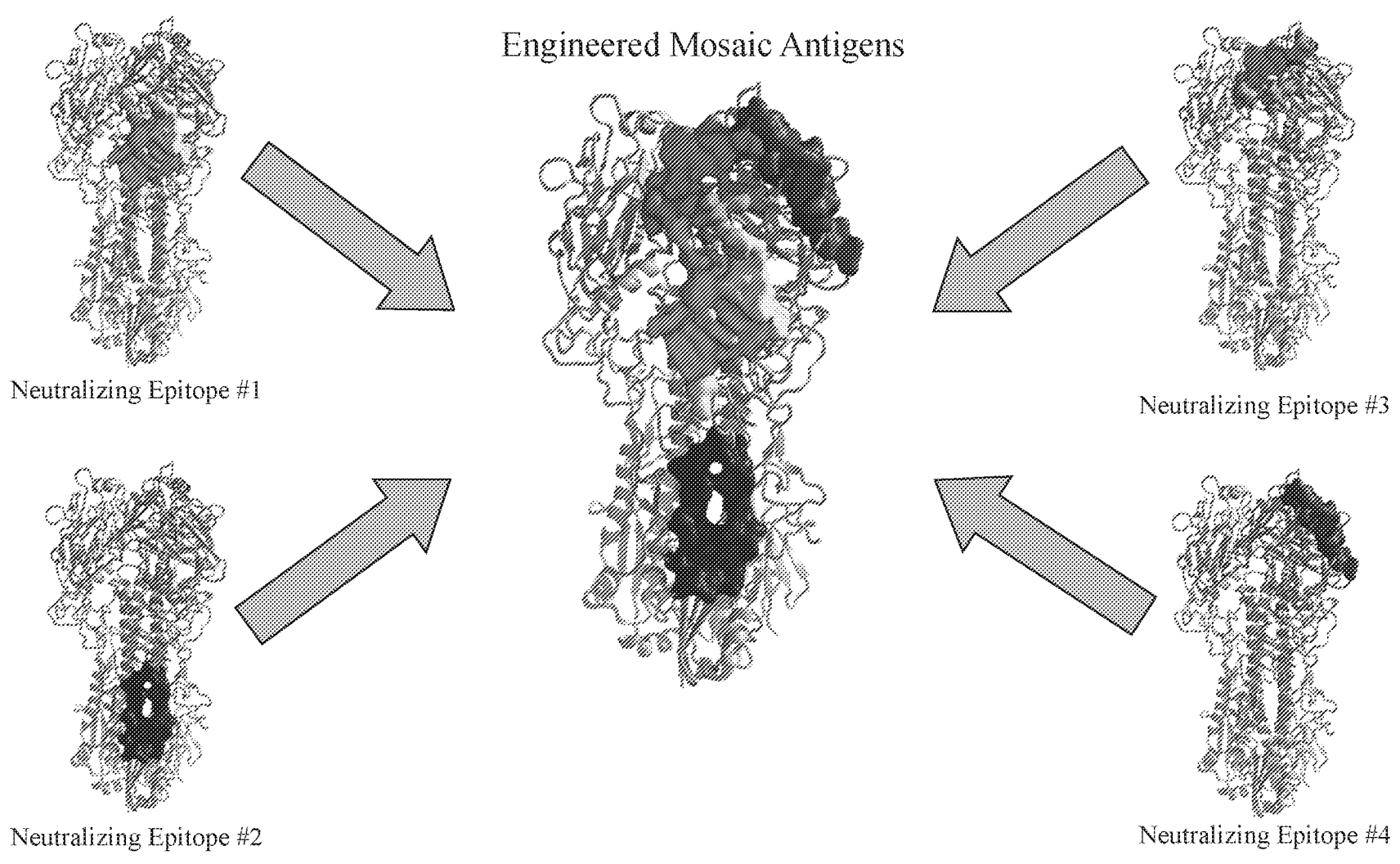

One rational design approach to creating a broadly protective influenza vaccine is to engineer antigens that include epitopes from as many viral isolates as possible. According to the present invention, generation of mosaic epitope sequences, in particular—B-cell epitope sequences-can be achieved using a methodology termed SMARt for the 'Structural Mapping of Antigenic Repertoires'. Engineered hemagglutinin (HA) polypeptides are molecular entities that specifically elicit an immune response in a subject. Such engineered HA polypeptides find a variety of uses in the art, including prophylactic and therapeutic uses. Engineered HA polypeptides of the present invention, in some embodiments, address the lack of breadth and cross-protection observed in current influenza vaccine formulations. The present invention is based, in part, on the recognition that a rational design approach to creating a broadly protective influenza vaccine can be developed by providing engineered influenza antigenic polypeptides (for example, hemagglutinin, neuraminidase, M2e, etc.) that include epitopes from multiple viral isolates in a polyvalent vaccine (FIG. 1). The designs, in some embodiments, are based on combinations of multiple B cell epitopes and antigenic regions from different hemagglutinin sequences (subtype H1) into mosaic antigens. These mosaic epitope antigens, in some embodiments, confer cross-protection against multiple influenza A strains by maximizing sequence homology for at least one neutralizing epitope.

In some embodiments, engineered HA polypeptides as described herein may be used alone or in combination with other influenza antigens. In some embodiments, engineered HA polypeptides of the present invention may be used as a component of seasonal and pandemic influenza vaccines or as part of influenza vaccination regimens intended to confer long-lasting, multi-season protection. FIG. 2 sets forth a general strategy for the construction of engineered HA polypeptides of the present invention.

In some embodiments, a method of engineering a mosaic influenza hemagglutinin (HA) polypeptide according to the SMARt methodology comprises the steps of: (1) obtaining HA amino acid sequences from multiple circulating strains of a particular type and/or subtype of influenza virus; (2) aligning the HA amino acid sequences to generate an alignment; identifying the positions of amino acids comprising known epitopes and antigenic regions; (3) compiling the amino acid residues across the alignment at the identified positions for each epitope and antigenic region; (3) defining a set of amino acid sequence patterns within the compiled sequences for each epitope and antigenic region, wherein each amino sequence pattern in the set is represented only once; (4) selecting a sequence from the set for each epitope or antigenic region; and (5) inserting selected sequences into corresponding locations in a structural backbone of HA to generate a mosaic influenza HA polypeptide. Alternatively, instead of selecting a unique sequence at step (4), a consensus sequence is defined from each set for each epitope or antigenic region. These methods can be used to engineer any influenza antigenic polypeptides, including Type A and B hemagglutinins, neuraminidase, and M2e.

The present invention is based on the application of a methodology for the generation of mosaic B cell epitope sequences through structural mapping of antigenic repertoires. Vaccines developed to target specific viral isolates may not protect against infection from different isolates of the same virus. The approach for developing broadly protective antigens of the present invention, in some embodiments, creates polyvalent mosaic sequences that include B cell epitopes from as many viral isolates as possible. Known neutralizing antibody epitopes and antigenic sites are recombined to generate mosaic antigens. The best mosaic sequence templates are selected by evaluating overall alignment coverage by geographic regions, viral isolate years, sequence clusters or other scoring methods. The selected set of mosaic template sequences are combined with target backbone sequences to generate a set of full-length mosaic protein sequences. Structure refinement of these mosaic sequences yields the final set of vaccination proteins.

In some embodiments, the present invention is based on combinations of neutralizing and non-neutralizing hemagglutinin B cell epitope patterns derived from multiple influenza A subtypes to generate novel mosaic designs for influenza hemagglutinin. Each design, consisting of a mosaic pattern of B-cell epitopes, is combined with a backbone hemagglutinin sequence. For example, the inventors have employed two backbone hemagglutinin sequences: A/New Caledonia/20/99 (pre-pandemic), A/California/07/2009 (pandemic). As persons of skill are aware, other hemagglutinin backbone sequences may also be employed for construction of engineered HA polypeptides according to the present invention. In some embodiments, a backbone sequence provides the inter-epitope sequence as well as the signal peptide and transmembrane domains required for full-length hemagglutinin molecules that are expressed and functional. As persons of skill are no doubt aware, other signal peptides may be used as desired.

Briefly, known neutralizing and non-neutralizing hemagglutinin B-cell epitopes described for any influenza A subtype are mapped to corresponding regions of the H1 subtype of influenza A. Individual sequences (antigenic repertoires) for each B cell epitopes are extracted and enumerated from the sequences of all available circulating strains (H1 subtype). Distinct workflows have been developed to combine the antigenic repertoires into novel mosaic hemagglutinin molecules that are distinct from natural circulating strains.

Various techniques may be used to obtain, align and select influenza sequences for each epitope or antigenic region. For example, Principal Components Analysis (PCA) is a common technique for working with high dimensional data and highlighting patterns in the data (i.e. it can be used to simplify large datasets and facilitate data exploration and visualization). Applied to biological sequences (proteins, genes), the technique enables comparison of thousands of sequences and the identification of groups of similar sequences based on a measure of sequence dissimilarity (Hamming distance, percent identity, percent similarity, surface accessibility, etc). In the case of Human influenza viruses, influenza antigen protein sequences may be obtained from all publicly available influenza antigen amino acid sequences including, but not limited to, those available HA or NA amino acid sequences in the NCBI Influenza Virus Resource database. In some embodiments, more than 100, 500, 1000, 2000, 3000, 4000, 5000, 6000, 7000, 8000, 9000, 10,000, 12,000, 14,000, or 15,000 HA or NA amino acid sequences from multiple circulating influenza strains are obtained. In some embodiments, 100-5000, 100-6000, 100-7000, 100-8000, 100-9000, 100-10,000, 100-15,000, or 100-20,000 HA or NA amino acid sequences from multiple circulating influenza strains are obtained.

In some embodiments, HA or NA protein sequences are obtained from more than 5, 10, 15, 20, 25, 30, 35, 40, 45, 50, 60, 70, 80, 90 or 100 circulating influenza strains. In some embodiments, HA or NA amino acid sequences utilized in the present invention are obtained of a particular type and/or subtype of influenza virus. For example, HA or NA amino acid sequences may be obtained from a type A influenza virus. In some embodiments, the HA protein of an influenza A virus is selected from subtypes H1, H2, H3, H4, H5, H6, H7, H8, H9, H10, H11, H12, H13, H14, H15, or H16. In some embodiments, the influenza virus is selected from the group consisting of H1N1, H3N2, H5N1, and H7N9. In some embodiments, the type A virus is a seasonal strain, such as, /Texas/36/1991, A/Singapore/1986, A/New Caledonia/20/1999, A/Solomon Islands/03/2006, A/Brisbane/59/2007, or A/Wisconsin/67/2005. In some embodiments, the type A virus is a pandemic strain such as A/California/07/2009, A/California/04/2009, A/Belgium/145/2009, A/South Carolina/01/1918, or A/New Jersey/1976.

Typically, HA or NA amino acid sequences are trimmed to remove signal peptides, transmembrane regions and cytoplasmic tails and the resulting ectodomain sequences are aligned. In some embodiments, redundant sequences are removed before alignment by screening the HA or NA amino acid sequences for those with 100%, or greater than 99.9%, 99% 98%, 97%, or 96%, sequence identity, and removing all but one of the redundant sequences.

Visualization of principal components may be used to identify patterns associated with influenza A hemagglutinins including the multiple influenza A subtypes. Additionally, sequences form distinct clusters based on similarity.

Modifications designed into the engineered HAs or NAs is deduced from an in silico analysis of sequence variation in both past and current circulating influenza strains. This analysis includes mapping antigenic and epitope patterns as well as structural modeling of the HA or NA protein. Targeted changes are subsequently introduced at corresponding amino acid residue locations and/or specific regions of the protein with known immune profiles in order to yield novel influenza HA or NA polypeptides that would be reactive across the sequence clusters.

Each novel mosaic design is composed of multiple neutralizing HA or NA B-cell epitope patterns derived from antigenically diverse influenza strains. The mosaic pattern of B-cell epitopes is assembled onto a backbone hemagglutinin or neuraminidase sequence. As non-limiting examples, suitable backbone hemagglutinin or neuraminidase sequences may be derived from: /Texas/36/1991, A/Singapore/1986, A/New Caledonia/20/1999, A/Solomon Islands/03/2006, A/Brisbane/59/2007, or A/Wisconsin/67/2005, A/California/07/2009, A/California/04/2009, A/Belgium/145/2009, A/South Carolina/01/1918, or A/New Jersey/1976. However, other backbone sequences could also be contemplated for this invention. The selected backbone provides the inter-epitope sequence of the engineered construct as well as the signal peptide and transmembrane domains required for full-length hemagglutinin molecules that are expressed and functional.

Exemplary SMARt Workflows

Figure 3:
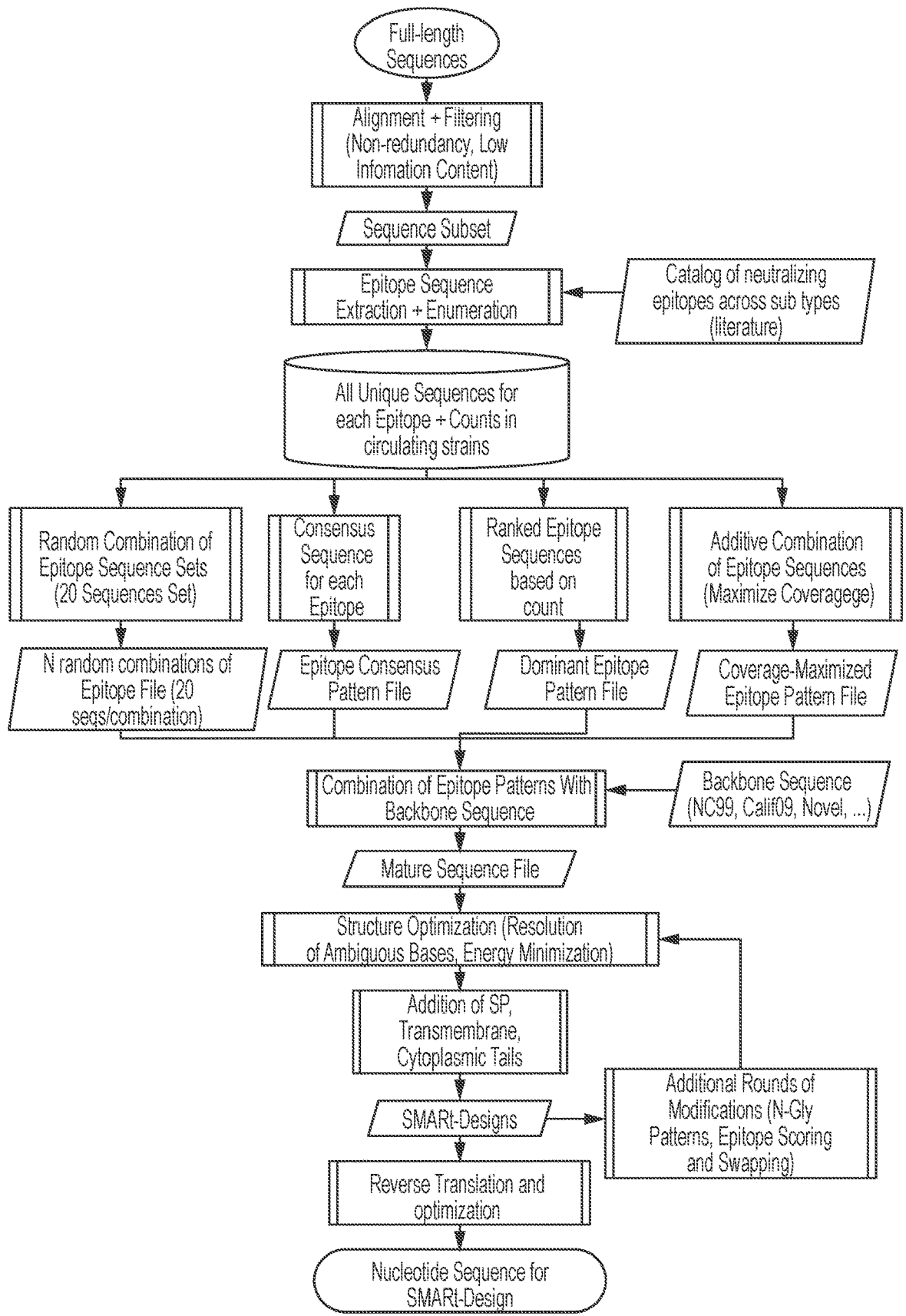
FIG. 3 shows an exemplary flowchart for the design and production of engineered antigenic polypeptides.

Briefly, known neutralizing and non-neutralizing hemagglutinin B-cell epitopes described for any influenza virus are mapped to corresponding regions of influenza HA or NA. Individual sequences for each B-cell epitope are extracted and enumerated from the sequences of all available circulating Influenza strains to generate an "antigenic repertoire". Individual sequences corresponding to different antigenic regions of HA or NA can be selected (or, alternatively, distilled into a consensus sequence) from the antigenic repertoire for each mapped epitope site and combined into novel mosaic pattern antigens (for example, epitope site 1 from circulating strain X, epitope site 2 from circulating strain Y, epitope site 3 from circulating strain Z, etc.) on a particular backbone strain, wherein the combination may be chosen or selected to elicit a particular immune response. Four distinct SMARt workflows are developed to combine antigenic repertoires into novel mosaic hemagglutinin molecules that are distinct from natural circulating strains. An overview of the compiled SMARt workflow is presented in FIG. 3.

In general, known neutralizing and non-neutralizing hemagglutinin B-cell epitopes described for any influenza strain are mapped to corresponding regions of the HA backbone. Individual sequences (antigenic repertoires) for each B cell epitope are extracted and enumerated from the sequences of all available circulating influenza strains. Distinct workflows have been developed to combine the antigenic repertoires into novel mosaic hemagglutinin molecules that are distinct from natural circulating strains.

Four non-limiting exemplary SMARt workflows are:

1. SMARt Random: B-cell epitope sequences for each of the mapped epitope sites are combined at random (drawn from all unique sequences for each epitope site in the antigenic repertoire). The resulting random combinations are scored for coverage of naturally occurring strains (by year, geography, and sequence coverage) and the highest scoring combinations are selected. The highest scoring selections based on breadth of coverage across naturally occurring strains by year, geography and sequence cluster are then combined with one a backbone sequence 2. SMARt Choice: Unique epitope sequences for each mapped epitope site are combined to maximize breadth of coverage across naturally occurring strains. An initial seed epitope is selected, and for each additional epitope added to the mosaic, a sequence is selected from the antigenic repertoire of the site that maximizes the breadth of coverage (i.e. as many naturally occurring strains as possible matched by at least one epitope). The highest scoring selections based on breadth of coverage across naturally occurring strains by year, geography and sequence cluster are then combined into one backbone sequence 3. SMARt Collapsed: A consensus sequence for each epitope is defined from the unique antigenic repertoire for that epitope site. The consensus sequences for each distinct epitope site are combined into a single mosaic pattern for the antigen and merged into a backbone sequence. This approach determines the consensus of unique epitope sequences for all epitope sites, combines the epitope consensus sequence into a mosaic pattern template, and combines the mosaic pattern template with desired backbone sequence(s).

Figure 4:
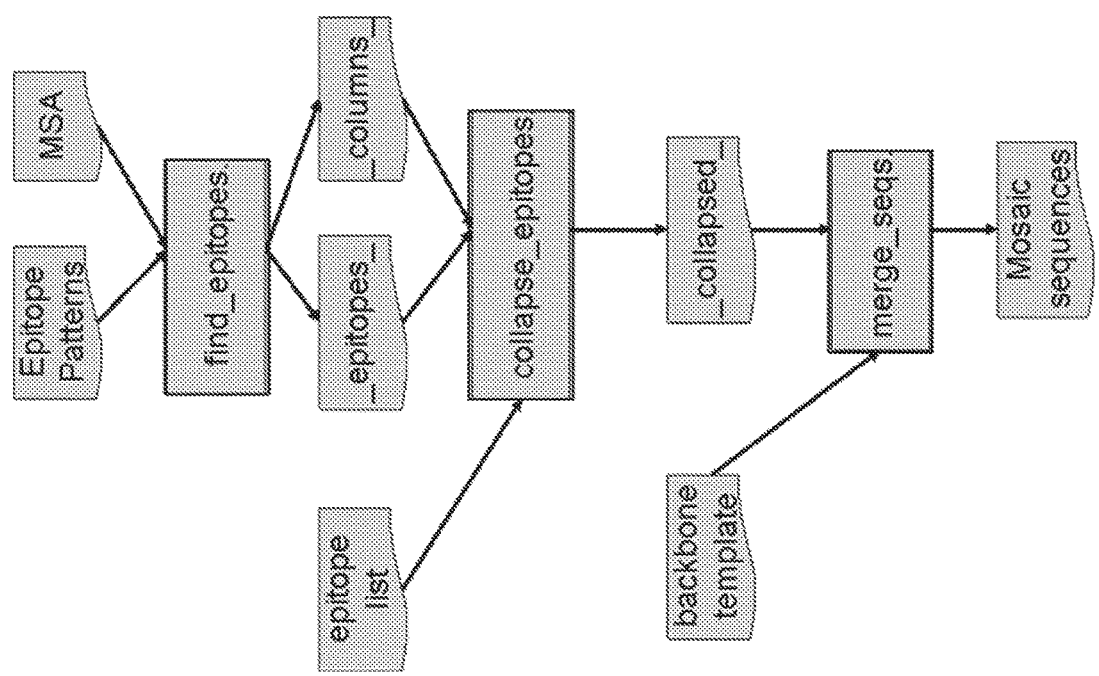
FIG. 4 shows an exemplary flowchart for the design and production of engineered antigenic polypeptides using the collapse epitopes process.

The collapsed epitopes approach generates a single sequence for each mapped epitope site in the mosaic using a consensus approach. The unique amino acid residues comprising epitope sequences are identified from the antigenic repertoire. The most common amino acid at a given position for each mapped epitope site is used in the mosaic template pattern. The data flow and method steps are overviewed in FIG. 4. An upper case letter is used for residues that occur in 75+% of the unique epitope patterns; otherwise a lower case letter is used. The collapse_epitopes step takes as input the epitopes and columns files. This step also integrates an ordered list of epitope names that specify the processing order for epitopes to be added to the mosaic template sequence. This subsequently generates a FASTA formatted mosaic template sequence named "_collapsed_". The merge_seqs step replaces gap characters in the mosaic template sequence with the corresponding residue from the backbone sequence.

4. SMARt Dominant: For each epitope the unique sequences are ordered by their dominance as determined by the number of naturally occurring strains represented by that sequence. Dominant sequences for each epitope are selected and grafted onto a backbone in decreasing order of dominance (i.e. most dominant epitope patterns, then the second most dominant patterns, and so on). The SMARt Dominant approach generates polyvalent B-cell vaccine proteins using the occurrence frequency of unique epitope sequences to generate the mosaic sequences. In this approach, the unique epitope sequences for each epitope are ordered by frequency in the alignment. For M vaccine proteins, the top M unique epitope sequences for each epitope site are included in the mosaic pattern.

Figure 5:
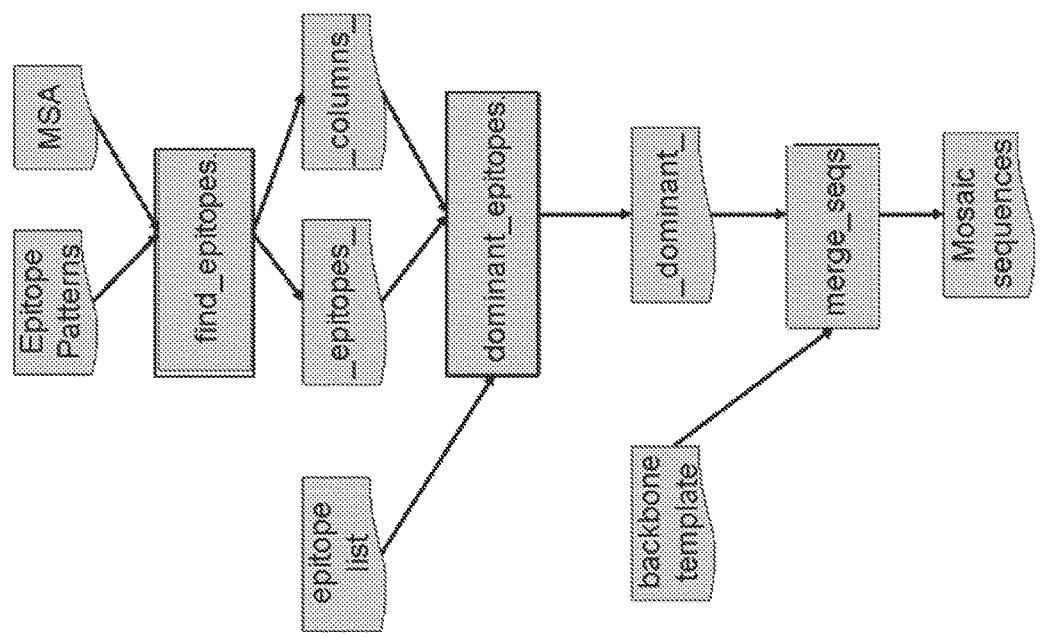
FIG. 5 shows an exemplary flowchart for the design and production of engineered antigenic polypeptides using the dominant epitopes process.

The dominant epitopes mosaic sequences approach generates a set of mosaic patterns by taking the occurrence frequency ordered epitope sequences for layering into the mosaic sequence templates. The data flow and method steps are overviewed in FIG. 5. The step "dominant_epitopes" takes as input the epitopes and columns files generated at the "find_epitopes_msa" step. An additional input specifies the ordered list of epitope names for the processing order of epitopes to be added to the mosaic template sequences. This approach generates a FASTA formatted mosaic template file named "_dominant_".

Embodiments of the present invention are based on the application of a methodology for the generation of mosaic B cell epitope sequences through structural mapping of antigenic repertoires. Vaccines developed to target specific viral isolates may not protect against infection from different isolates of the same virus. The approach for developing broadly protective antigens of the present invention, in some embodiments, creates polyvalent mosaic sequences that include B cell epitopes from as many viral isolates as possible. The individual sequences of known neutralizing antibody epitopes and antigenic sites are recombined to generate mosaic antigens. The best mosaic sequence templates are selected by evaluating overall alignment coverage by geographic regions, viral isolate years, sequence clusters or other scoring methods. The selected set of mosaic template patterns are combined with target backbone sequences to generate a set of full-length mosaic protein antigens. In some embodiments, structure refinement of these mosaic sequences yields the final set of vaccination proteins.

In some embodiments, the present invention is based on combinations of neutralizing and non-neutralizing hemagglutinin B cell epitope sequences derived from multiple influenza strains to generate novel mosaic designs for influenza hemagglutinin. Each design, consisting of a mosaic pattern of B-cell epitopes, is combined with a backbone hemagglutinin sequence. Other hemagglutinin backbone sequences may also be employed for construction of engineered HA polypeptides according to the present invention. In some embodiments, a backbone sequence provides the inter-epitope sequence as well as the signal peptide and transmembrane domains required for full-length hemagglutinin molecules that are expressed and functional.

In general, known neutralizing and non-neutralizing hemagglutinin B-cell epitopes described for any influenza strain are mapped to corresponding regions of the HA backbone. Individual sequences (antigenic repertoires) for each B cell epitopes are extracted and enumerated from the sequences of all available circulating influenza B strains. Distinct workflows, as described above, have been developed to combine the antigenic repertoires into novel mosaic hemagglutinin molecules that are distinct from natural circulating strains.

Exemplary workflows are further described in the Examples below. Although influenza hemagglutinin (HA) polypeptides are used as examples to illustrate methods described herein, the present invention may be used to engineer neuraminidase (NA) polypeptides and other immunogenic polypeptides or therapeutic biologics.

Exemplary Provided Engineered HA Polypeptides

The approaches described herein provide for the construction of novel hemagglutinin molecules for the H1N1 subtype that do not match naturally occurring strains. In some embodiments, these novel sequences are designed to provide broader coverage to naturally occurring strains than existing vaccine strains. The engineered full-length hemagglutinin sequences (including signal peptide and transmembrane domains) and derivatives are used as novel immunogens for inducing antibodies with broadened cross-reactivity across the H1 subtype of influenza. Full-length hemagglutinin sequences as described herein contain antigenic regions comprised of non-contiguous amino acid residues encompassing a receptor-binding site (RBS) and, in some embodiments, nearby residues within 5 Angstroms or within 10 Angstroms (Å). Exemplary engineered HA polypeptides of the present invention are shown in Table 1. Exemplary antigenic regions of engineered HA polypeptides of the present invention are shown in Table 2. Mosaic sequence patterns or consensus sequences that define over-lapping or non-overlapping epitopes or antigenic regions. Desired epitopes or antigenic regions may be linear or discontinuous based on 3D structures including, but not limited to, antigenic regions (e.g., Sa, Sb, Ca, Cb, etc.) and/or antibody binding sites.

In some embodiments, the epitope or antigenic region is all or part of the Receptor-Binding Site (RBS). As used herein, the term "receptor-binding site" or "RBS" comprises contiguous or non-contiguous amino acid residues of the head region of an influenza HA polypeptide, which include amino acids involved in direct binding of sialic acids on the target cell receptor proteins. The region of HA responsible for receptor binding resides at the membrane-distal tip of each monomer of the HA trimer, and it has several main structural features. For example, the binding site is flanked by the "220 and 130 loops", which contain amino acids that interact with sialic acid or internal sugars of the glycan chain. The membrane-distal region of the site is formed by the 190 helix, which also includes residues with the potential to contact the receptor at either the sialic acid (residue 194) or internal glycans on the receptor (approximately residues 190 and 193). The base of the site contains several highly conserved residues that form an extensive hydrogen bond network. Amino acid residues that make up a "receptor-binding site" or "RBS" of an influenza HA polypeptide may be described from a three-dimensional crystal structures of HA polypeptides complexed with sialic acid analogs and identifying amino acid residues within a certain proximity to the analog or may be described in reference to an HA polypeptide sequence from a particular viral strain (e.g., A/New Caledonia/20/99 or A/California/07/2009). Thus, in some embodiments, the "receptor-binding site" or "RBS" of an engineered HA polypeptide as described herein may be determined using a reference HA polypeptide sequence. In some embodiments, the "receptor-binding site" or "RBS" of an engineered HA polypeptide as described herein may be determined using the crystal structures of HA polypeptide sequence in complex with human and avian receptor analogs (ex. LSTa, LSTc). An exemplary reference crystal structure of HA polypeptide sequence in complex with LSTc includes A/Puerto Rico/8/1934 (H1N1) pdb11RVZ. In some embodiments, the RBS may be defined as the epitope bound by the broadly neutralizing monoclonal antibody CH65 (see, e.g., Whittle J R, et al. *Broadly neutralizing human antibody that recognizes the receptor-binding pocket of influenza virus hemagglutinin*. Proc Natl Acad Sci USA. 2011; 108:14216-21). Alternatively or additionally, the RBS may be defined as an area including all amino acid residues within 15 Angstroms of a universally conserved tryptophan corresponding to position 167 in (CA09 09 Numbering) (e.g. see Xu, R et al. Nat Struct Mol Biol. 2013 Mar; 20(3):363-70) or corresponding position on a influenza type B virus HA polypeptide.

In various embodiments, an engineered HA polypeptide as described herein comprises an antigenic region that comprises contiguous or non-contiguous amino acid residues associated with, adjacent to, and/or encompass a receptor-binding site (RBS). In some embodiments, the non-contiguous amino acid residues can be determined using the crystal structures of HA polypeptide.

Exemplary engineered HA polypeptides generated by the methods described herein are set forth in Table 1. A subset of engineered antigenic regions is set forth in Table 2.

TABLE 1

```
SP1    MKAKLLVLLCTFTATYADTICIGYHANNSTDTVDTVL
       EKNVTVTHSVNLLEDSHNGKLCKLKGIAPLQLGKCSV
       AGWILGNPECESLSTASSWSYIVETSNPENGTCYPGYF
       ADYEELREQLSSVSSFERFEIFPKESSWPNHTVTGVTAS
       CSHAGKSSFYRNLLWLTGKNGSYPNLSKSYVNNKEKE
       VLVLWGVHHPSNIGDQQTLYQTENAYVSVVSSRYSRR
       FTPEIAKRPKVRDQEGRMNYYWTLVEPGDTIIFEANGN
       LIAPWYAFALSRGFGSGIITSNAPVHDCNTKCQTPQGAI
       NSSLPFQNVHPVTIGECPKYVRSAKLRMATGLRNIPSIQ
       SRGLFGAIAGFIEGGWTGMVDGWYGYHHQNEQGSGY
       AADQKSTQNAIDGITNKVNSVIEKMNTQFTAVGKEFN
       KLERRMENLNKKVDDGFLDIWTYNAELLVLLENERTL
       DFHDSNVKNLYEKVKSQLKNNAKEIGNGCFEFYHKCN
       NTCMESVKNGTYDYPKYSEESKLNREKIDGVKLESMG
       VYQILAIYSTVASSLVLLVSLGAISFWMCSNGSLQCRIC
       I
       (SEQ ID NO: 1)

SP2    MKAKLLVLLCTFTATYADTICIGYHANNSTDTVDTVL
       EKNVTVTHSVNLLEDSHNGKLCKLKGIAPLQLGNCSV
       AGWILGNPECELLSTKSSWSYIVETPNPENGTCYPGYF
       ADYEELREQLSSVSSFERFEIFPKESSWPNHDVTGVSAS
       CSHNGASSFYRNLLWLTKKNNLYPNLSKSYANNKGKE
       VLVLWGVHHPSTIADQQTLYHTENAYVSVVSSHYSRR
       FTPEIAIRPKVRDQEGRINYYWTLLEPGDTIIFEANGNLI
       APWYAFALSRGFGSGIITSNAPMDECNTTCQTPQGAIN
       SSLPFQNVHPVTIGECPKYVRSAKLRMVTGLRNIPSIQS
       RGLFGAIAGFIEGGWTGMVDGWYGYHHQNEQGSGYA
       ADLKSTQNAINGITNKVNSVIEKMNTQFTAVGKEFNKL
       ERRMENLNKKVDDGFLDIWTYNAELLVLLENERTLDF
       HDSNVKNLYEKVKSQLKNNAKEIGNGCFEFYHKCNNE
       CMESVKNGTYDYPKYSEESKLNREKIDGVKLESMGVY
       QILAIYSTVASSLVLLVSLGAISFWMCSNGSLQCRICI
       (SEQ ID NO: 2)

SP3    MKAKLLVLLCTFTATYADTICIGYHANNSTDTVDTVL
       EKNVTVTHSVNLLEDSHNGKLCKLKGIAPLQLGKCSV
       AGWILGNPECESLSTASSWSYIVETSSPDNGTCYPGYF
       ADYEELREQLSSVSSFERFEIFPKTSSWPNHDSNGVTAS
       CPHAGAKSFYRNLLWLVKKGNSYPKLSKSYINDKGKE
       VLVLWGVHHPSTADQQSLYQNANAYVSVVTSRYSR
       RFTPEIAIRPKVRDQEGRMNYYWTLVEPGDTIIFEATG
       NLIAPWYAFALSRGFGSGIITSDTPVHDCNTTCQTPQG
       AINSSLPFQNVHPVTIGECPKYVRSAKLRMATGLRNIPS
       IQSRGLFGAIAGFIEGGWTGMVDGWYGYHHQNEQGS
       GYAADLKSTQNAIDGITNKVNSVIEKMNTQFTAVGKE
       FNKLERRMENLNKKVDDGFLDIWTYNAELLVLLENER
       TLDFHDSNVKNLYEKVKSQLKNNAKEIGNGCFEFYHK
       CNNTCMESVKNGTYDYPKYSEESKLNREKIDGVKLES
       MGVYQILAIYSTVASSLVLLVSLGAISFWMCSNGSLQC
       RICI
       (SEQ ID NO: 3)

SP4    MKAKLLVLLCTFTATYADTICIGYHANNSTDTVDTVL
       EKNVTVTHSVNILEDSHNGKLCLLKGIAPLQLGNCSVA
       GWILGNPECELLISKESWSYIVEKPNPENGTCYPGYFA
       DYEELREQLSSVSSFERFEIFPKESSWPNHTVTGVSASC
       SHNGKSSFYRNLLWLTGKNGLYPNLSKSYANNKEKEV
       LVLWGVHHPPNIGDQRALYHTENAYVSVVSSHYSRRF
       TPEIAKRPKVRDQEGRINYYWTLLEPGDTIIFEANGNLI
       APWYAFALSRGFGSGIITSNAPMDKCDAKCQTPQGAIN
       SSLPFQNVHPVTIGECPKYVRSAKLRMATGLRNIPFIQS
       RGLFGAIAGFIEGGWTGMVDGWYGYHHQNEQGSGYA
       ADQKSTQNAINGITNKVNSVIEKMNTQFTAVGKEFNK
       LERRMENLNKKVDDGFLDIWTYNAELLVLLENERTLD
       PHDSNVKNLYEKVKSQLKNNAKEIGNGCFEFYHKCND
       ECMESVKNGTYDYPKYSEESKLNREKIDGVKLESMGV
       YQILAIYSTVASSLVLLVSLGAISFWMCSNGSLQCRICI
       (SEQ ID NO: 4)

SP5    MKAKLLVLLCTFTATYADTICIGYHANNSTDTVDTVL
       EKNVTVTHSVNILEDSHNGKLCLLKGIAPLQLGNCSVA
       GWILGNPECELLISKESWSYIVEKPNPENGTCYPGYFA
       DYEELREQLSSVSSFERFEIFPKESSWPNHTVTGVSASC
       PHNGESSFYRNLLWLTGKNGLYPNLSKSYANNKEKEV
```

TABLE 1-continued

```
       LVLWGVHHPPNIGDQKTLYHTENAYVSVVSSHYSRRF
       TPEIAKRPKVRDQEGRINYYWTLLEPGDTIIFEANGNLI
       APWYAFALSRGFGSGIITSNAPMDKCDAKCQTPQGAIN
       SSLPFQNVHPVTIGECPKYVRSAKLRMATGLRNIQSIQS
       RGLFGAIAGFIEGGWTGMVDGWYGYHHQNEQGSGYA
       ADLKSTQNAINGITNKVNSVIEKMNTQFTAVGKEFNKL
       ERRMENLNKKVDDGFLDIWTYNAELLVLLENERTLDF
       HDSNVKNLYEKVKSQLKNNAKEIGNGCFEFYHKCNNT
       CMESVKNGTYDYPKYSEESKLNREKIDGVKLESMGVY
       QILAIYSTVASSLVLLVSLGAISFWMCSNGSLQCRICI
       (SEQ ID NO: 5)

SP6    MKAILVVLLYTFATANADTLCIGYHANNSTDTVDTVL
       EKNVTVTHSVNLLEDKHNGKLCKLRGVAPLHLGKCNI
       AGWILGNPECESLSTASSWSYIVETSNSENGTCYPGDFI
       DYEELREQLSSVSSFERFEIFPKESSWPNHTVTKGVTAA
       CSHAGKSSFYKNLIWLTGKNGSYPNLSKSYVNNKEKE
       VLVLWGIHHPSNIGDQQTLYQTEDTYVFVGSSRYSKKF
       KPEIAKRPKVRDQEGRMNYYWTLVEPGDKITFEANGN
       LVVPRYAFAMERNAGSGIIISNAPVHDCNTKCQTPKGA
       INTSLPFQNIHPITIGKCPKYVKSTKLRLATGLRNIPSIQS
       RGLFGAIAGFIEGGWTGMVDGWYGYHHQNEQGSGYA
       ADQKSTQNAIDEITNKVNSVIEKMNTQFTAVGKEFNHL
       EKRIENLNKKVDDGFLDIWTYNAELLVLLENERTLDY
       HDSNVKNLYEKVRSQLKNNAKEIGNGCFEFYHKCDNT
       CMESVKNGTYDYPKYSEEAKLNREEIDGVKLESTRIYQ
       ILAIYSTVASSLVLVVSLGAISFWMCSNGSLQCRICI
       (SEQ ID NO: 6)

SP7    MKAILVVLLYTFATANADTLCIGYHANNSTDTVDTVL
       EKNVTVTHSVNLLEDKHNGKLCLLRGVAPLHLGNCNI
       AGWILGNPECELLSTKSSWSYIVETPNSENGTCYPGDFI
       DYEELREQLSSVSSFERFEIFPKESSWPNHDVTKGVSA
       ACSHNGASSFYKNLIWLTKKNNLYPNLSKSYANNKGK
       EVLVLWGIHHPSTIADQQTLYHTEDTYVFVGSSHYSKK
       FKPEIAIRPKVRDQEGRINYYWTLLEPGDKITFEANGNL
       VVPRYAFAMERNAGSGIIISNAPMDECNTTCQTPKGAI
       NTSLPFQNIHPITIGKCPKYVKSTKLRLVTGLRNIPSIQS
       RGLFGAIAGFIEGGWTGMVDGWYGYHHQNEQGSGYA
       ADLKSTQNAINEITNKVNSVIEKMNTQFTAVGKEFNHL
       EKRIENLNKKVDDGFLDIWTYNAELLVLLENERTLDY
       HDSNVKNLYEKVRSQLKNNAKEIGNGCFEFYHKCDNE
       CMESVKNGTYDYPKYSEEAKLNREEIDGVKLESTRIYQ
       ILAIYSTVASSLVLVVSLGAISFWMCSNGSLQCRICI
       (SEQ ID NO: 7)

SP8    MKAILVVLLYTFATANADTLCIGYHANNSTDTVDTVL
       EKNVTVTHSVNLLEDKHNGKLCKLRGVAPLHLGKCNI
       AGWILGNPECESLSTASSWSYIVETSSSDNGTCYPGDFI
       DYEELREQLSSVSSFERFEIFPKTSSWPNHDSNKGVTA
       ACPHAGAKSFYKNLIWLVKKGNSYPKLSKSYINDKGK
       EVLVLWGIHHPSTSADQQSLYQNADTYVFVGTSRYSK
       KFKPEIAIRPKVRDQEGRMNYYWTLVEPGDKITFEATG
       NLVVPRYAFAMERNAGSGIIISDTPVHDCNTTCQTPKG
       AINTSLPFQNIHPITIGKCPKYVKSTKLRLATGLRNIPSIQ
       SRGLFGAIAGFIEGGWTGMVDGWYGYHHQNEQGSGYA
       AADLKSTQNAIDEITNKVNSVIEKMNTQFTAVGKEFNH
       LEKRIENLNKKVDDGFLDIWTYNAELLVLLENERTLD
       YHDSNVKNLYEKVRSQLKNNAKEIGNGCFEFYHKCD
       NTCMESVKNGTYDYPKYSEEAKLNREEIDGVKLESTRI
       YQILAIYSTVASSLVLVVSLGAISFWMCSNGSLQCRICI
       (SEQ ID NO: 8)

SP9    MKAILVVLLYTFATANADTLCIGYHANNSTDTVDTVL
       EKNVTVTHSVNILEDKHNGKLCLLRGVAPLHLGNCNI
       AGWILGNPECELLISKESWSYIVEKPNSENGTCYPGDFI
       DYEELREQLSSVSSFERFEIFPKESSWPNHTVTKGVSAA
       CSHNGKSSFYKNLIWLTGKNGLYPNLSKSYANNKEKE
       VLVLWGIHHPPNIGDQRALYHTEDTYVFVGSSHYSKK
       FKPEIAKRPKVRDQEGRINYYWTLLEPGDKITFEANGN
       LVVPRYAFAMERNAGSGIIISNAPMDKCDAKCQTPKG
       AINTSLPFQNIHPITIGKCPKYVKSTKLRLVTGLRNIPFIQ
       SRGLFGAIAGFIEGGWTGMVDGWYGYHHQNEQGSGY
       AADQKSTQNAINEITNKVNSVIEKMNTQFTAVGKEFN
       HLEKRIENLNKKVDDGFLDIWTYNAELLVLLENERTL
       DYDSNVKNLYEKVRSQLKNNAKEIGNGCFEFYHKC
       DDECMESVKNGTYDYPKYSEEAKLNREEIDGVKLEST
       RIYQILAIYSTVASSLVLVVSLGAISFWMCSNGSLQCRI
       CI
       (SEQ ID NO: 9)
```

TABLE 1-continued

SP10　MKAILVVLLYTFATANADTLCIGYHANNSTDTVDTVL
EKNVTVTHSVNILEDKHNGKLCLLRGVAPLHLGNCNI
AGWILGNPECELLISKESWSYIVEKPNSENGTCYPGDFI
DYEELREQLSSVSSFERFEIFPKESSWPNHTVTKGVSAA
CPHNGESSFYKNLIWLTGKNGLYPNLSKSYANNKEKE
VLVLWGIHHPPNIGDQKTLYHTEDTYVFVGSSHYSKK
FKPEIAKRPKVRDQEGRINYYWTLLEPGDKITFEANGN
LVVPRYAFAMERNAGSGIIISNAPMDKCDAKCQTPKG
AINTSLPFQNIHPITIGKCPKYVKSTKLRLATGLRNIQSI
QSRGLFGAIAGFIEGGWTGMVDGWYGYHHQNEQSG
YAADLKSTQNAINEITNKVNSVIEKMNTQFTAVGKEFN
HLEKRIENLNKKVDDGFLDIWTYNAELLVLLENERTL
DYHDSNVKNLYEKVRSQLKNNAKEIGNGCFEFYHKC
DNTCMESVKNGTYDYPKYSEEAKLNREEIDGVKLEST
RIYQILAIYSTVASSLVLVVSLGAISFWMCSNGSLQCRI
CI
(SEQ ID NO: 10)

TABLE 2

| Engineered HA | Antigenic Region Sequence |
|---|---|
| SP1 | GVTASSWLTHHPSNGDQQTLKDQEGR (SEQ ID NO: 11) |
| SP2 | GVSASSWLTHHPSTADQQTLKDQEGR (SEQ ID NO: 12) |
| SP3 | GVTASKWLVHHPSTADQQSLKDQEGR (SEQ ID NO: 13) |
| SP4 | GVSASSWLTHHPPNGDQRALKDQEGR (SEQ ID NO: 14) |
| SP5 | GVSASSWLTHHPPNGDQKTLKDQEGR (SEQ ID NO: 15) |
| SP7 | GVSAASWLTHHPSTADQQTLKDQEGR (SEQ ID NO: 16) |
| SP8 | GVTAAKWLVHHPSTADQQSLKDQEGR (SEQ ID NO: 17) |
| SP9 | GVSAASWLTHHPPNGDQRALKDQEGR (SEQ ID NO: 18) |
| SP10 | GVSAASWLTHHPPNGDQKTLKDQEGR (SEQ ID NO: 19) |
| SP1 | CYPTVTGVTASCSKSSFLWLTGVHHPSNIGDQQTLYQEIAKRPKVRDQEGRMNI (SEQ ID NO: 20) |
| SP2 | CYPDVTGVSASCSASSFLWLTKVHHPSTIADQQTLYHEIAIRPKVRDQEGRINI (SEQ ID NO: 21) |
| SP3 | CYPDSNGVTASCPAKSFLWLVKVHHPSTSADQQSLYQEIAIRPKVRDQEGRMNI (SEQ ID NO: 22) |
| SP4 | CYPTVTGVSASCSKSSFLWLTGVHHPPNIGDQRALYHEIAKRPKVRDQEGRINI (SEQ ID NO: 23) |
| SP5 | CYPTVTGVSASCPESSFLWLTGVHHPPNIGDQKTLYHEIAKRPKVRDQEGRTNT (SEQ ID NO: 24) |
| SP6 | CYPTVTKGVTAACSKSSFIWLTGIHHPSNIGDQQTLYQEIAKRPKVRDQEGRMNV (SEQ ID NO: 25) |
| SP7 | CYPDVTKGVSAACSASSFIWLTKIHHPSTIADQQTLYHEIAIRPKVRDQEGRINV (SEQ ID NO: 26) |
| SP8 | CYPDSNKGVTAACPAKSFIWLVKIHHPSTSADQQSLYQEIAIRPKVRDQEGRMNV (SEQ ID NO: 27) |
| SP9 | CYPTVTKGVSAACSKSSFIWLTGIHHPPNIGDQRALYHEIAKRPKVRDQEGRINV (SEQ ID NO: 28) |
| SP10 | CYPTVTKGVSAACPESSFIWLTGIHHPPNIGDQKTLYHEIAKRPKVRDQEGRINV (SEQ ID NO: 29) |
| SP1 | LGNPGTCYPGYKWNHTVTGVTASCSHAGKSSFYRNLLWLTGKNGSYPWGVHHPSNIGDQQTLYQTENAFTPEIAKRPKVRDQEGRMNYANGNLIAPW (SEQ ID NO: 30) |
| SP2 | LGNPGTCYPGYKWNHDVTGVSASCSHNGASSFYRNLLWLTKKNNLYPWGVHHPSTIADQQTLYHTENAFTPEIAIRPKVRDQEGRINYANGNLIAPW (SEQ ID NO: 31) |
| SP3 | LGNPGTCYPGYKWNHDSNGVTASCPHAGAKSFYRNLLWLVKKGNSYPWGVHHPSTSADQQSLYQNANAFTPEIAIRPKVRDQEGRMNYATGNLIAPW (SEQ ID NO: 32) |
| SP4 | LGNPGTCYPGYKWNHTVTGVSASCSHNGKSSFYRNLLWLTGKNGLYPWGVHHPPNIGDQRALYHTENAFTPEIAKRPKVRDQEGRINYANGNLIAPW (SEQ ID NO: 33) |
| SP5 | LGNPGTCYPGYKWNHTVTGVSASCPHNGESSFYRNLLWLTGKNGLYPWGVHHPPNIGDQKTLYHTENAFTPEIAKRPKVRDQEGRINYANGNLIAPW (SEQ ID NO: 34) |
| SP6 | LGNPGTCYPGDKWNHTVTKGVTAACSHAGKSSFYKNLIWLTGKNGSYPWGIHHPSNIGDQQTLYQTEDTFKPEIAKRPKVRDQEGRMNYANGNLVVPR (SEQ ID NO: 35) |
| SP7 | LGNPGTCYPGDKWNHDVTKGVSAACSHNGASSFYKNLIWLTKKNNLYPWGIHHPSTIADQQTLYHTEDTFKPEIAIRPKVRDQEGRINYANGNLVVPR (SEQ ID NO: 36) |
| SP8 | LGNPGTCYPGDKWNHDSNKGVTAACPHAGAKSFYKNLIWLVKKGNSYPWGIHHPSTSADQQSLYQNADTFKPEIAIRPKVRDQEGRMNYATGNLVVPR (SEQ ID NO: 37) |
| SP9 | LGNPGTCYPGDKWNHTVTKGVSAACSHNGKSSFYKNLIWLTGKNGLYPWGIHHPPNIGDQRALYHTEDTFKPEIAKRPKVRDQEGRINYANGNLVVPR (SEQ ID NO: 38) |
| SP10 | LGNPGTCYPGDKWNHTVTKGVSAACPHNGESSFYKNLIWLTGKNGLYPWGIHHPPNIGDQKTLYHTEDTFKPEIAKRPKVRDQEGRINYANGNLVVPR (SEQ ID NO: 39) |

In various embodiments, engineered HA polypeptides of the present invention are composed of combinations of epitope patterns observed in hemagglutinin sequences. In some embodiments, the epitopes present in engineered HA polypeptides of the present invention include antibody binding sites which may or may not be restricted to a single serotype. In many embodiments, engineered HA polypeptides are selected from Table 1.

In various embodiments, engineered HA polypeptides as described herein comprise combinations of epitope patterns on a particular viral backbone sequence. As will be appreciated by persons of skill, multiple epitopes can be assembled on to any viral backbone as desired. Exemplary viral backbone sequences include A/New Caledonia/20/1999, A/California/07/2009, and a consensus (e.g., 1918-2011) sequence. In some embodiments, engineered HA polypeptides as described herein comprise a New Caledonia 99 or California 09 backbone sequence.

In some embodiments, an engineered HA polypeptide of the present invention has a sequence at least about 90% (e.g., at least about 91%, 92%, 93%, 94%, 95%, 96%, 97%, 98% or 99%) identical to a sequence that appears in Table 1.

In some embodiments, an engineered HA polypeptide of the present invention has a sequence that is substantially identical to a sequence that appears in Table 1.

In some embodiments, an engineered HA polypeptide of the present invention has a sequence that is identical to a sequence that appears in Table 1.

In some embodiments, an engineered HA polypeptide of the present invention is selected from a sequence that appears in Table 1.

In some embodiments, an engineered HA polypeptide of the present invention has a sequence at least about 95% (e.g., at least about 96%, 97%, 98% or 99%) identical to a sequence that appears in Table 1, wherein the sequence is not a naturally-occurring sequence. In some embodiments, an engineered HA polypeptide of the present invention has a sequence at least about 95% (e.g., at least about 96%, 97%, 98% or 99%) identical to a sequence that appears in Table 1.

In some embodiments, mosaic antigens as described herein are refined by molecular modeling to resolve structural problems and generate energy-minimized designs for engineered HA polypeptides. The total energies of the resulting designed molecules are calculated using a design algorithm. For example, the design algorithm in the Rosetta molecular modeling software version 3.1 (Simons et al., 1997, J. Mol. Biol. 268:209-225; Leaver-Fay et al., 2011, Methods Enzymol. 487:545-574) may be used. Molecules with negative total energy scores are predicted to have a good probability of folding into stable proteins while those with positive energy scores are considered less likely to fold properly. In addition to the total energy scores, per-residue energy scores for each molecule are evaluated in order to identify hot-spots (i.e., specific amino acid residues in the designed structures that had positive energy scores). Such hot spots may induce local misfolding with negative impact on epitope presentation on the surface of the molecule. The modeled structures are carefully examined visually to determine the location of the hot-spot residues relative to the surface of the molecule. In some embodiments, to further stabilize the molecular designs, high-energy residues situated outside of important epitope regions are substituted to more stable alternatives compatible with the local structural context. The resulting designs are more stable than the initial versions as determined by recalculated total energy scores.

In various embodiments, an engineered HA polypeptide as described herein comprises an antigenic region (see, e.g., Table 2) that comprises contiguous or non-contiguous amino acid residues associated with, adjacent to, and/or encompass a receptor-binding site (RBS). In some embodiments, the non-contiguous amino acid residues can be determined using the crystal structures of HA polypeptide sequence in complex with human and avian receptor analogs (ex. LSTa, LSTc). An exemplary reference crystal structure of HA polypeptide sequence in complex with LSTc includes A/Puerto Rico/8/1934 (H1N1) pdb||1RVZ.

In some embodiments, an engineered HA polypeptide of the present invention comprises an antigenic region that comprises amino acid residues 148, 149, 150, 151, 152, 159, 167, 168, 169, 197, 198, 199, 200, 201, 203, 204, 205, 206, 207, 208, 236, 239, 240, 241, 242, 243, or a subset thereof (e.g., with at least 70%, 75%, 80%, 85%, 90%, or 95% of the referenced residues), as indexed by reference to an A/California/07/2009 HA amino acid sequence.

In some embodiments, an engineered HA polypeptide of the present invention comprises an antigenic region that comprises amino acid residues 107, 108, 109, 144, 145, 146, 147, 148, 149, 150, 151, 152, 153, 154, 158, 159, 160, 161, 166, 167, 168, 169, 170, 196, 197, 198, 199, 200, 201, 202, 203, 204, 205, 206, 207, 208, 209, 210, 230, 231, 232, 233, 234, 235, 236, 237, 238, 239, 240, 241, 242, 243, 244, 264, 266, or a subset thereof (e.g., with at least 70%, 75%, 80%, 85%, 90%, or 95% of the referenced residues), as indexed by reference to an A/California/07/2009 HA amino acid sequence.

In some embodiments, an engineered HA polypeptide of the present invention comprises an antigenic region that comprise amino acid residues 79, 80, 81, 82, 105, 106, 107, 108, 109, 110, 111, 136, 140, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 194, 195, 196, 197, 198, 199, 200, 201, 202, 203, 204, 205, 206, 207, 208, 209, 210, 211, 212, 213, 214, 227, 228, 229, 230, 231, 232, 233, 234, 235, 236, 237, 238, 239, 240, 241, 242, 243, 244, 245, 246, 261, 262, 263, 264, 265, 266, 267, 268, 269, or a subset thereof (e.g., with at least 70%, 75%, 80%, 85%, 90%, or 95% of the referenced residues), as indexed by reference to an A/California/07/2009 HA amino acid sequence.

In some embodiments, an engineered HA polypeptide of the present invention comprises an antigenic region that comprises amino acid residues 148, 149, 150, 151, 152, 159, 167, 168, 169, 197, 198, 199, 200, 201, 203, 204, 205, 206, 207, 208, 236, 239, 240, 241, 242 and 243 as indexed by reference to an A/California/07/2009 HA amino acid sequence, wherein the linear amino acid sequence is at least 90% (e.g., 91%, 92%, 93%, 94%, 95%, 96%, 97%, 98%, 99% or more) identical to an antigenic region, or subset thereof, of any one of SEQ ID NOs: 11-19.

In some embodiments, an engineered HA polypeptide of the present invention comprises an antigenic region that comprises amino acid residues 148, 149, 150, 151, 152, 159, 167, 168, 169, 197, 198, 199, 200, 201, 203, 204, 205, 206, 207, 208, 236, 239, 240, 241, 242 and 243 as indexed by reference to an A/California/07/2009 HA amino acid sequence, wherein the linear amino acid sequence is substantially identical to an antigenic region, or subset thereof, of any one of SEQ ID NOs: 11-19.

In some embodiments, an engineered HA polypeptide of the present invention comprises an antigenic region that comprises amino acid residues 148, 149, 150, 151, 152, 159, 167, 168, 169, 197, 198, 199, 200, 201, 203, 204, 205, 206, 207, 208, 236, 239, 240, 241, 242 and 243 as indexed by reference to an A/California/07/2009 HA amino acid sequence, wherein the linear amino acid sequence is identical to an antigenic region, or subset thereof, of any one of SEQ ID NOs: 11-19.

In some embodiments, an engineered HA polypeptide of the present invention comprises an antigenic region that comprises amino acid residues 107, 108, 109, 144, 145, 146, 147, 148, 149, 150, 151, 152, 153, 154, 158, 159, 160, 161, 166, 167, 168, 169, 170, 196, 197, 198, 199, 200, 201, 202, 203, 204, 205, 206, 207, 208, 209, 210, 230, 231, 232, 233, 234, 235, 236, 237, 238, 239, 240, 241, 242, 243, 244, 264 and 266 as indexed by reference to an A/California/07/2009 HA amino acid sequence, wherein the linear amino acid sequence is at least 90% (e.g., 91%, 92%, 93%, 94%, 95%, 96%, 97%, 98%, 99% or more) identical to an antigenic region, or a subset thereof, of any one of SEQ ID NOs:20-29.

In some embodiments, an engineered HA polypeptide of the present invention comprises an antigenic region that comprises amino acid residues 107, 108, 109, 144, 145, 146, 147, 148, 149, 150, 151, 152, 153, 154, 158, 159, 160, 161, 166, 167, 168, 169, 170, 196, 197, 198, 199, 200, 201, 202, 203, 204, 205, 206, 207, 208, 209, 210, 230, 231, 232, 233, 234, 235, 236, 237, 238, 239, 240, 241, 242, 243, 244, 264 and 266 as indexed by reference to an A/California/07/2009 HA amino acid sequence, wherein the linear amino acid sequence is substantially identical to an antigenic region, or subset thereof, of any one of SEQ ID NOs:20-29.

In some embodiments, an engineered HA polypeptide of the present invention comprises an antigenic region that comprises amino acid residues 107, 108, 109, 144, 145, 146, 147, 148, 149, 150, 151, 152, 153, 154, 158, 159, 160, 161, 166, 167, 168, 169, 170, 196, 197, 198, 199, 200, 201, 202, 203, 204, 205, 206, 207, 208, 209, 210, 230, 231, 232, 233, 234, 235, 236, 237, 238, 239, 240, 241, 242, 243, 244, 264 and 266 as indexed by reference to an A/California/07/2009 HA amino acid sequence, wherein the linear amino acid sequence is identical to an antigenic region, or subset thereof, of any one of SEQ ID NOs:20-29.

In some embodiments, an engineered HA polypeptide of the present invention comprises an antigenic region that comprise amino acid residues 79, 80, 81, 82, 105, 106, 107, 108, 109, 110, 111, 136, 140, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 194, 195, 196, 197, 198, 199, 200, 201, 202, 203, 204, 205, 206, 207, 208, 209, 210, 211, 212, 213, 214, 227, 228, 229, 230, 231, 232, 233, 234, 235, 236, 237, 238, 239, 240, 241, 242, 243, 244, 245, 246, 261, 262, 263, 264, 265, 266, 267, 268 and 269 as indexed by reference to an A/California/07/2009 HA amino acid sequence, wherein the linear amino acid sequence is at least 90% (e.g., 91%, 92%, 93%, 94%, 95%, 96%, 97%, 98%, 99% or more) identical to an antigenic region, or subset thereof, of any one of SEQ ID NOs:30-39.

In some embodiments, an engineered HA polypeptide of the present invention comprises an antigenic region that comprise amino acid residues 79, 80, 81, 82, 105, 106, 107, 108, 109, 110, 111, 136, 140, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 194, 195, 196, 197, 198, 199, 200, 201, 202, 203, 204, 205, 206, 207, 208, 209, 210, 211, 212, 213, 214, 227, 228, 229, 230, 231, 232, 233, 234, 235, 236, 237, 238, 239, 240, 241, 242, 243, 244, 245, 246, 261, 262, 263, 264, 265, 266, 267, 268 and 269 as indexed by reference to an A/California/07/2009 HA amino acid sequence, wherein the linear amino acid sequence is substantially identical to an antigenic region, or subset thereof, of any one of SEQ ID NOs:30-39.

In some embodiments, an engineered HA polypeptide of the present invention comprises an antigenic region that comprises amino acid residues 79, 80, 81, 82, 105, 106, 107, 108, 109, 110, 111, 136, 140, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 194, 195, 196, 197, 198, 199, 200, 201, 202, 203, 204, 205, 206, 207, 208, 209, 210, 211, 212, 213, 214, 227, 228, 229, 230, 231, 232, 233, 234, 235, 236, 237, 238, 239, 240, 241, 242, 243, 244, 245, 246, 261, 262, 263, 264, 265, 266, 267, 268 and 269 as indexed by reference to an A/California/07/2009 HA amino acid sequence, wherein the linear amino acid sequence is identical to an antigenic region, or subset thereof, of any one of SEQ ID NOs:30-39.

In some embodiments, an engineered HA polypeptide of the present invention comprises an antigenic region that comprises a linear amino acid sequence, or subset thereof, that appears in Table 2.

Nucleic Acid Construction and Expression

Engineered influenza HA polypeptides as described herein may be produced from nucleic acid molecules using molecular biological methods known to the art. Nucleic acid molecules are inserted into a vector that is able to express the HA polypeptides when introduced into an appropriate host cell. Appropriate host cells include, but are not limited to, bacterial, yeast, insect, and mammalian cells. Any of the methods known to one skilled in the art for the insertion of DNA fragments into a vector may be used to construct expression vectors encoding the fusion proteins of the present invention under control of transcriptional/translational control signals. These methods may include in vitro recombinant DNA and synthetic techniques and in vivo recombination (See Sambrook et al. Molecular Cloning, A Laboratory Manual, Cold Spring Harbor Laboratory; Current Protocols in Molecular Biology, Eds. Ausubel, et al., Greene Publ. Assoc., Wiley-Interscience, NY).

In some embodiments, the present invention provides nucleic acids which encode an HA polypeptide or a characteristic or biologically active portion of an HA polypeptide. In some embodiments, the invention provides nucleic acids which are complementary to nucleic acids which encode an HA polypeptide or a characteristic or biologically active portion of an HA polypeptide.

In some embodiments, the invention provides nucleic acid molecules which hybridize to nucleic acids encoding an HA polypeptide or a characteristic or biologically active portion of an HA polypeptide. Such nucleic acids can be used, for example, as primers or as probes. To give but a few examples, such nucleic acids can be used as primers in polymerase chain reaction (PCR), as probes for hybridization (including in situ hybridization), and/or as primers for reverse transcription-PCR (RT-PCR).

In some embodiments, nucleic acids can be DNA or RNA, and can be single stranded or double-stranded. In some embodiments, nucleic acids in accordance with the invention may include one or more non-natural nucleotides; in some embodiments, nucleic acids in accordance with the invention include only natural nucleotides.

Expression of nucleic acid molecules in accordance with the present invention may be regulated by a second nucleic acid sequence so that the molecule is expressed in a host transformed with the recombinant DNA molecule. For example, expression of the nucleic acid molecules of the invention may be controlled by a promoter and/or enhancer element, which are known in the art.

Nucleic acid constructs of the present invention are inserted into an expression vector or viral vector by methods known to the art, and nucleic acid molecules are operatively linked to an expression control sequence.

An expression vector containing a nucleic acid molecule is transformed into a suitable host cell to allow for production of the protein encoded by the nucleic acid constructs. Exemplary host cells include prokaryotes (e.g., *E. coli*) and eukaryotes (e.g., a Vero, COS, 293 or CHO cell). Host cells transformed with an expression vector are grown under conditions permitting production of an engineered HA polypeptide the present invention followed by recovery of an engineered HA polypeptide.

Engineered HA polypeptides of the present invention may be purified by any technique known in the art. For example, not wishing to be bound by theory, engineered HA polypeptides may be recovered from cells either as soluble polypeptides or as inclusion bodies, from which they may be extracted quantitatively by 8M guanidinium hydrochloride and dialysis. In order to further purify engineered HA polypeptides of the present invention, conventional ion exchange chromatography, hydrophobic interaction chromatography, reverse phase chromatography or gel filtration may be used. Engineered HA polypeptides of the present invention may also be recovered from conditioned media following secretion from eukaryotic or prokaryotic cells.

Antibodies to Polypeptides

The present invention provides antibodies to HA polypeptides in accordance with the invention. These may be monoclonal or polyclonal and may be prepared by any of a variety of techniques known to those of ordinary skill in the art (e.g., see Harlow and Lane, 1988, Antibodies: A Laboratory Manual, Cold Spring Harbor Laboratory; incorporated herein by reference). For example, antibodies can be produced by cell culture techniques, including the generation of monoclonal antibodies, or via transfection of antibody genes into suitable bacterial or mammalian cell hosts, in order to allow for the production of recombinant antibodies.

Screening and Detection Methods

Engineered HA or NA polypeptides generated according to various methods described herein may be assessed for desired expression and conformation. Screening methods are known to the art and include cell-free, cell-based, and animal assays. In vitro assays can be either solid state or soluble target molecule detection may be achieved in a number of ways known to the art, including the use of a label or detectable group capable of identifying an engineered HA polypeptide which is bound to a target molecule (e.g., immunoglobulin). Detectable labels may be used in conjunction with assays using engineered HA or NA polypeptides of the present invention. For example, engineered HA or NA polypeptide as described herein may be evaluated and selected based on expression and conformational characteristics as determined by assays described in International Patent Application PCT/US2015/033205 entitled "Expression and Conformational Analysis of Engineered Influenza Hemagglutinin" filed on May 29, 2015.

Other binding assays may also be used to evaluate expression and conformation of engineered HA or NA polypeptides, including but not limited to, a Protein Expression and Purification Platform (PEPP) system or a Biolayer Interferometry (BLI) system. In some embodiments, expression and conformation of engineered HA or NA polypeptides may be measured and ranked by quantitating the level of monoclonal antibody binding.

The present invention also provides methods for testing engineered HA or NA polypeptides in accordance with the invention in an animal host. As used herein, an "animal host" includes any animal model suitable for influenza research. For example, animal hosts suitable for the invention can be any mammalian hosts, including primates, ferrets, cats, dogs, cows, horses, rodents such as, mice, hamsters, rabbits, and rats. In some embodiments, an animal host used for the invention is a ferret. In particular, in some embodiments, an animal host is naïve to viral exposure or infection prior to administration of a binding agent in accordance with the invention (optionally in a composition in accordance with the invention). In some embodiments, the animal host is inoculated with, infected with, or otherwise exposed to virus prior to or concurrent with administration of an engineered HA or NA polypeptide in accordance with the invention. An animal host used in the practice of the present invention can be inoculated with, infected with, or otherwise exposed to virus by any method known in the art. In some embodiments, an animal host may be inoculated with, infected with, or exposed to virus intranasally.

Naïve and/or inoculated animals may be used for any of a variety of studies. For example, such animal models may be used for hemagglutinin inhibition assays, microneutralization assays, challenge assays and virus transmission studies, as is known in the art. It is contemplated that the use of ferrets in virus transmission studies may serve as a reliable predictor for virus transmission in humans. For example, air transmission of viral influenza from inoculated animals (e.g., ferrets) to naïve animals is known in the art (Tumpey et al., 2007, Science 315; 655-59; incorporated herein by reference). Virus transmission studies may be used to test engineered HA polypeptides in accordance with the invention. For example, engineered HA polypeptides in accordance with the invention may be administered to a suitable animal host in order to determine the efficacy of said engineered HA polypeptide in eliciting a broad immune response in the animal host. Using information gathered from studies in an animal host, one may predict the efficacy of an engineered HA polypeptide to elicit broadly protective in a human host.

Influenza Virus-Like Particles (VLPs)

In some embodiments, the present invention provides for influenza virus-like particles (VLPs) including an engineered HA polypeptide as described herein (e.g., an HA polypeptide that appears in Table 1). The influenza VLPs are, in some embodiments, generally made up of HA, NA and virus structural (e.g., HIV gag) proteins. Production of influenza VLPs is known in the art and will be readily apparent to persons of skill upon reading the present disclosure. For example, influenza VLPs may be produced by transfection of host cells with plasmids encoding the HA, NA and HIV gag proteins. To give but one example, a suitable host cell includes a human cell (e.g., HEK293T). After incubation of the transfected cells for an appropriate time to allow for protein expression (such as for approximately 72 hours), VLPs may be isolated from cell culture supernatants. In some embodiments, influenza VLPs as disclosed herein may be used as influenza vaccines to elicit a broadly neutralizing immune response against H1N1 influenza viruses.

Pharmaceutical Compositions

In some embodiments, the present invention provides for pharmaceutical compositions including an engineered HA polypeptide as described herein and/or related entities. For example, in some embodiments, engineered HA polypeptides, nucleic acids encoding such polypeptides, characteristic or biologically active fragments of such polypeptides or nucleic acids, antibodies that bind to and/or compete with such polypeptides or fragments, small molecules that interact with or compete with such polypeptides or with glycans that bind to them, etc. are included in pharmaceutical compositions in accordance with the invention.

In some embodiments, the present invention provides methods of preventing or treating influenza infections by administration of such pharmaceutical compositions in accordance with the invention. In some embodiments, pharmaceutical compositions in accordance with the invention are administered to a subject suffering from or susceptible to an influenza infection. In some embodiments, a subject is an animal, including but not limited to birds (e.g., chickens, ducks, turkeys, etc.), dogs, horses and pigs. In some embodiments, a subject is considered to be suffering from an influenza infection in the subject is displaying one or more symptoms commonly associated with influenza infection. In some embodiments, the subject is known or believed to have been exposed to the influenza virus. In some embodiments, a subject is considered to be susceptible to an influenza infection if the subject is known or believed to have been exposed to the influenza virus. In some embodiments, a subject is known or believed to have been exposed to the influenza virus if the subject has been in contact with other individuals known or suspected to have been infected with the influenza virus and/or if the subject is or has been present in a location in which influenza infection is known or thought to be prevalent.

In some embodiments, subjects suffering from or susceptible to influenza infection are tested for antibodies to engineered HA polypeptides in accordance with the invention prior to, during, or after administration of pharmaceutical compositions in accordance with the invention. In some embodiments, subjects having such antibodies are not administered pharmaceutical compositions comprising engineered HA polypeptides in accordance with the invention. In some embodiments, an appropriate dose of pharmaceutical composition and/or engineered HA polypeptide is selected based on detection (or lack thereof) of such antibodies.

In some embodiments, selection of a particular subject for treatment, particular engineered HA polypeptide or composition for administration, and/or particular dose or regimen for administration, is memorialized, for example in a written, printed, or electronic storage form.

Compositions comprising an engineered HA polypeptide as described may be administered prior to or after development of one or more symptoms of influenza infection. In some embodiments, influenza VLPs comprising an engineered HA polypeptide as described herein (or an engineered HA polypeptide itself) may be administered prior to or after development of one or more symptoms of influenza infection.

In some embodiments, the present invention provides for treatment of influenza infections by administration of engineered HA polypeptides described herein. In some embodiments, treatment of influenza infections according to the present invention is accomplished by administration of an influenza VLP comprising an engineered HA polypeptide as described herein. In some embodiments, treatment of influenza infections according to the present invention is accomplished by administration of a vaccine. To date, although significant accomplishments have been made in the development of influenza vaccines, there is room for further improvement. The present invention provides vaccines comprising engineered HA polypeptides in accordance with the invention, and particularly comprising engineered HA polypeptides that elicit broadly protective immune responses to multiple neutralizing antigenic determinants (e.g., epitope) of the engineered HA polypeptides.

In some embodiments, the present invention provides an influenza VLP, an influenza vaccine, a fusion protein and/or an engineered HA polypeptide as described herein for influenza prophylactics.

In some embodiments, the present invention provides for immunogenic compositions (e.g., vaccines) and the administration of these immunogenic compositions to a human subject. In particular embodiments, a human subject is 6 months of age or older, is 6 months through 35 months of age, is 36 months through 8 years of age, or 9 years of age or older. In some embodiments, the immunogenic compositions are pharmaceutical compositions comprising one or more of the following: (1) inactivated virus, (2) live attenuated influenza virus, for example, replication-defective virus, (3) virus-like particles (VLPs), (4) engineered HA polypeptide, (5) nucleic acid encoding an engineered HA polypeptide or characteristic or biologically active portion thereof, (6) DNA vector that encodes an engineered HA polypeptide in accordance with the invention or characteristic or biologically active portion thereof, and/or (7) expression system, for example, cells expressing one or more influenza proteins to be used as antigens.

Thus, in some embodiments, the present invention provides inactivated flu vaccines. In some embodiments, inactivated flu vaccines comprise one of three types of antigen preparation: inactivated whole virus, sub-virions where purified virus particles are disrupted with detergents or other reagents to solubilize the lipid envelope ("split" vaccine) or purified HA polypeptide ("subunit" vaccine). In some embodiments, virus can be inactivated by treatment with formaldehyde, beta-propiolactone, ether, ether with detergent (such as TWEEN-80®), cetyl trimethyl ammonium bromide (CTAB) and Triton N101, sodium deoxycholate and tri(n-butyl) phosphate. Inactivation can occur after or prior to clarification of allantoic fluid (from virus produced in eggs); the virions are isolated and purified by centrifugation (Nicholson et al., eds., 1998, Textbook of Influenza, Blackwell Science, Malden, M A; incorporated herein by reference). To assess the potency of the vaccine, the single radial immunodiffusion (SRD) test can be used (Schild et al., 1975, Bull. World Health Organ., 52:43-50 & 223-31; Mostow et al., 1975, J. Clin. Microbiol., 2:531; both of which are incorporated herein by reference).

In some embodiments, engineered HA polypeptides of the present invention are used as a component of seasonal and/or pandemic influenza vaccines or as part of an influenza vaccination regimen intended to confer long-lasting (multi-season) protection. The nucleic acid sequences encoding the engineered influenza HA polypeptides obtained by the methods described herein can be combined with one or more donor viruses and used in a reverse genetics system to produce an infectious reassortant influenza virus. Reverse genetics systems can be used produce infectious, reassortant viruses, or attenuated viruses from their cDNAs. The reverse genetics methods are well-known by the one skilled in the art and include, but are not limited to, the methods using the plasmids described in Neuman et al, 1999, Proc Natl Acad Sci USA, 96(16):9345-9350; Neumann et al, 2005, Proc Natl Acad Sci USA, 102(46): 16825-16829; Zhang et al, 2009, J Virol, 83(18):9296-9303; Massin et al, 2005, J Virol, 79(21):13811-13816; Murakami et al, 2008, 82(3):1605-1609; and/or the cells described in Neuman et al, 1999, Proc Natl Acad Sci USA, 96(16):9345-9350; Neumann et al, 2005, Proc Natl Acad Sci USA, 102(46): 16825-16829; Zhang et al, 2009, J Virol, 83(18): 9296-9303; Massin et al, 2005, J Virol, 79(21):1381 1-13816; Murakami et al, 2008, 82(3):1605-1609; Koudstaal et al, 2009, Vaccine, 27(19):2588-2593; Schickli et al, 2001, Philos Trans R Soc Lond Biol Sci, 356(1416):1965-1973; Nicolson et al, 2005, Vaccine, 23(22):2943-2952; Legastelois et al, 2007, Influenza Other Respi Viruses, 1 (3):95-104; Whiteley et al, 2007, Influenza Other Respi Viruses, 1 (4): 157-166.

In certain embodiments, the reverse genetics method may be:

(i) the 16 plasmid method, such as the method described by Neuman et al, 1999, Proc Natl Acad Sci USA, 96(16): 9345-9350, and in US 2009/0246830 or US 2011/0143424 (each of which is hereby incorporated by reference in its entirety), in which the influenza virus is produced by transfecting cells, using a polyamine derivative (Trans IT-LT1), with 8 plasmids each containing a cDNA complementary to one influenza vRNA under the control of an RNA polymerase I promoter and an RNA polymerase I terminator, and 8 plasmids each containing a cDNA complementary to one of the PA, PB1, PB2, NP, HA, NA, M and NS mRNAs under the control of RNA polymerase II promoter. In particular, the cells are human kidney embryonic adherent cells (293T cell line);

(ii) the 12 plasmid method, such as the method described by Fodor et al, 1999, J Virol, 73(1 1):9679-9682, and in US 2004/0142003, US 2012/0058538 (each of which is hereby incorporated by reference in its entirety) in which the influenza virus is produced by transfecting a first cell type with 8 plasmids each containing a cDNA complementary to one influenza vRNA under the control of an RNA polymerase I promoter and an RNA polymerase I terminator (hepatitis delta ribozyme), and 4 plasmids each containing a cDNA complementary to one of the NP, PA, PB1 and PB2 mRNAs under the control of RNA polymerase II promoter, and by further amplifying the virus on a second cell type. In particular, said first cell type is Vero cells and said second cell type is MDBK;

(iii) the 13 plasmid method, such as the method described by De Wit et al, 2007, Journal of General Virology, 88:1281-1287 (which is hereby incorporated by reference in its entirety) in which the influenza virus is produced by transfecting cells with 8 plasmids each containing a cDNA complementary to one influenza vRNA under the control of an T7 RNA polymerase promoter and an T7 RNA polymerase terminator, 4 plasmids each containing a cDNA complementary to one of the NP, PA, PB1 and PB2 mRNAs under the control of RNA polymerase II, and one plasmid containing the cDNA complementary to the mRNA encoding the T7 RNA polymerase and a nuclear localization signal under the control of RNA polymerase II. In particular, the transfected cells are Vero, 293T, or QT6 (fibrosarcoma cell line from Japanese quail) cells.

(iv) the 8 plasmid method, such as the method described by Hoffmann et al, 2000, PNAS, 97(1 1):6108-61 13 and in WO 01/83794 (each of which is hereby incorporated by reference in its entirety) in which each plasmid is capable of expressing both mRNA and vRNA(s). Thus each plasmid contains cDNA complementary to one influenza vRNA and two transcription cassettes instead of one as in the preceding case. The cDNA complementary of each of the eight influenza virus vRNAs is inserted between the polymerase I terminator and the polymerase I promoter. This polymerase I transcription unit is flanked by the polymerase II promoter and a polyadenylation signal. The first transcription cassette allows the transcription of cDNA in the form of a vRNA. The second transcription cassette allows the transcription of cDNA in the form of mRNA which is then translated into viral protein(s) using the cellular machinery. With the aid of this double cassette system for transcription, also called Pol 1-Pol II system, the cDNA of the same plasmid is transcribed both in the form of vRNA and in the form of mRNA. This manifests itself at the level of the transfected cell by the expression of a vRNA and of one or more viral proteins. In particular, a co-culture of adherent MDCK cells and of 293T cells and, as transfection agent, a polyamine derivative (Trans IT-LT1) are used.

(v) the 3 plasmid method, such as the method described by Neumann et al, 2005, PNAS, 102(46): 16825-16829 (which is hereby incorporated by reference in its entirety), in which the influenza virus is produced by transfecting cells with one plasmid containing the 8 cDNAs complementary to PB2, PB1, PA, HA, NP, NA, M and NS vRNAs each under the control of an RNA polymerase I promoter and a polymerase I terminator and 2 plasmids, the first one containing the 3 cDNA complementary to one of the PB2, PB1 and PA mRNAs and the second one containing the cDNA complementary to the NP mRNA, under the control of a RNA polymerase II promoter. In particular, the transfected cells are 293T or Vero.

(vi) the 1 plasmid method, such as the method described by Zhang et al, J. Virol., 83(18): 9296-9303 (which is hereby incorporated by reference in its entirety), in which the influenza virus is produced by transfecting cells with one plasmid containing the 8 cDNAs complementary to PB2, PB1, PA, HA, NP, NA, M and NS vRNA under the control of murine polymerase I terminator and a chicken RNA polymerase I promoter and with a polymerase II promoter and a polyadenylation signal between PB2, PB1, PA and NP cDNAs. In particular, the transfected cells are CEF cells.

(vii) the method described in WO 2005/062820 (which is hereby incorporated by reference in its entirety) using two different cellular systems: in a first step, cells are transfected with 8 bidirectional plasmids with the PolI-PolII system (Pol/PolI) and then in a second step, the transfected cells are cultured with cells from another cell line that is very permissive for the influenza virus in order to amplify the production of the influenza virus. In particular, said transfected cells in the first step are Vero cells, and said other cell line in the second step are CEK or CEF cell lines which are lines derived from chicken embryo cells.

In some embodiments, prior to being used in the reverse genetics methods described above, nucleic acid sequences encoding the engineered influenza HA polypeptides may be further optimized according to the method described in U.S. provisional application 62/172,949, incorporated by reference herein.

In some embodiments, influenza virus for use in vaccines is grown in eggs, for example, in embryonated hen eggs, in which case the harvested material is allantoic fluid. Alternatively or additionally, influenza virus or engineered hemagglutinin polypeptides may be produced from any method using tissue culture to grow the virus. Suitable cell substrates for growing the virus or otherwise recombinantly producing the engineered hemagglutinin polypeptides include, for example, dog kidney cells such as MDCK or cells from a clone of MDCK, MDCK-like cells, monkey kidney cells such as AGMK cells including Vero cells, cultured epithelial cells as continuous cell lines, 293T cells, BK-21 cells, CV-1 cells, or any other mammalian cell type suitable for the production of influenza virus (including upper airway epithelial cells) for vaccine purposes, readily available from commercial sources (e.g., ATCC, Rockville, Md.). Suitable cell substrates also include human cells such as MRC-5 cells. Suitable cell substrates are not limited to cell lines; for example primary cells such as chicken embryo fibroblasts are also included.

Engineered hemagglutinin polypeptides may also be expressed/produced in diverse eukaryotic-based expression systems, including microalgae (e.g. Schizochytrium sp.; see, e.g., Bayne, A-C. V. et al., PLOS ONE, 8(4):e61790, April 2013), plant-based systems (e.g., tobacco plants; see, e.g., Jul-Larsen, A., et al., Hum Vaccin Immunother., 8(5):653-61, 2012), yeast (see, e.g., Athmaram, T. N. et al., Virol J., 8:524, 2011), and fungi (see, e.g., Allgaier, S. et al., Biologicals, 37:128-32, 2009). Bacterial based expression systems are also encompassed by the present invention (see, e.g., Davis, A. R. et al., Gene, 21:273-284, 1983).

In some embodiments, vaccines in accordance with the invention further comprise one or more adjuvants. For example, aluminum salts (Baylor et al., 2002, Vaccine, 20:S18; incorporated herein by reference) and monophosphoryl lipid A (MPL; Ribi et al., 1986, Immunology and Immunopharmacology of Bacterial Endotoxins, Plenum Publ. Corp., NY, p. 407; incorporated herein by reference) can be used as adjuvants in human vaccines. Alternatively or additionally, new compounds are currently being tested as adjuvants in human vaccines, such as AS03, MF59, and saponins such as QS21.

Additionally, some adjuvants are known in the art to enhance the immunogenicity of influenza vaccines, such as poly[di(carboxylatophenoxy)phosphazene] (PCCP; Payne et al., 1998, Vaccine, 16:92; incorporated herein by reference), interferon-γ (Cao et al., 1992, Vaccine, 10:238; incorporated herein by reference), block copolymer P1205 (CRL1005; Katz et al., 2000, Vaccine, 18:2177; incorporated herein by reference), interleukin-2 (IL-2; Mbwuike et al., 1990, Vaccine, 8:347; incorporated herein by reference), and polymethyl methacrylate (PMMA; Kreuter et al., 1981, J. Pharm. Sci., 70:367; incorporated herein by reference).

In addition to immunogenic compositions (e.g., vaccines comprising one or more of the engineered influenza hemagluttin polypeptides described herein), the present invention provides other therapeutic compositions useful in the treatment of viral infections. Therapeutic compositions include, for example, influenza VLPs, fusions proteins, and an engineered HA polypeptide itself as described herein.

In some embodiments, the present invention provides pharmaceutical compositions comprising antibodies or other agents related to provided HA polypeptides. For example, the invention provides compositions containing antibodies that recognize virus particles containing a particular engineered HA polypeptide, nucleic acids (such as nucleic acid sequences complementary to HA sequences, which can be used for RNAi), glycans that compete for binding to HA receptors, small molecules or glycomimetics that compete the glycan-HA polypeptide interaction, or any combination thereof. In some embodiments, collections of different agents, having diverse structures are utilized. In some embodiments, therapeutic compositions comprise one or more multivalent agents. In some embodiments, treatment comprises urgent administration shortly after exposure or suspicion of exposure.

In some embodiments, any of the immunogenic compositions (e.g., vaccines) described herein offer broad cross-protection against different varieties of influenza viruses. For example, in some embodiments, immunogenic compositions described herein offer cross-protection against avian, swine and/or human-adapted influenza A viruses. In some embodiments, any of the immunogenic compositions described herein offer cross-protection against one or more influenza A subtypes. In some embodiments, the immunogenic compositions described herein provide cross-protection against multiple strains of influenza A H1-subtype viruses (see, e.g., FIGS. 6 and 7).

In general, immunogenic and/or pharmaceutical composition will include a therapeutic agent in addition to one or more inactive agents such as a sterile, biocompatible carrier including, but not limited to, sterile water, saline, buffered saline, or dextrose solution. Alternatively or additionally, the composition can contain any of a variety of additives, such as stabilizers, buffers, excipients (e.g., sugars, amino acids, etc.), or preservatives.

In some embodiments, pharmaceutical compositions as described herein include a therapeutically effective amount of an influenza VLP (comprising an engineered HA polypeptide as described herein) alone or in combination with a pharmaceutically acceptable carrier. Pharmaceutically acceptable carriers include, but are not limited to, saline, buffered saline, dextrose, water, glycerol, ethanol, and combinations thereof. In some embodiments, the carrier and composition are sterile, and the formulation suits the mode of administration. In some embodiments, a pharmaceutical composition contains minor amounts of wetting or emulsifying agents, or pH buffering agents. In some embodiments, a pharmaceutical composition is a liquid solution, suspension, emulsion, tablet, pill, capsule, sustained release formulation, or powder. In some embodiments, a pharmaceutical composition is formulated for intradermal injection, intranasal administration or intramuscular injection. Any of common pharmaceutical carriers, such as sterile saline solution or sesame oil, may be used. In some embodiments, a medium can also contain conventional pharmaceutical adjunct materials such as, for example, pharmaceutically acceptable salts to adjust the osmotic pressure, buffers, preservatives and the like. In some embodiments, other media that may be used with the compositions and methods provided herein are normal saline and sesame oil.

In some embodiments, the therapeutic agent present in a pharmaceutical composition in accordance with the invention will consist of one or more engineered HA polypeptide as described herein.

In some embodiments, a pharmaceutical composition will include a therapeutic agent that is encapsulated, trapped, or bound within a lipid vesicle, a bioavailable and/or biocompatible and/or biodegradable matrix, or other microparticle. In some embodiments, an immunogenic or pharmaceutical composition comprises nanoparticles displaying the engineered hemagglutinin polypeptides described herein. In some embodiments, the nanoparticles are ferritin nanoparticles (see, e.g., U.S. pre-grant publication 2014/0072958).

Pharmaceutical compositions of the present invention may be administered either alone or in combination with one or more other therapeutic agents including, but not limited to, vaccines and/or antibodies. By "in combination with," it is not intended to imply that the agents must be administered at the same time or formulated for delivery together, although these methods of delivery are within the purview of the present invention. In general, each agent will be administered at a dose and on a time schedule determined for that agent. Additionally, the invention encompasses the delivery of pharmaceutical compositions in accordance with the invention in combination with agents that may improve their bioavailability, reduce or modify their metabolism, inhibit their excretion, or modify their distribution within the body. Although the pharmaceutical compositions of the present invention can be used for treatment (e.g., vaccination) of any subject (e.g., any animal) in need thereof, they are most preferably used in the treatment of humans. In some embodiments, pharmaceutical compositions in accordance with the invention and/or engineered HA polypeptides as described herein are administered in combination with one or more of an anti-viral agent (e.g., Oseltamivir [TAMIFLU®], Zanamavir [RELEZA®], etc.) and/or a sialidase.

Pharmaceutical compositions of the present invention can be administered by a variety of routes, including oral, intravenous, intramuscular, intra-arterial, subcutaneous, intraventricular, transdermal, interdermal, rectal, intravaginal, intraperitoneal, topical (as by powders, ointments, creams, or drops), mucosal, nasal, buccal, enteral, sublingual; by intratracheal instillation, bronchial instillation, and/or inhalation; and/or as an oral spray, nasal spray, and/or aerosol. In general the most appropriate route of administration will depend upon a variety of factors including the nature of the agent (e.g., its stability in the environment of the gastrointestinal tract), the condition of the patient (e.g., whether the patient is able to tolerate oral administration), etc.

In some embodiments parenteral administration, such as subcutaneous, intravenous or intramuscular administration, is achieved by injection. In some embodiments, injectables are prepared in conventional forms, either as liquid solutions or suspensions, solid forms suitable for solution or suspension in liquid prior to injection, or as emulsions. In some embodiments, injection solutions and suspensions are prepared from sterile powders, granules.

In some embodiments, influenza VLPs, or compositions thereof, are administered in any suitable manner, such as with pharmaceutically acceptable carriers. As persons of skill are aware, pharmaceutically acceptable carriers are determined in part by the particular composition being administered, as well as by the particular method used to administer the composition. Accordingly, there is a wide variety of suitable formulations of pharmaceutical compositions as described herein.

In some embodiments, preparations for parenteral administration include sterile aqueous or nonaqueous solutions, suspensions, and emulsions. Exemplary non-aqueous solvents include propylene glycol, polyethylene glycol, vegetable oils such as olive oil, and injectable organic esters such as ethyl oleate. Exemplary aqueous carriers include water, alcoholic/aqueous solutions, emulsions or suspensions, including saline and buffered media. In some embodiments, parenteral vehicles include sodium chloride solution, Ringer's dextrose, dextrose and sodium chloride, lactated Ringer's, or fixed oils. In some embodiments, intravenous vehicles include fluid and nutrient replenishers, electrolyte replenishers (such as those based on Ringer's dextrose), and the like. In some embodiments, preservatives and/or other additives may also be present. Exemplary preservatives and/or other additives include antimicrobials, anti-oxidants, chelating agents, and inert gases and the like.

In some embodiments, compositions (influenza VLPs or otherwise comprising an HA polypeptide as described herein) are administered as a pharmaceutically acceptable acid- or base-addition salt, formed by reaction with inorganic acids such as hydrochloric acid, hydrobromic acid, perchloric acid, nitric acid, thiocyanic acid, sulfuric acid, and phosphoric acid, and organic acids such as formic acid, acetic acid, propionic acid, glycolic acid, lactic acid, pyruvic acid, oxalic acid, malonic acid, succinic acid, maleic acid, and fumaric acid, or by reaction with an inorganic base such as sodium hydroxide, ammonium hydroxide, potassium hydroxide, and organic bases such as mono-, di-, trialkyl and aryl amines and substituted ethanolamines.

At present the oral or nasal spray or aerosol route (e.g., by inhalation) is most commonly used to deliver therapeutic agents directly to the lungs and respiratory system. However, the invention encompasses the delivery of the pharmaceutical composition in accordance with the invention by any appropriate route taking into consideration likely advances in the sciences of drug delivery.

In some embodiments, preparations for inhaled or aerosol delivery comprise a plurality of particles. In some embodiments, such preparations have a mean particle size of about 1, about 2, about 3, about 4, about 5, about 6, about 7, about 8, about 9, about 10, about 11, about 12, or about 13 microns. In some embodiments, preparations for inhaled or aerosol delivery are formulated as a dry powder. In some embodiments, preparations for inhaled or aerosol delivery are formulated as a wet powder, for example through inclusion of a wetting agent. In some embodiments, the wetting agent is selected from the group consisting of water, saline, or other liquid of physiological pH.

In some embodiments, compositions in accordance with the invention are administered as drops to the nasal or buccal cavity. In some embodiments, a dose may comprise a plurality of drops (e.g., 1-100, 1-50, 1-20, 1-10, 1-5, etc.)

In some embodiments, compositions in accordance with the invention are administered using a device that delivers a metered dosage of composition (e.g., of engineered HA polypeptide).

Suitable devices for use in delivering intradermal pharmaceutical compositions described herein include short needle devices such as those described in U.S. Pat. Nos. 4,886,499, 5,190,521, 5,328,483, 5,527,288, 4,270,537, 5,015,235, 5,141,496, 5,417,662 (all of which are incorporated herein by reference). Intradermal compositions may also be administered by devices which limit the effective penetration length of a needle into the skin, such as those described in WO1999/34850, incorporated herein by reference, and functional equivalents thereof. Also suitable are jet injection devices which deliver liquid vaccines to the dermis via a liquid jet injector or via a needle which pierces the stratum corneum and produces a jet which reaches the dermis. Jet injection devices are described for example in U.S. Pat. Nos. 5,480,381, 5,599,302, 5,334,144, 5,993,412, 5,649,912, 5,569,189, 5,704,911, 5,383,851, 5,893,397, 5,466,220, 5,339,163, 5,312,335, 5,503,627, 5,064,413, 5,520,639, 4,596,556, 4,790,824, 4,941,880, 4,940,460, WO1997/37705, and WO1997/13537 (all of which are incorporated herein by reference). Also suitable are ballistic powder/particle delivery devices which use compressed gas to accelerate vaccine in powder form through the outer layers of the skin to the dermis. Additionally, conventional syringes may be used in the classical mantoux method of intradermal administration.

General considerations in the formulation and manufacture of pharmaceutical agents may be found, for example, in *Remington's Pharmaceutical Sciences,* $19^{th}$ ed., Mack Publishing Co., Easton, Pa., 1995; incorporated herein by reference.

Pharmaceutical compositions in accordance with the invention may be administered in any dose appropriate to achieve a desired outcome. In some embodiments, the desired outcome is induction of a lasting adaptive immune response against multiple influenza strains. In some embodiments, the desired outcome is reduction in intensity, severity, and/or frequency, and/or delay of onset of one or more symptoms of influenza infection.

In some embodiments, pharmaceutical compositions in accordance with the invention are administered in single or multiple doses. In some embodiments, pharmaceutical compositions in accordance with the invention are administered in multiple doses administered on different days (e.g., prime-boost vaccination strategies). In some embodiments, pharmaceutical compositions in accordance with the invention are administered according to a continuous dosing regimen, such that the subject does not undergo periods of less than therapeutic dosing interposed between periods of therapeutic dosing. In some embodiments, pharmaceutical compositions in accordance with the invention are administered according to an intermittent dosing regimen, such that the subject undergoes at least one period of less than therapeutic dosing interposed between two periods of therapeutic dosing.

In some embodiments, a dose administered to a subject should be sufficient to induce a beneficial therapeutic response in a subject over time, or to inhibit or prevent H1N1 influenza virus infection. The dose required will vary from subject to subject depending on the species, age, weight and general condition of the subject, the severity of the infection being treated, the particular composition being used and its mode of administration.

The present invention will be more fully understood by reference to the following Examples. All literature citations are incorporated by reference.

EXAMPLES

These Examples are set forth to aid in the understanding of the invention but are not intended to, and should not be construed to limit its scope in any way. The Examples do not include detailed descriptions of conventional methods that would be well known to those of ordinary skill in the art (molecular cloning techniques, etc.). Unless indicated otherwise, parts are parts by weight, molecular weight is average molecular weight, temperature is indicated in Celsius, and pressure is at or near atmospheric.

Example 1

Design and Methodology for Construction of Hemagglutinin (HA) Polypeptides

The present Example describes the design and production of engineered HA polypeptides that elicit broad neutralizing immune responses. The engineered HA polypeptides combine multiple B-cell epitopes from different hemagglutinin sequences to create mosaic antigens.
Cross-Reactive Vaccine Development The present Example specifically illustrates construction of engineered HA polypeptides that combine HA sequences from subtype H1 strains. These mosaic antigens are predicted to confer cross-protection against multiple subtype H1 strains by maximizing sequence homology for at least one neutralizing epitope. Further, these mosaic antigens can be used alone or in combination with other influenza antigens, as a component of seasonal and/or pandemic influenza vaccines, or as part of a vaccination regimen intended to confer long-lasting, multi-season protection against influenza infection.

Additional Examples presented herein demonstrate the successful immune response elicited by these engineered HA polypeptides, as assayed by HA inhibition and microneutralization using sera from immunized animals. These Examples demonstrate the potential of the presently described methodology for the design and production of engineered HA polypeptides and provide the next-generation of broadly cross-reactive and neutralizing influenza vaccines.

FIG. 2 sets forth an exemplary flowchart of the methodology for the design and production of engineered HA polypeptides as described herein.

One rational design approach to creating a broadly protective HA-based vaccine is to include epitopes from as many viral isolates as possible in a polyvalent vaccine. The methodology behind the generation of mosaic B-cell epitope sequences is termed SMARt for the 'Structural Mapping of Antigenic Repertoires'. The first stage of SMARt relies on the identification and classification of known B-cell epitopes for the influenza A hemagglutinin molecule. The epitopes and antigenic sites for Influenza A hemagglutinin were subdivided into three classes (tiers): 1) epitopes supported by 3D-structural mapping of the contact sites from neutralizing antibodies; 2) neutralizing epitopes not supported by 3D mapping of contact sites; and 3) classical antigenic regions that lack precise mapping of epitope residues. A polyvalent vaccine with M proteins supports the inclusion of M epitope sequence patterns for each epitope site. Each epitope site with N unique epitope sequences has multiple possible combinations of subsets of M unique epitope sequence patterns:

$$C_M^N = \frac{N!}{M!(N-M)!}$$

This was reduced to M subsets, or cassettes, per epitope site by creating a cassette for each unique epitope sequence pattern and optimizing the selected epitope sequence patterns to optimize alignment coverage. There were M possible cassettes for R epitopes sites, creating $R^M$ possible combinations. Mosaic sequence templates were generated for large numbers of random combinations of cassettes to sample a subset of the $R^M$ possible combinations. The alignment coverage for nine geographic regions, viral isolate years, and sub-family clusters was evaluated for each mosaic sequence template. The set of mosaic sequence templates were then combined with target backbone sequence(s) and subjected to structural refinement to generate candidate mosaic polyvalent sequences for vaccine development.

A low fidelity polymerase enables viruses to evolve over multiple generations to evade immunological memory of hosts. This creates a diverse population of related viruses. Vaccines developed to target specific viral isolates may not protect against infection from different isolates of the same virus. The SMARt approach for developing broadly protective antigens creates polyvalent mosaic sequences that include B-cell epitopes from as many viral isolates as possible. Starting with known neutralizing antibody epitopes and antigenic sites, SMARt identifies corresponding antigenic repertoires ($A_{1-N}$, $B_{1-N}$, $C_{1-N}$, ...) from an alignment of N sequences and generates combinations ($A_{23}$, $B_{12}$, $C_{55}$, ...; $A_{15}$, $B_{38}$, $C_{27}$, ...) from the repertoires to create sets of M mosaic sequences. To optimize the epitope sequence patterns selected, an ordered subset of M epitope sequence patterns were generated for each unique epitope sequence pattern with order optimized for alignment coverage. For each unique epitope sequence pattern, $E_j$, additional epitope sequence patterns ($E_k$, $E_m$, ...) from the same epitope site were selected to maximize the alignment coverage using a scoring matrix (e.g., blosum80.mat). Ordered epitope sequence patterns cassettes from different epitope sites were randomly combined to create large numbers of mosaic template sequences (e.g., for classical antigenic sites, Ca, Cb, Sa, and Sb [Igarashi, et al., 2009]: $Ca1_i$, $Ca2_j$, $Cb_k$, $Sa_l$, $Sb_m$, . . . represents the selected cassettes for one mosaic template set of sequences).

To avoid over-representation biases in the available sequences, principal component analysis (PCA) was used to define virus sub-family clusters. The best mosaic sequence templates were selected by evaluating overall alignment coverage by geographic regions, viral isolate years, and PCA clusters. The selected set of mosaic template sequences were combined with target backbone sequences to generate the set of full-length mosaic protein sequences. Structure refinement of these mosaic sequences yields the final set of vaccination proteins. An overview of the mosaic approach is shown in FIG. 8.

Principal Component Analysis to Assess Cross Reactivity of Influenza A HAs

Principal Components Analysis (PCA) is a common technique for working with high dimensional data and highlighting patterns in the data (i.e. it can be used to simplify large datasets and facilitate data exploration and visualization). Applied to biological sequences (proteins, genes), the technique enables comparison of thousands of sequences and the identification of groups of similar sequences based on a measure of sequence dissimilarity (Hamming distance, percent identity, percent similarity, surface accessibility, etc). In the case of Human influenza A viruses, hemagglutinin (HA) protein sequences were obtained from the NCBI Influenza Virus Resource database, trimmed to remove signal peptides, transmembrane regions and cytoplasmic tails and the resulting ectodomain sequences were aligned. The pair-wise dissimilarity matrix was calculated from the multiple sequence alignment based on the Hamming distance between pairs of sequences with no prior assumptions regarding function or structure of the sequences. Principal Components Analysis (PCA) was applied to the dissimilarity matrix for the purpose of dimension reduction and to facilitate visualization of the relative distances between HA proteins. The first 2-3 principal components were retained for visualizing protein relationships in sequence space and represent a reasonable approximation of the general structure of the phylogenetic tree. Calculations were performed using custom scripts written in python and R.

Figure 9:
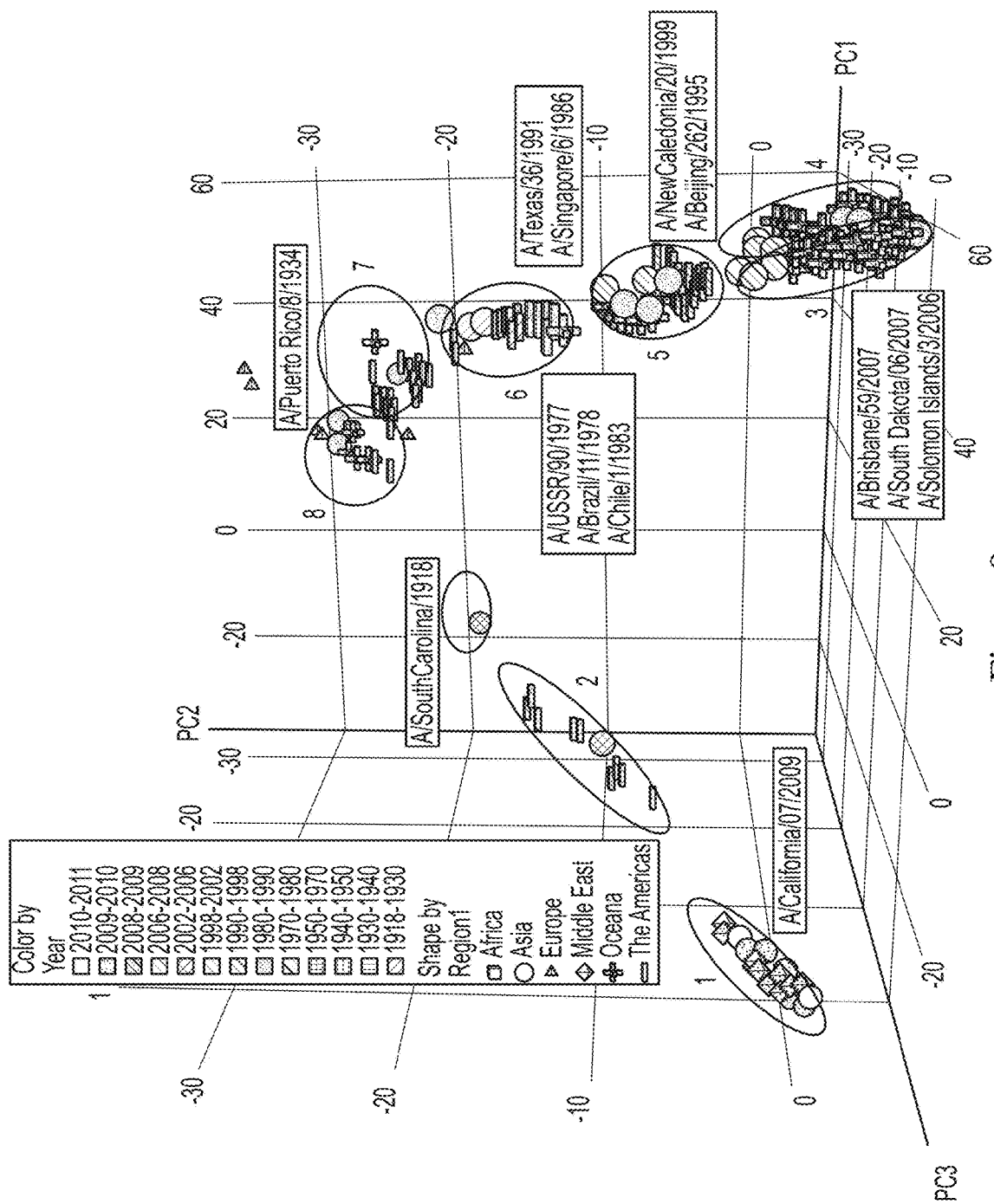
FIG. 9 shows an exemplary principal component analysis plot used to identify H1N1 HA clusters.

A broadly protective antigen should be cross-reactive across multiple clusters within and between subtypes (FIG. 9). Modifications designed into the engineered HAs were deduced from an in silico analysis of sequence variation in both past and current circulating influenza strains. This analysis included mapping antigenic and epitope patterns as well as structural modeling of the HA protein. Targeted changes were subsequently introduced at precise amino acid residue locations and/or specific regions of the protein with known immune profiles in order to yield novel influenza A HA polypeptides that would be reactive across the sequence clusters illustrated in FIG. 9.

Each novel mosaic design was composed of multiple neutralizing hemagglutinin B-cell epitope patterns derived from antigenically diverse influenza A subtypes (including both Yamagata and Victoria lineages). The mosaic pattern of B-cell epitopes is assembled onto a backbone hemagglutinin sequence. In the some embodiments, one of the following backbone hemagglutinin sequences was used A/New Caledonia/20/99/California/07/2009. The selected backbone provides the inter-epitope sequence of the engineered construct as well as the signal peptide and transmembrane domains required for full-length hemagglutinin molecules that are expressed and functional.

Creation of Multiple Sequence Alignment

All available full-length hemagglutinin protein sequences were downloaded from the NCBI's Influenza Virus Resource (ncbi.nlm.nih.gov/genomes/FLU/; (Bao et al., 2008, The Influenza Virus Resource at the National Center for Biotechnology Information. J. Virol. Jan; 82(2):596-601). Full-length sequences were sub-divided for host and virus sub-type. For the construction of mosaic antigens a host range restriction to human was applied to each dataset. In the case of the human H1N1 viral sub-type sequences, all sequences available as of Apr. 13, 2011 were included (Table 3). Redundant sequences were removed using CDHIT (Fu et al., 2012, CD-HIT: accelerated for clustering the next-generation sequence data, Bioinformatics, 28 (23):3150-3152; Weizhong and Dodzik, 2006, Cd-hit: a fast program for clustering and comparing large sets of protein or nucleotide sequences, Bioinformatics, 22(13):1658-1659; Weizhong et al., 2002, Tolerating some redundancy significantly speeds up clustering of large protein databases, Bioinformatics, 18(1):77-82; Weizhong et al., 2001, Clustering of highly homologous sequences to reduce the size of large protein databases, Bioinformatics, 17(3):282-283) and sequences containing ambiguous residues (X, J, ) were excluded to yield a final, non-redundant set of 2043 H1N1 hemagglutinin sequences. The non-redundant sequences were initially aligned with MAFFT (e.g., see Katoh and Standley, 2013, Mol. Biol. Evol. 30(4):772-780, or Kotoh et al., 2002, Nucleic Acids Res. 30:3059-3066) and then manually reviewed and edited as required. The manually edited multiple sequence alignment was used for the identification of sequence clusters and for the construction of mosaic sequences.

TABLE 3

| Cluster | No. of Sequences | Vaccine strains included |
| --- | --- | --- |
| 1 | 1255 | A/California/07/2009 |
| 2 | 13 | No vaccine strain but includes New Jersey/1976 strain |
| 3 | 353 | A/Solomon Islands/3/2006, A/Brisbane/59/2007, A/South Dakota/06/2007 |
| 4 | 265 | A/Beijing/262/1995, New Caledonia/20/1999 |
| 5 | 52 | A/Texas/36/1991, Taiwan/01/1986, Singapore/6/1986 |
| 6 | 43 | A/USSR/90/1977, A/Brazil/11/1978, A/Chile/1/1983 |
| 7 | 23 | No vaccine strains |
| 8 | 14 | No vaccine strains but includes A/Puerto Rico/8/1934 |

Identification of Epitopes for Target Protein of Interest

Target human B-cell antibody epitopes were identified from crystal structures of hemagglutinin with neutralizing antibodies (Table 4), the Immune Epitope Database (IEDB; Yang, et al., 2009, Nucleic Acids Research, 37, D423-D430), and antigenic sites from literature (e.g., Igarashi et al., 2010, PLoS ONE, 5, e8553, 1-7). Identified epitopes were classified on the basis of supporting publications and structural models into one of three tiers. Tier 1 consists of neutralizing epitopes for which 3D structural models of antigen-antibody contact sites were available. Tier 2 of epitopes includes neutralizing epitopes not supported by 3D structural models. Tier 3 includes classical antigenic regions (identified, for instance, in the literature) which lack the precise characterization of individual epitopes. Epitopes from H3N2 and H5N1 were also included (Table 4) and mapped to H1N1.

Figures 10A, 10B:
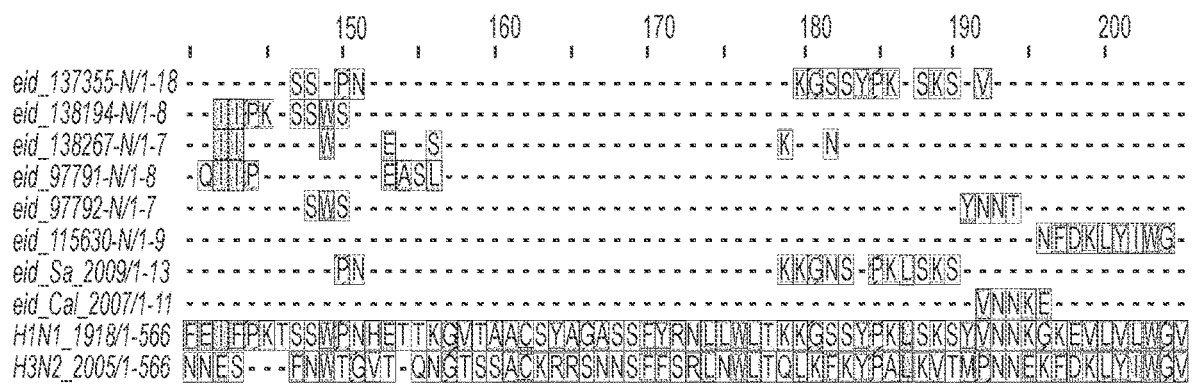
FIG. 10A shows an exemplary comparison of overlapping H1N1 HA epitopes.
FIG. 10B shows an exemplary alignment of overlapping H1N1 HA epitopes.

Antigenic regions can have overlapping epitopes (FIGS. 10A and 10B). Epitope sites for 97823, 97824, and 99799 (IEDB numbering) were nearly identical. The residue positions for 97823 were a subset of the positions for 97824. Epitope 97844 has $N_{35}$, $L_{36}$, and $D_{46}$ not covered by 99799 and 9799 has $V_{364}$ not covered by 97824. For overlapping epitope, the order in which the epitopes were layered into the mosaic templates is important. The residues in the mosaic sequences were determined by the order that the epitopes were added to the templates. For two or more overlapping epitopes, residue positions defined by previously added epitopes mask a subset of the positions for the subsequently added overlapping epitopes. One alternative is to allow the ordered layering of overlapping epitope sequence patterns that were derived from different source viral isolates resulting in mosaic sequences with hybrid epitopes not reflected in the viral isolates in the alignment. Alternatively, overlapping epitopes can be combined and selected consistently from the same viral isolates. For example, adding V364 from 99799 with 97824 generates a combined antigenic site for 97823, 97824, and 99799 (FIG. 10A). Similarly, epitopes 137355, 138194, 138269, and 97791 can be combined into one or two combined sites (FIG. 10B). This second approach was used to resolve overlapping epitopes.

Figure 11:
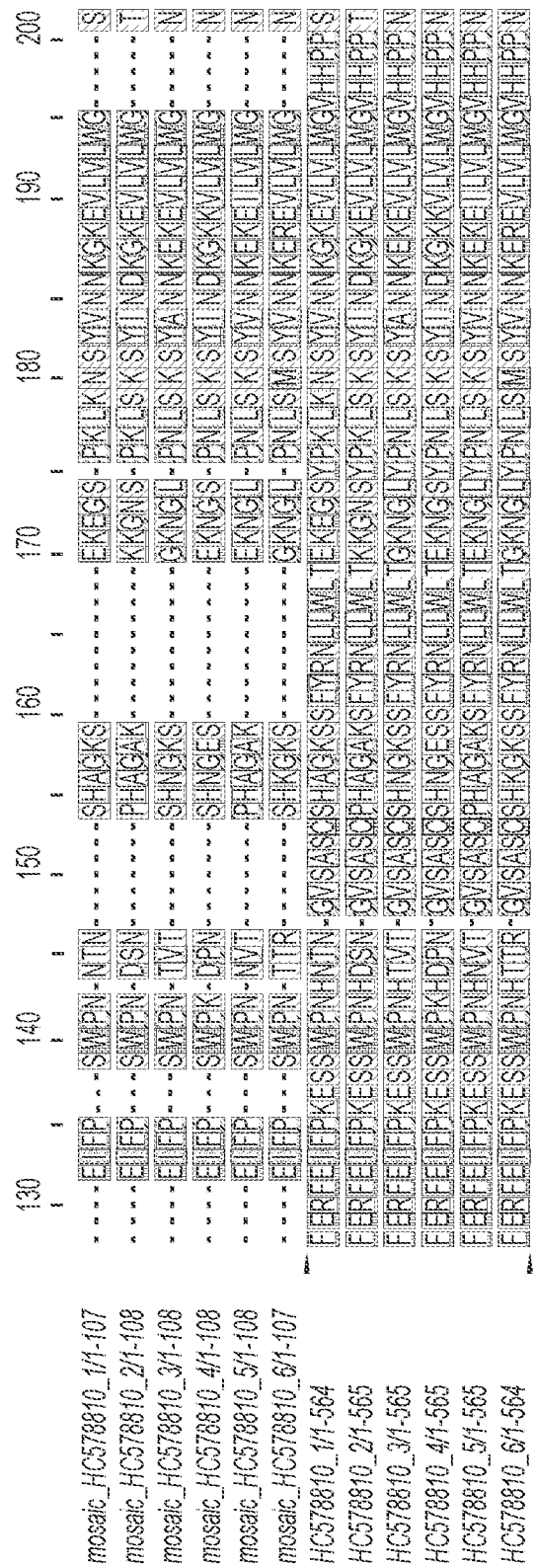
FIG. 11 shows an exemplary alignment of six mosaic templates (A-F) and corresponding mosaic HA sequences (1-6).

The order in which the epitopes were layered into the mosaic templates for overlapping epitopes was considered and accounted for in each template sequence. The residues in the mosaic sequences were determined by the order that the epitopes were added to the templates. Some antigenic regions were observed to have overlapping epitopes. For two or more overlapping epitopes, residue positions defined by previously added epitopes mask a subset of the positions for the subsequently added overlapping epitopes. In some embodiments, one may allow the ordered layering of overlapping epitope sequence patterns that were derived from different viral isolate sources, which results in mosaic sequences with hybrid epitopes not reflected in the viral isolates in the alignment. In some embodiments, overlapping epitopes can be combined and selected consistently from the same viral isolates. FIG. 11 sets forth an exemplary alignment of six mosaic template sequences and corresponding mosaic sequences.

TABLE 4

| Name of Epitope/Antigenic Region | Source | Tier | Residues | # of Unique Epitope sequence patterns |
|---|---|---|---|---|
| Ca1 (2009) | | 3 | I183, N184, D185, K186, G187, S220, S221, R222, E252, P253, G254 | 66 |
| Ca2 (2009) | | 3 | P154, H155, A156, G157, A158, K159, R238, D239 | 73 |
| Cb (2009) | | 3 | L87, S88, T89, A90, S91, S92 | 113 |
| Sa (2009) | | 3 | P141, N142, K170, K171, G172, N173, S174, P176, K177, L178, S179, K180, S181 | 110 |
| Sb (2009) | | 3 | T201, S202, A203, D204, Q206, S207, L208, Q210, N211, A212 | 111 |
| IEDB: 97231 | H5N1 | 2 | CNTKCQTP | 22 |
| IEDB: 97791 | H5N1 | 2 | 131Q, 132I, 133I, 134P, 142E, 143A, 144S, 145L | 45 |
| IEDB: 97792 | H5N1 | 2 | 137S, 138W, 139S, 180Y, 181N, 182N, 183T | 22 |
| IEDB: 97823(a) | H5N1 | 1 | H32, Q34, D35, I36, S292, M293, P294, T319 | 19 |
| IEDB: 97823(b) | H5N1 | 1 | D19, G20, W21, K38, T41, Q42, I45, D46, T49, V52, N53, I56 | 19 |
| IEDB: 97824(a) | H1N1 | 1 | H12, H32, V34, N35, L36, S293, L294, P295, T320 | 18 |
| IEDB: 97824(b) | H1N1 | 1 | D19, G20, W21, Q38, T41, Q42, I45, D46, T49, V52, N53, I56 | 18 |
| IEDB: 99799 | H5N1 | 1 | H24, H44, Q46, S304, M305, V364, D365, G366, W367, K384, T387, Q388, I391, T395, V398, N399, I402 | 47 |
| IEDB: 115630 | H3N2 | 2 | NFDKLYIWG | 21 |
| IEDB: 115652 | H3N2 | 2 | SSRISIYWTIVKP | 47 |
| IEDB: 137355 | H1N1 | 1 | S138, S139, P141, N142, K171, G172, S173, S174, Y175, P176, K177, S179, K180, S181, V183, N211, E259, T261 | 134 |
| IEDB: 138194 | H5N1 | 1 | IIPKSSWS | 45 |
| IEDB: 138267 | H5N1 | 1 | I132, I133, W138, E142, S145, K168, N171 | 40 |
| 1EO8 | H3N2 | 1 | K50, L59, D60, I62, D63, C64, P74, H75, D77, V78, F79, E82, R90, K92, F94, S95, N96, R141, G142, P143, R224, D271, A272, P273 | 32 |

TABLE 4-continued

| Name of Epitope/Antigenic Region | Source | Tier | Residues | # of Unique Epitope sequence patterns |
|---|---|---|---|---|
| 1KEN | H3N2 | 1 | Y98, T126, G135, S136, N137, G144, S145, W153, K156, S157, G158, S159, P162, V163, L164, N165, V166, T167, S186, T187, Q189, E190, T192, S193, L194, S219, W222, R224, G225, L226, S227, S228 | 310 |
| 1QFU | H3N2 | 1 | T48, G49, K50, N53, I58, L59, D60, I62, D63, P74, H75, D77, V78, F79, E82, R90, S91, K92, F94, S95, N96, R141, G142, P143, D271, P273, I274, D275, T276 | 172 |
| 2VIR | H3N2 | 1 | Y98, T128, G129, V130, T131, Q132, N133, G134, G135, S136, N137, S145, W153, T155, K156, S157, G158, S159, T160, E190, S193, L194, L226 | 166 |
| 3LZF | H1N1 | 1 | F121, P122, T124, S125, S126, W127, P128, N129, E131, K157, G158, S159, S160, Y161, P162, K163, S165, K166, S167, Y168, V169, N171, Q196, N197, E246, T248 | 182 |
| 3FKUa | H5N1 | 1 | H12, H32, Q34, D35, I36, S292, M293, P294, T319 | 20 |
| 3FKUb | H5N1 | 1 | M17, V18, D19, G20, W21, K38, T41, Q42, I45, D46, T49, V52, N53, I56 | 25 |
| 3SDYa | H3N2 | 1 | P21, P324, E325, Q327 | 7 |
| 3SDYb | H3N2 | 1 | E15, G16, I18, D19, R25, H26, E30, G31, T32, G33, Q34, A35, A36, L38, T41, N146, A147, E150, R153 | 46 |
| 3GBNa | H1N1 | 1 | H18, H38, V40, N41, L42, S291, L292, P293, T318, G319 | 20 |
| 3GBNb | H1N1 | 1 | I18, D19, G20, W21, A36, Q38, T41, Q42, I45, D46, I48, T49, V52, N53, I56 | 26 |

Identification of Antigenic Repertoires

The concept of an 'antigenic repertoire' as used here can be described as the set of epitopes and antigenic regions that were identified and described according to their corresponding position in the polypeptide chain of HA. The contents of Table 4 for example, represent components of an antigenic repertoire. However, because different strains of influenza may have slightly different sequence at corresponding positions on the polypeptide chain, the repertoire is much larger than the enumerated list of epitope sites or antigenic regions. Selections made from this repertoire are done computationally, scored, then selected for further development and expression for laboratory testing.

Antigenic Repertoires Identification

Figure 12:
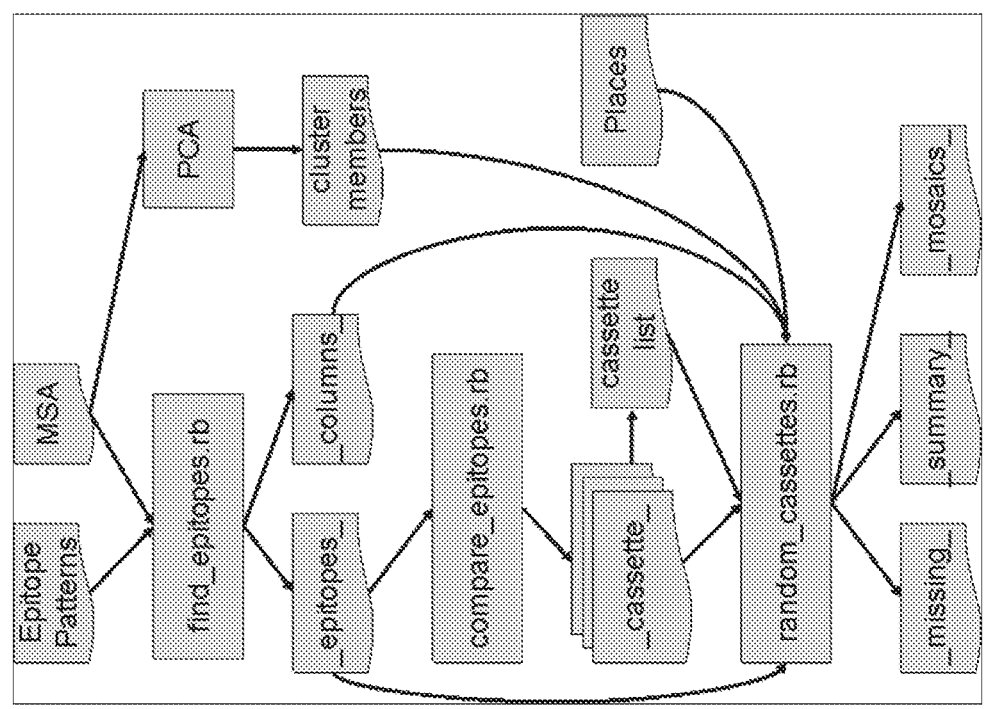
FIG. 12 shows an exemplary flowchart for the design and production of engineered mosaic antigenic polypeptides using the random epitopes process.

To identify corresponding sequence patterns in an epitope across multiple strains, a multiple sequence alignment was searched with linear and discontinuous epitopes in the "find_epitopes_msa" step. When an epitope or antigen site could be identified within the alignment, the corresponding alignment positions were used for all sequences in the alignment to identify all epitope sequence patterns. For linear epitope peptides with no perfect matches in the alignment, limited sequence mismatches were permitted (formula: maximum number of mismatches allowed was (linear site length—5)/2). The set of unique epitope sequence patterns was identified for each epitope site. An exemplary flow chart of mosaic sequence generation is shown in FIG. 12.

Cassette Subsets of Unique Epitope Sequence Patterns

SMARt supports the development of polyvalent vaccines with varying numbers of mosaic constructs. A total of M unique epitope sequence patterns for each epitope site can be included in a polyvalent vaccine of M mosaic proteins. A cassette for each unique epitope pattern can be generated (for example, computationally generated) by adding additional epitope sequence patterns in an alignment coverage optimization order. A cassette was created for each unique epitope sequence with that sequence being the first in the cassette. Additional sequence patterns from the same site were added to each cassette by selecting the next sequence pattern with maximum alignment coverage determined with a scoring matrix (e.g., blosum80). Up to 20 unique sequence patterns were added to each cassette.

Creation of Mosaic Templates Antigenic Repertoires

Sets of mosaic template sequences were generated by randomly combining cassettes (e.g., $Ca1_i$, $Ca2_i$, $Cb_k$, $Sa_1$, $Sb_m$, . . . ). The $i^{th}$ epitope sequence pattern in each cassette was layered onto the $i^{th}$ mosaic template in each set.

Evaluation of Alignment Coverage of Mosaic Epitope Templates

Figure 13:
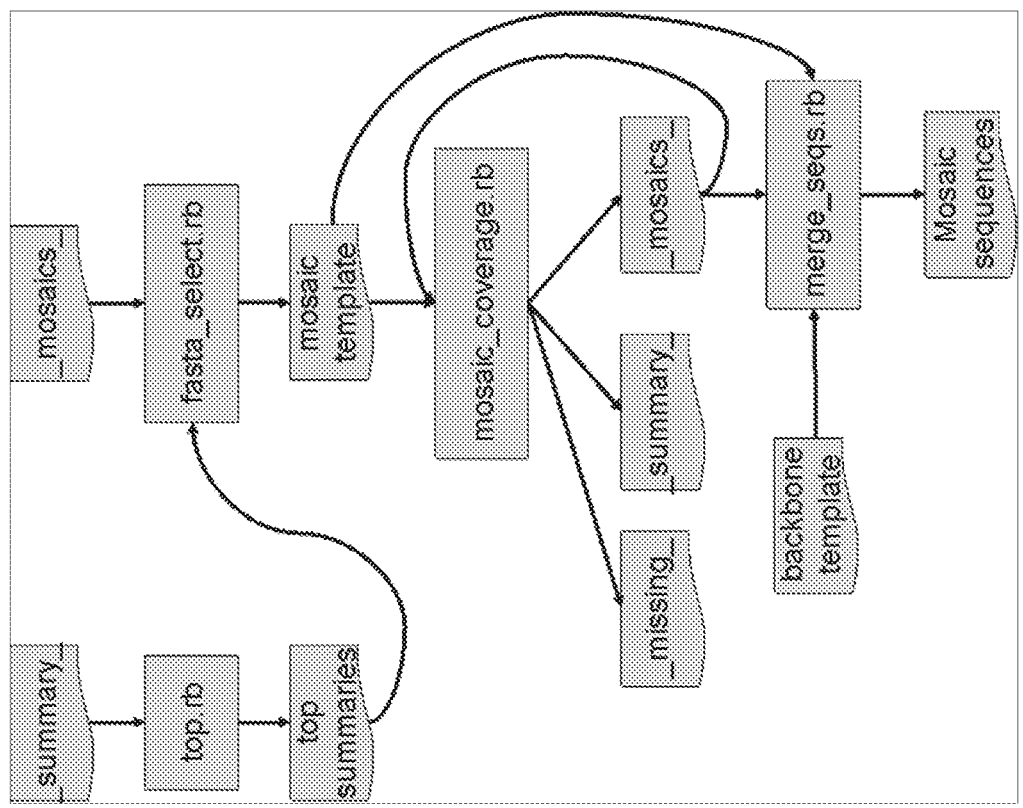
FIG. 13 shows an exemplary flowchart for the design and production of engineered mosaic antigenic polypeptides using the mosaic coverage process.

To avoid potential biases, inherent in the sequence datasets, alignment coverage for viral isolation years, viral geographic regions (Table 5), and sub-family clusters (Table 3) were all evaluated. Multiple sequence alignment coverage by each set of mosaic template sequences was characterized by exact matches of epitope sequence patterns within the alignment. To optimize the selection of the best combinations of epitope cassettes, only the first five mosaic template sequences were used in the evaluation of alignment coverage. Also, only the first five tier 1 epitopes were evaluated in the calculation of alignment coverage to keep the coverage calculations below 100% for the mosaic templates. The best mosaic templates were evaluated by selecting the highest coverage mosaics from the coverage summary. The best set of mosaic templates were extracted from the very large file of mosaic template sequences. An exemplary flowchart of the process overview is shown in FIG. 13.

The best mosaic templates were evaluated by selecting the highest coverage mosaics from the coverage summary information Mosaics with low coverage of one or more clusters were not considered optimal even when they had high overall averages.

TABLE 5

| Geographic Region | Number of Isolates |
| --- | --- |
| Africa | 27 |
| Asia | 136 |
| China | 103 |
| Europe | 186 |
| Japan | 72 |
| Middle East | 36 |
| North America | 184 |
| Oceania | 42 |
| South America | 58 |

Epitope Sequence Pattern Swapping Optimization

To further optimize the best mosaic template sequences set, the epitope sequence patterns within the mosaic templates can be modified and the mosaic templates regenerated. For the epitope sequence patterns in the first of the mosaic sequence templates, nine alternative sequence patterns were substituted for each of the five scored epitopes to evaluate possible alignment coverage improvements.

Combination of Mosaic Epitope Template with Target Backbone Templates

The mosaic epitope sequence templates can be combined with desired viral protein backbone sequence(s). The present Example specifically illustrates the construction of engineered HA polypeptides using mosaic epitope sequence patterns combined with a pre-pandemic influenza backbone sequence (A/New Caledonia/20/99) or a pandemic influenza backbone sequence (A/California/07/2009). Other HA backbone sequences may also be employed for construction of engineered HA polypeptides according to the present invention. The mosaic epitope sequence templates can be combined with desired viral protein backbone sequence(s).

Structural Mapping of Antigenic Repertoires

Figure 14:
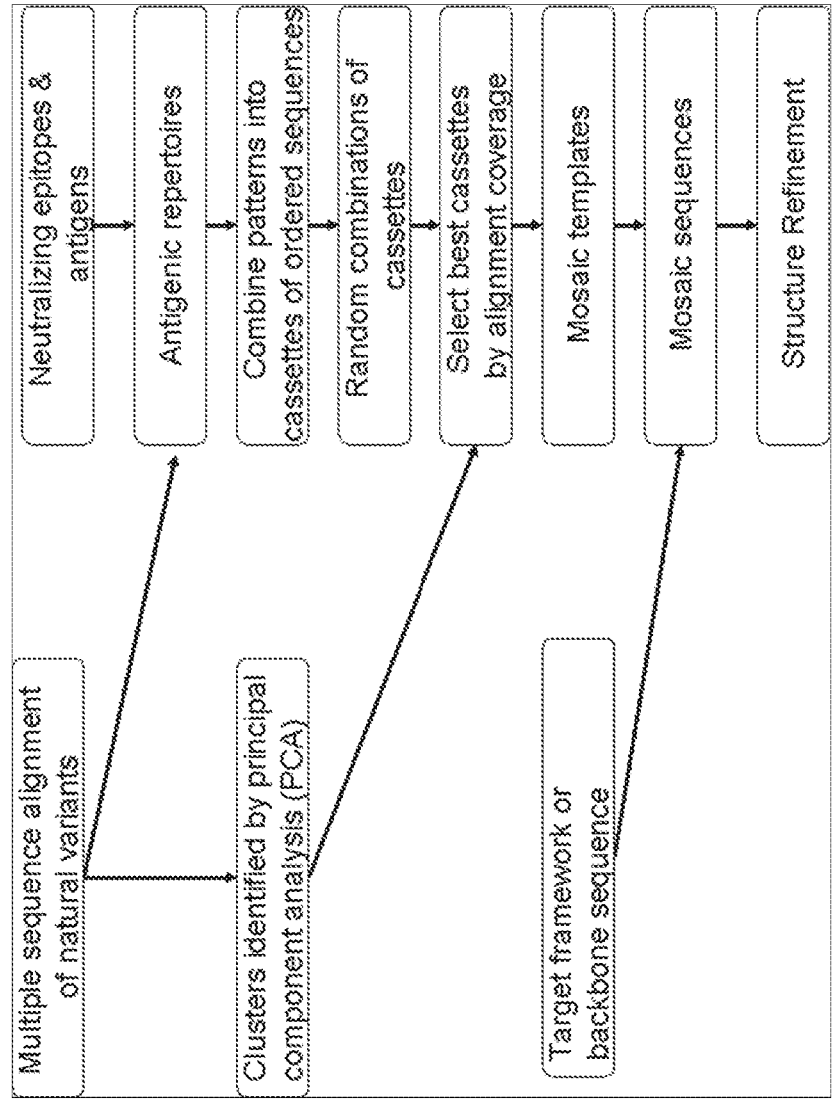
FIG. 14 shows an exemplary flowchart for the design and production of engineered mosaic antigenic polypeptides.
Figure 15:
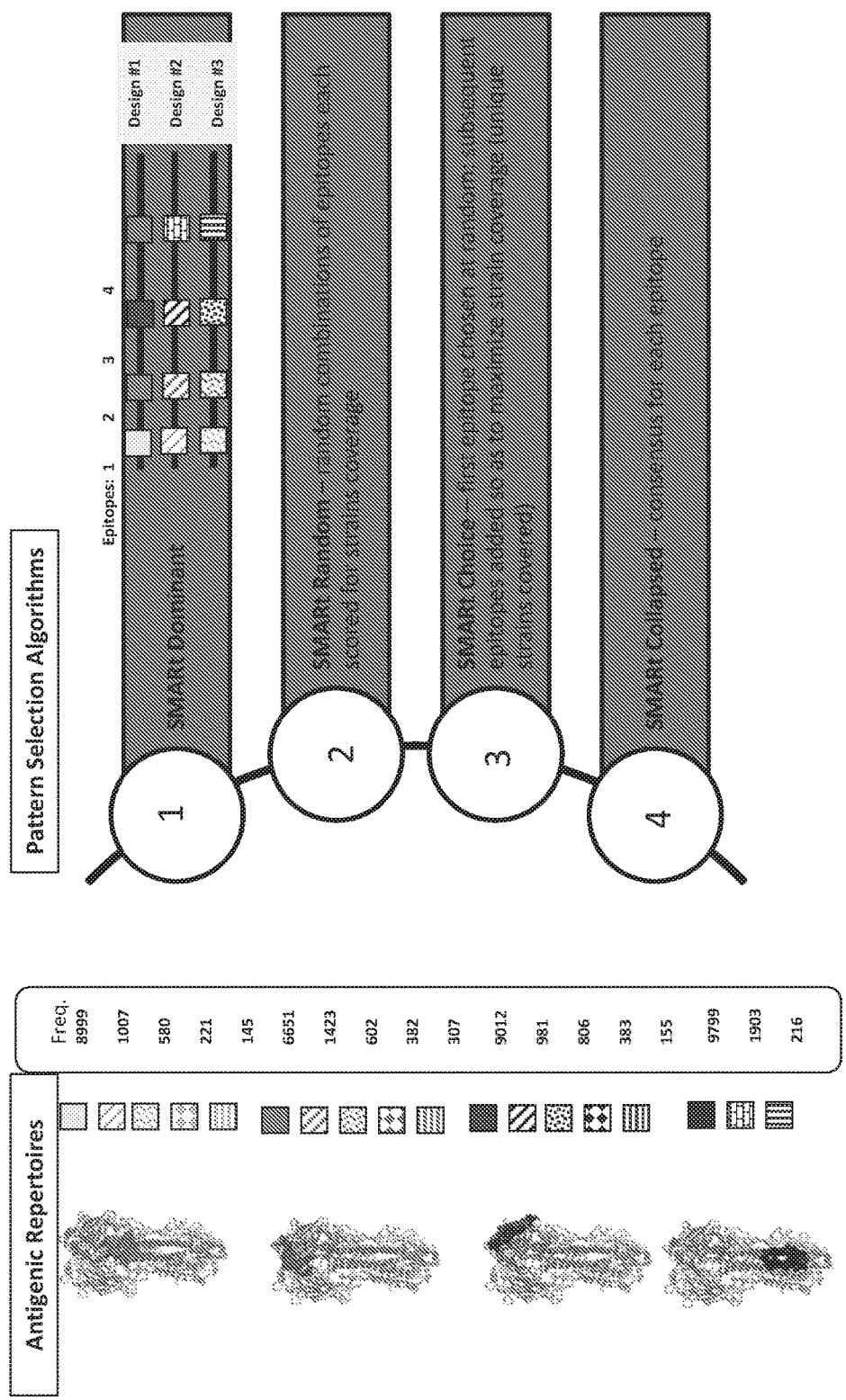
FIG. 15 shows an overview of the four distinct SMARt pattern selection processes.

The approach used here to construct mosaic hemagglutinin sequences is termed 'SMARt' for Structural Mapping of Antigenic Repertoires (an overview of the process is presented in FIGS. 14 and 15). Briefly, known neutralizing and non-neutralizing hemagglutinin B-cell epitopes described for any influenza A and B virus are mapped to corresponding regions of Influenza HA Individual sequences for each B-cell epitopes are extracted and enumerated from the sequences of all available circulating Influenza A strains to generate an 'antigenic repertoire'. Four distinct SMARt workflows were developed to combine antigenic repertoires into novel mosaic hemagglutinin molecules that are distinct from natural circulating strains. An overview of the compiled SMARt workflow is presented in FIG. 3.

Figure 16:
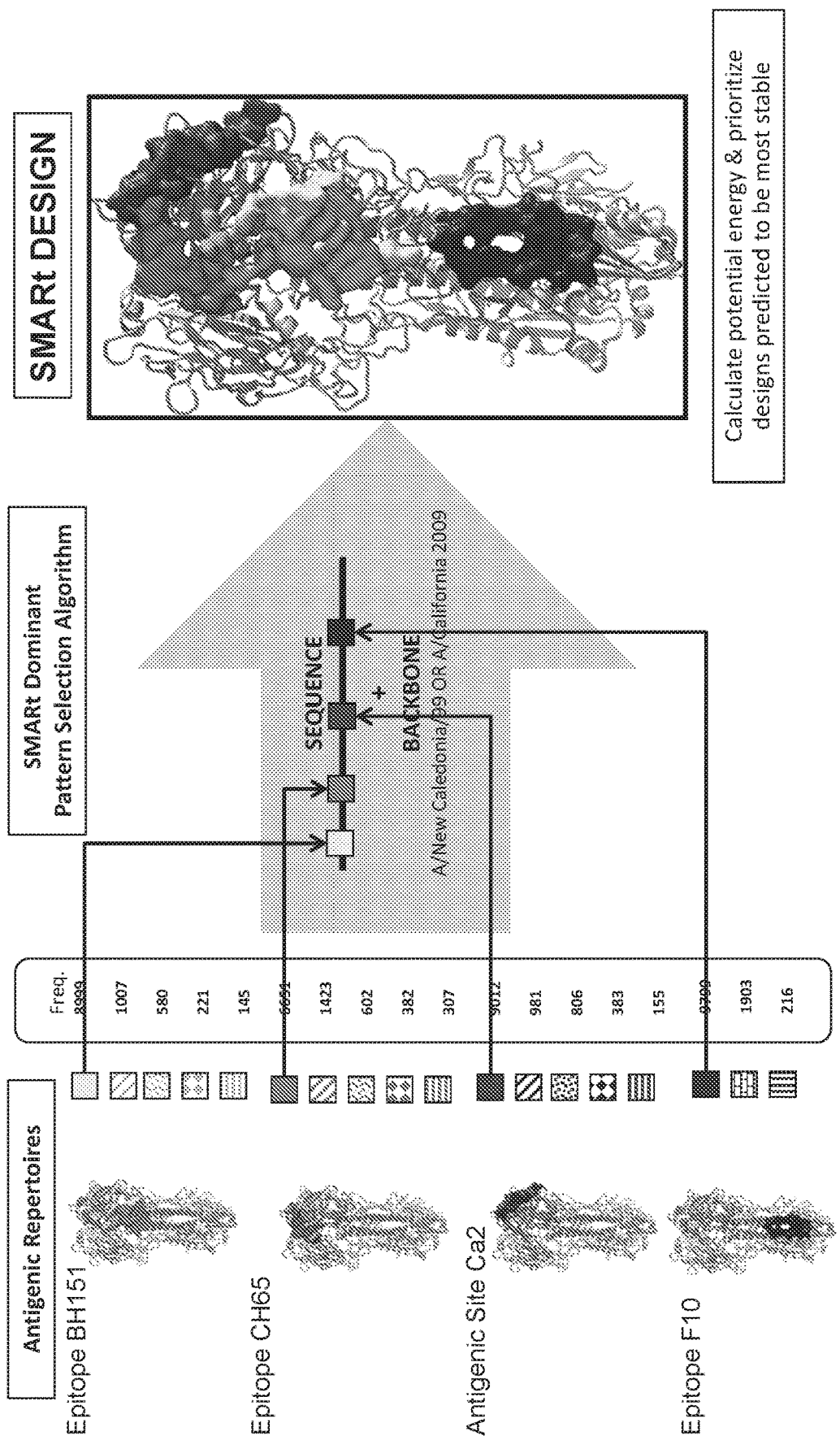
FIG. 16 shows an exemplary workflow of the SMARt Dominant workflow to design engineered mosaic antigenic polypeptides.

FIG. 16 provides a demonstration of the complete process to generate a SMARt Dominant HA design. Table 9 provides epitope sequence patterns represented in FIG. 16.

TABLE 9

| Epitope Sequence Patterns | Counts |
| --- | --- |
| GKAPLKPESLTSDGDPVH | 8999 |
| GKAPLNPELLKNEGNPMD | 1007 |
| GKAPLNPELLTNEGNPMD | 580 |
| GKAPLKPETLTSDGDPVH | 221 |
| GKAPLNPELLTNEGNPMG | 145 |
| YDNKGVTAKWVKKGNSHSTSADQSLQIDQE | 6651 |
| YDNKGVTAKWVKKGNSHSTTADQSLQIQQE | 1423 |
| YTT-GVSASWTGKNGLHPNIGDRALHKDQE | 602 |
| YDNKGVTAKWVKKGNSHSTSADQELQIEQE | 382 |
| YTT-GVSASWTGKNGLHPNIGDKALHKDQE | 307 |
| SHNGESRD | 9012 |
| SHNGKSRD | 981 |
| PHAGAKRE | 806 |
| PHAGAKRG | 383 |
| PHAGAKRG | 155 |
| YHHSLVDGWLTQAIDITKVNVIT | 9799 |
| YHHSLVDGWQTQAINITKVNVIT | 1903 |
| YHHSLIDGWQTQAINITKVNVIT | 216 |

Structural Modeling and Selection of Designs

Figure 19:
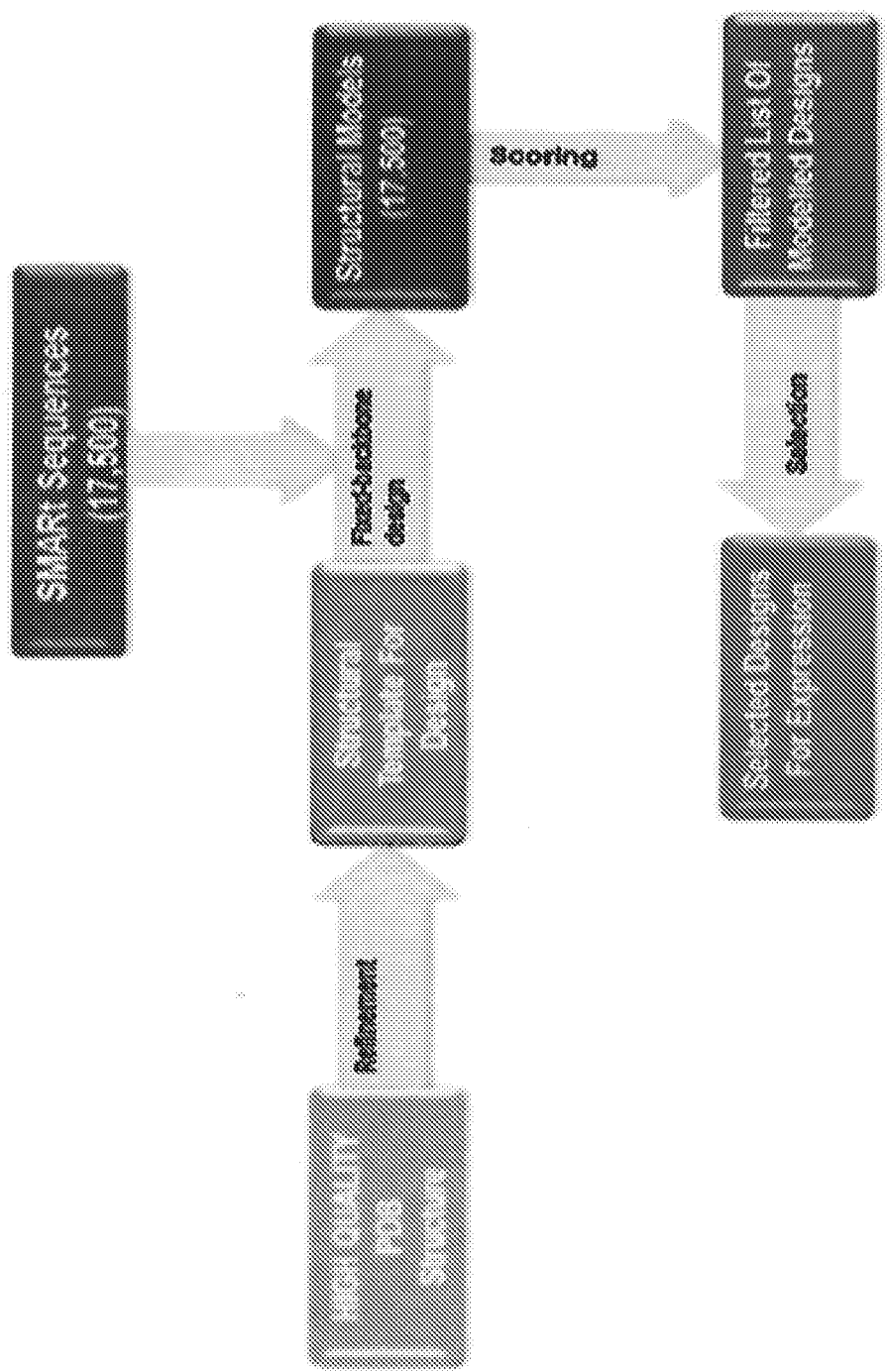
FIG. 19 demonstrates an exemplary workflow to input SMARt design sequences into a fixed backbone model and subsequently score and select the engineered antigenic polypeptides.

One aspect of the SMARt workflow for the design of mosaic antigens is structure-based molecular modeling to identify designs with conformational stability. Designs with conformational stability are then selected for experimental validation. A summary of the modeling and selection process is provided in FIG. 19. Three-dimensional coordinates of a high-quality structure of influenza A hemagglutinin (HA) were used as the template for modeling the structural backbones into which epitope repertoires were inserted (PDB ID: 1RVZ.).

Structure Modeling and Refinement

The mosaic sequences were checked for structural consistency using various structural bioinformatics tools known in the art. In brief, three dimensional structures of the designed sequences were constructed based on homology to related proteins of known structure. Per-residue energy scores as well as the overall conformational energy score of each model were calculated. Candidates with favorable energy scores were advanced into the final set of vaccination proteins. Per-residue energy scores were used to identify hot-spots (i.e., specific amino acid residues in the designed structures that had positive energy scores). In some embodiments, non-epitope hot-spot residues were substituted to release conformational strain and stabilize the structural fold of the designed sequences.

Figure 17:
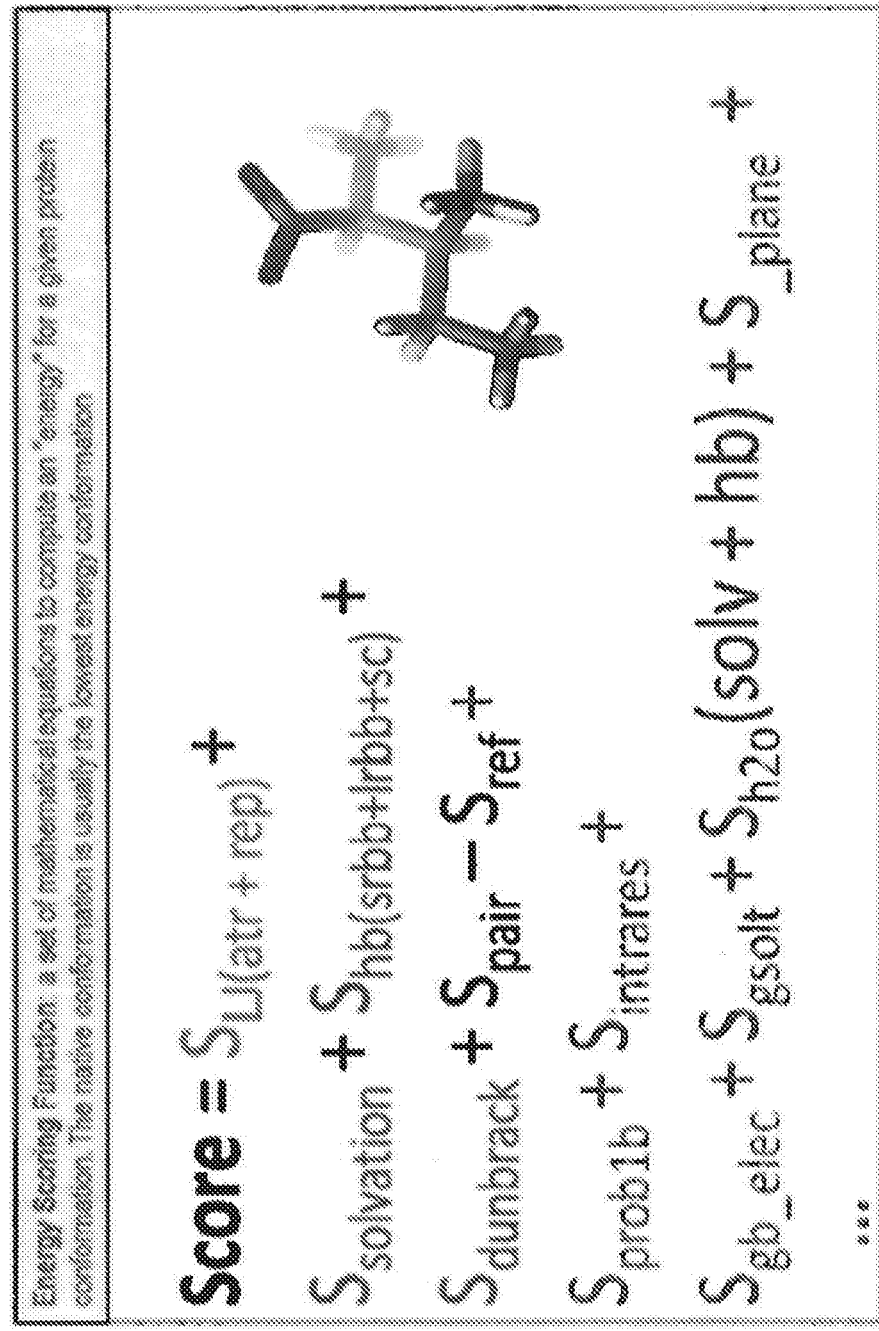
FIG. 17 demonstrates the Rosetta energy function used to score and/or select engineered mosaic antigenic polypeptides. The native conformation is usually the lowest energy conformation.
Figure 18:
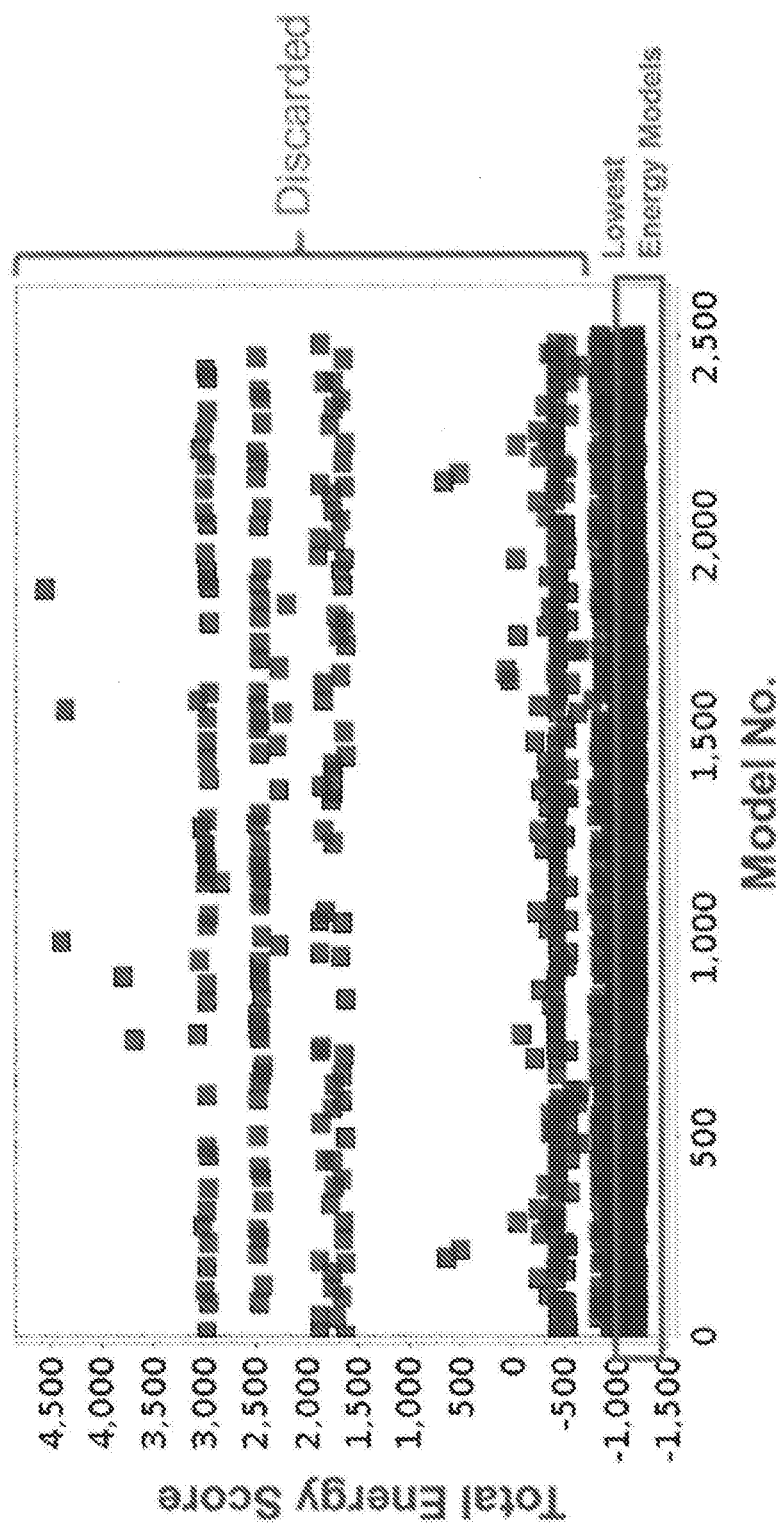
FIG. 18 shows an exemplary scatter plot of total energy score vs model number. The lowest energy models are selected for further screening, analysis, and development.

The insertion of epitopes into the 3D structure of the backbone molecule was performed using the design protocol of the Rosetta molecular modeling software version 3.1 (Simons et al. J. Mol. Biol. 1997 268:209-225; Leaver-Fay et al. Methods Enzymol. 2011 487:545-574). Following epitope insertion, the total energies of the resulting designed molecules were calculated using the Rosetta energy function showin in FIG. 17. Molecules with negative total energy scores were predicted to have a good probability of folding into stable proteins while those with positive energy scores were considered less likely to fold properly. FIG. 18 shows a scatter plot of energy score vs the model number of computationally predicted SMARt structural models. For clarity, only the top scoring 2,500 modeled structures are displayed on the plot.

Of the structural models generated, the lowest energy models were shortlisted for experimental testing, using a variety of screening methods. The short-listed candidates were prioritized for experimental validation to assess stable soluble expression, proper folding and immunogenicity. Thus, the approaches described above yielded novel hemagglutinin molecules for the Influenza A that do not match naturally occurring strains. These novel sequences are designed to provide broader coverage to naturally occurring strains than existing vaccine strains (including being cross-protective across the antigenically distinct subtypes). The resulting vaccine candidates can be further modified by targeted engineering of the sequence (including engineering glycosylation patterns, modifying stability or modifying specific epitopes).

Results

Using the methods described above, millions of combinations were generated and combinations with the highest coverage of the alignment were examined. Table 8 sets forth exemplary engineered HA polypeptides. Principal component analysis (PCA) was used to separate the H1N1 hemagglutinin sequences into eight unevenly distributed sub-family clusters (FIG. 9). Clusters 1, 3, and 4 were well represented and clusters 2, 7, and 8 were sparsely represented (Table 7).

Evaluating all possible combinations of unique epitope sequence patterns for multiple epitope sites is an N-P complete complexity computational problem. Sampling random combinations of cassettes enables the evaluation of a subset of all possible combinations. Millions of random combinations were generated and the combinations with the highest coverage of the alignment were examined. Top combinations identified are illustrated in Table 8.

TABLE 7

| Mosaic | Regions | Years | Clusters | Cluster 2 | Cluster 7 | Cluster 8 |
|---|---|---|---|---|---|---|
| HC578810 | 98% | 90% | 93% | 10/13 (77%) | 20/24 (84%) | 15/18 (84%) |
| HB949180 | 98% | 89% | 92% | 8/13 (61%) | 20/24 (84%) | 16/18 (89%) |
| ID316526 | 98% | 89% | 92% | 8/13 (61%) | 20/24 (84%) | 16/18 (89%) |
| JE56022 | 98% | 89% | 92% | 8/13 (61%) | 20/24 (84%) | 16/18 (89%) |

The SMARt approach enables the sampling of the known antigenic repertoires in mosaic sequences with promising potential for generating broadly protective vaccines.

TABLE 8

| Name | Backbone Sequence | SEQ ID NO: |
|---|---|---|
| SP1 | A/New Caledonia/20/1999 | 1 |
| SP2 | A/New Caledonia/20/1999 | 2 |
| SP3 | A/New Caledonia/20/1999 | 3 |
| SP4 | A/New Caledonia/20/1999 | 4 |
| SP5 | A/New Caledonia/20/1999 | 5 |
| SP6 | A/California/07/2009 | 6 |
| SP7 | A/California/07/2009 | 7 |
| SP8 | A/California/07/2009 | 8 |
| SP9 | A/California/07/2009 | 9 |
| SP10 | A/California/07/2009 | 10 |

SMARt Design Guided Engineered Soluble Recombinant HA (rHA)

Fifty soluble versions of the Influenza A SMARt HA proteins have been synthesized, expressed and purified from HEK293 cells using the protein expression and purification platform (PEPP). SMARt HA designs were engineered as full-length trimeric HA proteins. Designs were modified for expression of soluble recombinant protein by replacement of the transmembrane region and cytoplasmic domain with thrombin cleavage site, foldon trimerization domain and his-tag. Approximately 50% of the novel designs were purified as soluble versions.

In Vitro Recognition of PEPP Influenza A rHAs

Purified, soluble Influenza A SMARt HAs are evaluated for their ability to bind Influenza A specific monoclonal antibodies. Using the ForteBio Octet system, verification of binding to conformational epitopes is performed at a single concentration. Several of these engineered mosaic antigens are able to bind Influenza A specific monoclonal antibodies indicating that the molecules are well-folded (and likely functional).

Example 2

In Vivo Efficacy of Engineered Mosaic HA Polypeptides

This Example illustrates that engineered HA polypeptide made in accordance with Example 1 elicited immune responses in the form of broad antibody responses against several influenza strains.

Preparation of Virus-Like Particles (VLPs) Containing Engineered Mosaic Hemagglutinins (HAs)

Influenza VLPs were prepared by three-plasmid transient transfection of HEK293T cells in serum-free Freestyle293 medium. Plasmids encoding engineered mosaic Influenza HA polypeptide sequence as well as those for NA, and HIVgag were mixed at 1:1:1 ratio and used to transiently transfect the HEK293T cells. Culture supernatant was harvested 120 hours post-transfection and VLPs in the supernatant were pelleted by ultracentrifugation over a 20% sucrose cushion and resuspended in PBS.

Immunization of Mice with VLPs Expressing Engineered Mosaic HAs

To assess immunogenicity of engineered mosaic HA designs, groups of 6-8 week old female BALB/c mice were immunized with 5 μg of influenza VLPs or vehicle alone (PBS). All immunizations were formulated as emulsions with an oil-in-water adjuvant, and were delivered subcutaneously in a total volume of 100 μl. Each group received an identical booster dose 21 days after the initial immunization. Pre-immune and post-immune serum was collected from each animal on days 0 and 35, respectively. Serum pools used for analysis were prepared by mixing equal volumes of serum from each animal within a group.

Hemagglutination Inhibition (HAI) Assay

Figure 6:
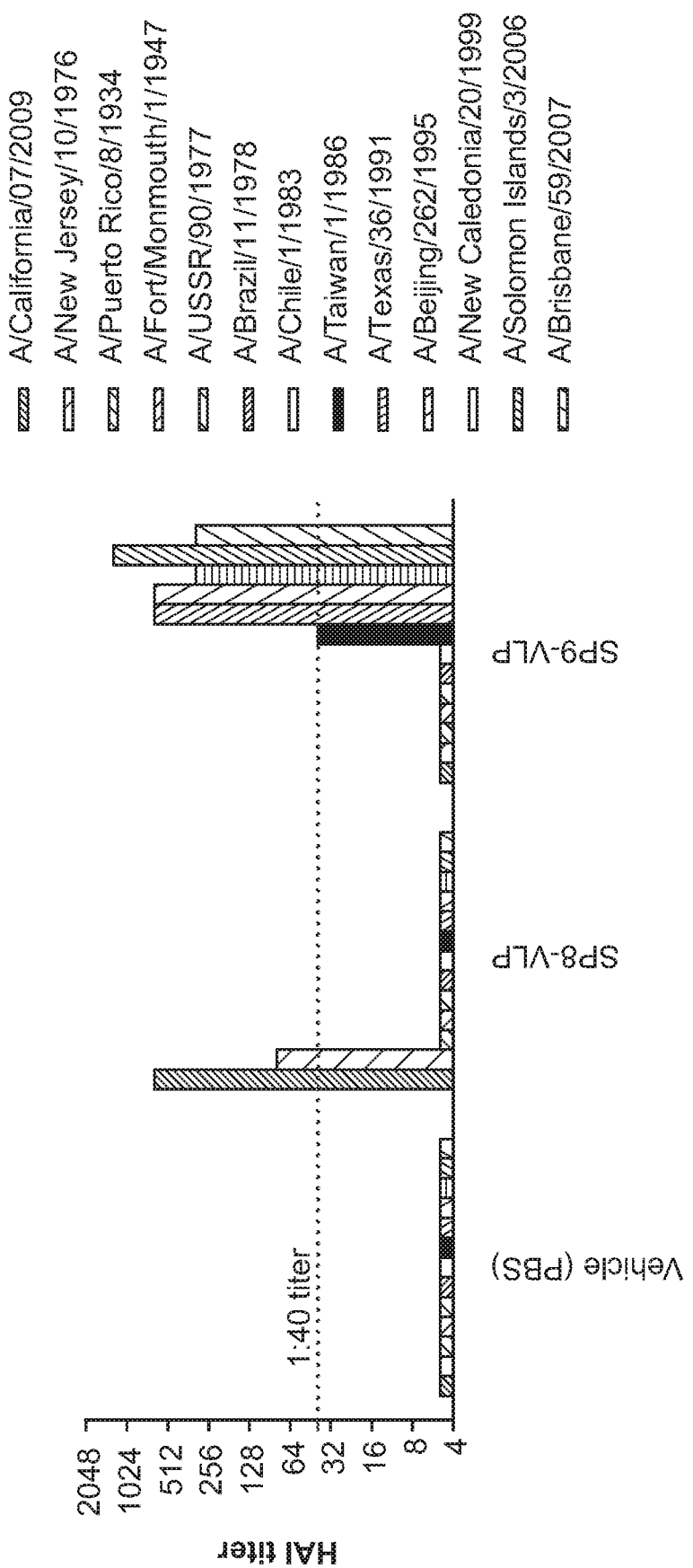
FIG. 6 shows representative serum titer induced against H1N1 influenza strains as measured in a hemagglutination inhibition (HAI) assay for selected engineered VLPs. Animals were immunized as described in Example 2 and serum collected on day 35 (14 days after boosting dose) was analyzed for its ability to inhibit hemagglutination mediated by various H1N1 influenza strains. Titer is defined as the maximum serum dilution resulting in complete inhibition of hemagglutination in 50% of the wells assayed. The strains selected for analysis included World Health Organization-recommended H1N1 vaccine strains since 1977: A/California/07/2009, A/USSR/90/1977, A/Brazil/11/1978, A/Chile/i/1983, A/Taiwan/1/1986 (A/Singapore/6/1986-like), A/Beijing/262/1995, A/New Caledonia/20/1999, A/Solomon Island/3/2006, and A/Brisbane/59/2007. Other representative historical H1N1 influenza strains included in HAI assays include: A/New Jersey/10/1976, A/Puerto Rico/8/1934, A/Fort Monmouth/i/1947, and A/Texas/36/1991. Each bar represents the virus-specific serum HAI titer induced by selected influenza VLPs or vehicle. The dotted line on the graph represents a 1:40 HAI titer, which is known as the minimum HAI titer required for protection against a given influenza strain.
Figure 20:
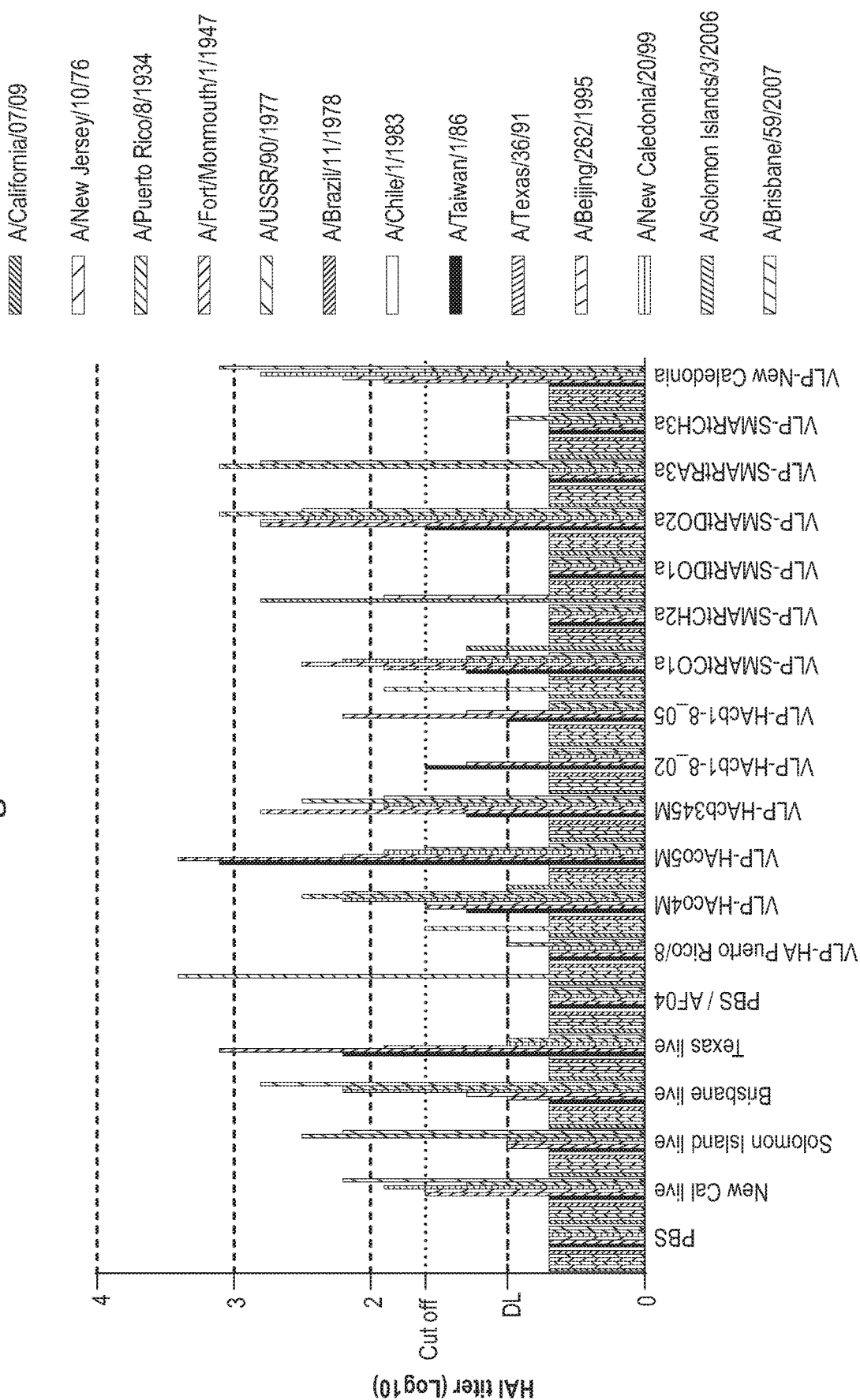
FIG. 20 shows representative serum titer induced against H1N1 influenza strains as measured in a hemagglutination inhibition (HAI) assay for selected engineered VLPs. Animals were immunized as described in Example 2 and serum collected on day 35 (14 days after boosting dose) was analyzed for its ability to inhibit hemagglutination included in multi-specific antibodies formed from antibody fragments. Those skilled in the art will appreciate that the term "antibody fragment" does not imply and is not restricted to any particular mode of generation. An antibody fragment may be produced through use of any appropriate methodology, including but not limited to cleavage of an intact antibody, chemical synthesis, recombinant production, etc. As is known in the art, intact antibodies as produced in nature are approximately 150 kD tetrameric agents comprised of two identical heavy chain polypeptides (about 50 kD each) and two identical light chain polypeptides (about 25 kD each) that associate with each other into what is commonly referred to as a "Y-shaped" structure. Each heavy chain is comprised of at least four domains (each about 110 amino acids long)—an amino-terminal variable ($V_H$) domain (located at the tips of the Y structure), followed by three constant domains: $C_H1$, $C_H2$, and the carboxy-terminal $C_H3$ (located at the base of the Y's stem). A short region, known as the "switch", connects the heavy chain variable and constant regions. The "hinge" connects $C_H2$ and $C_H3$ domains to the rest of the antibody. Two disulfide bonds in this hinge region connect the two heavy chain polypeptides to one another in an intact antibody. Each light chain is comprised of two domains—an amino-terminal variable ($V_L$) domain, followed by a carboxy-terminal constant ($C_L$) domain, separated from one another by another "switch". Intact antibody tetramers are comprised of two heavy chain-light chain dimers in which the heavy and light chains are linked to one another by a single disulfide bond; two other disulfide bonds connect the heavy chain hinge regions to one another, so that the dimers are connected to one another and the tetramer is formed. Naturally-produced antibodies are also glycosylated, typically on the $C_H2$ domain. Each domain in a natural antibody has a structure characterized by an "immunoglobulin fold" formed from two beta sheets (e.g., 3-, 4-, or 5-stranded sheets) packed against each other in a compressed antiparallel beta barrel. Each variable domain contains three hypervariable loops known as "complement determining regions" (CDR1, CDR2, and CDR3) and four somewhat invariant "framework" regions (FR1, FR2, FR3, and FR4). When natural antibodies fold, the FR regions form the beta sheets that provide the structural framework for the domains, and the CDR loop regions from both the heavy and light chains are brought together in three-dimensional space so that they create a single hypervariable antigen binding site located at the tip of the Y structure. Amino acid sequence comparisons among antibody polypeptide chains have defined two light chain ($\kappa$ and $\lambda$) classes, several heavy chain (e.g., $\mu$, $\gamma$, $\alpha$, $\epsilon$, $\delta$) classes, and certain heavy chain subclasses ($\alpha 1$, $\alpha 2$, $\gamma 1$, $\gamma 2$, $\gamma 3$, and $\gamma 4$). Antibody classes (IgA [including IgA1, IgA2], IgD, IgE, IgG [including IgG1, IgG2, IgG3, IgG4], IgM) are defined based on the class of the utilized heavy chain sequences. For purposes of the present invention, in certain embodiments, any polypeptide or complex of polypeptides that includes sufficient immunoglobulin domain sequences as found in natural antibodies can be referred to and/or used as an "antibody", whether such polypeptide is naturally produced (e.g., generated by an organism reacting to an antigen), or produced by recombinant engineering, chemical synthesis, or other artificial system or methodology. In some embodiments, an antibody is monoclonal; in some embodiments, an antibody is polyclonal. In some embodiments, an antibody has constant region sequences that are characteristic of mouse, rabbit, primate, or human antibodies. In some embodiments, an antibody sequence elements are humanized, primatized, chimeric, etc., as is known in the art. Moreover, the term "antibody" as used herein, will be understood to encompass (unless otherwise stated or clear from context) can refer in appropriate embodiments to any of the art-known or developed constructs or formats for capturing antibody structural and functional features in alternative presentation. For example, in some embodiments, the term can refer to bi- or other multi-specific (e.g., zybodies, etc.) antibodies, Small Modular ImmunoPharmaceuticals ("SMIPs™"), single chain antibodies, camelid antibodies, and/or antibody fragments. In some embodiments, an antibody may lack a covalent modification (e.g., attachment of a glycan) that it would have if produced naturally. In some embodiments, an antibody may contain a covalent modification (e.g., attachment of a glycan, a payload [e.g., a detectable moiety, a therapeutic moiety, a catalytic moiety, etc.], or other pendant group [e.g., poly-ethylene glycol, etc.]).

Replicate serial dilutions of pooled serum from each group were mixed with 4 hemagglutination units of the indicated virus and incubated at room temperature for 30 minutes in a round bottom plate. Each serum/virus mixture was then mixed with an equal volume of 0.5% turkey erythrocytes in saline. The plates were scored when control wells lacking serum demonstrated complete hemagglutination (~30 min). The HAI titer was defined as the maximum serum dilution resulting in complete inhibition of hemagglutination in 50% of the wells tested. FIG. 6 sets forth representative serum HAI titer induced against H1N1 influenza strains for engineered mosaic VLPs. FIG. 20 sets forth representative serum HAI titer induced against H1N1 influenza strains for engineered mosaic VLPs.

Microneutralization (MN) Assay

Figure 7:
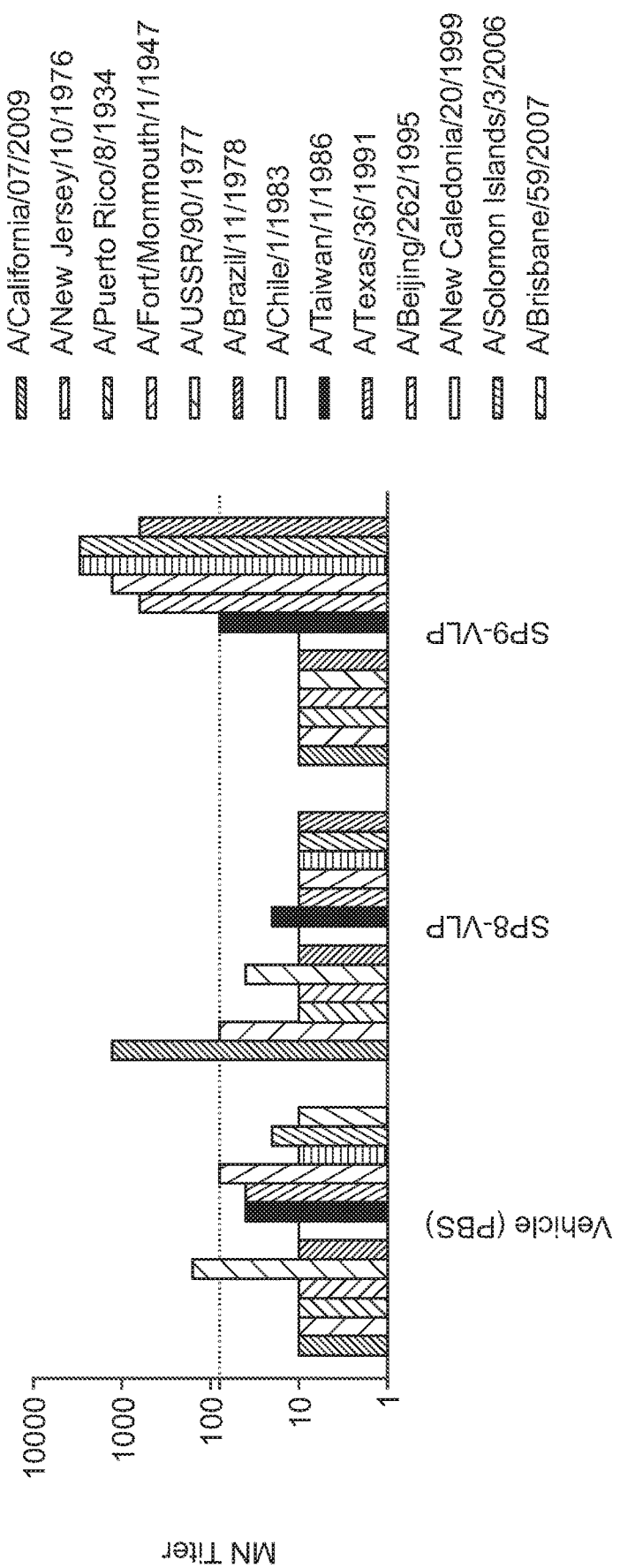
FIG. 7 shows representative serum titer induced against H1N1 influenza strains as measured in a microneutralization (MN) assay for selected engineered VLPs. Animals were immunized as described in Example 2 and serum collected on day 35 (14 days after the boosting dose) was analyzed for its ability to block infection with various H1N1 influenza strains. The MN titer is defined as the maximum serum dilution resulting in complete inhibition of infection with the indicated influenza strain in 50% of the wells tested. Each bar represents the virus-specific serum MN titer induced by selected influenza VLPs or vehicle. The dotted line on the graph represents a 1:80 MN titer, which is suggested is a minimum titer required for protection against influenza challenge.
Figure 21:
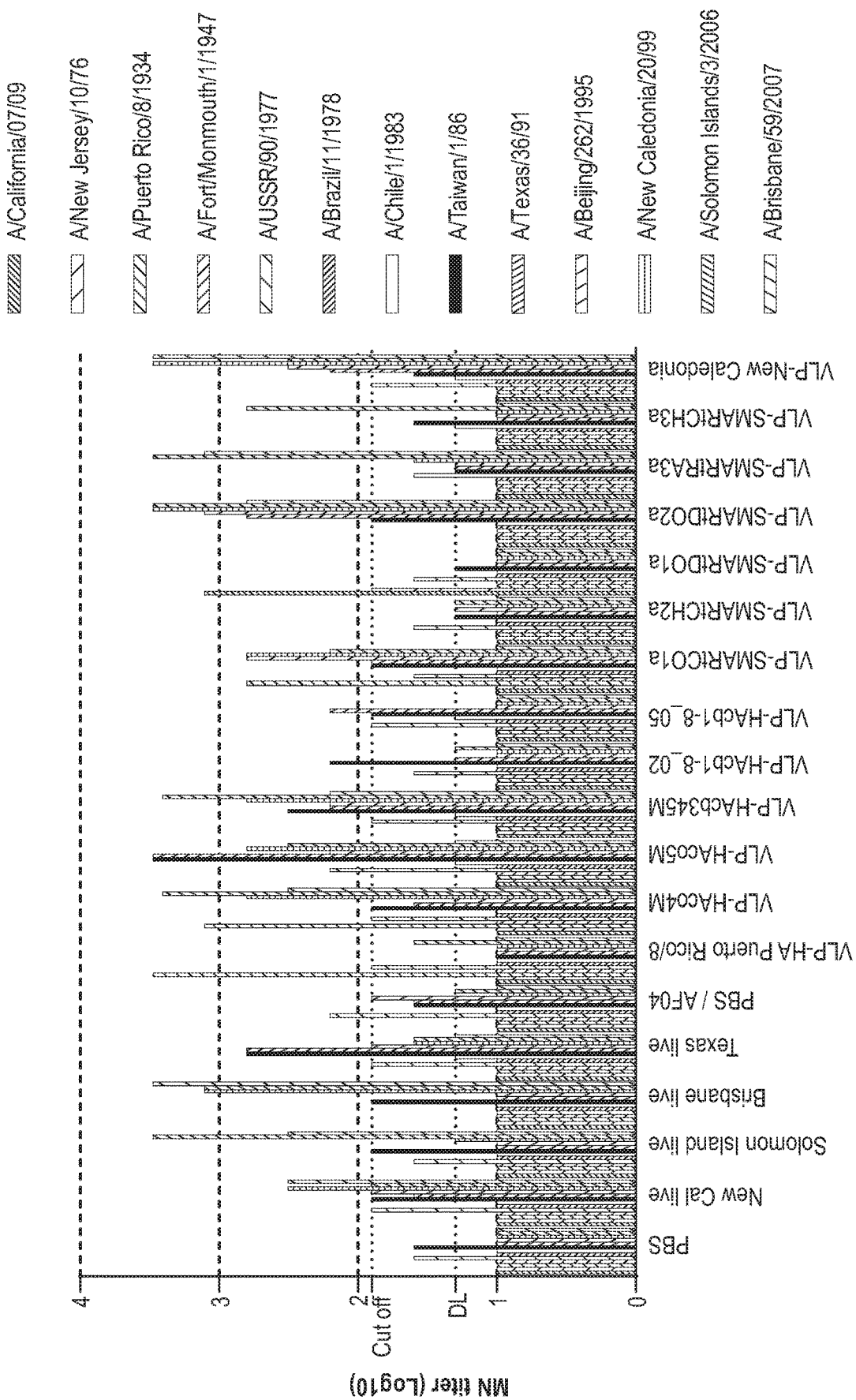

Replicate serial dilutions of pooled serum from each group were mixed with 100 50% tissue culture infectious doses (TCID50) of the indicated virus and incubated at 37° C. for one hour. Each serum/virus mixture was then added to confluent monolayers of madin darby canine kidney (MDCK) cells and incubated at 37° C. for 24 hrs. The monolayers were then fixed and infected wells were identified based on ELISA detection of influenza nucleoprotein. The MN titer was defined as the highest dilution of serum resulting in complete neutralization of virus infection in 50% of the wells tested. FIG. 7 sets forth representative serum MN titer induced against H1N1 influenza strains for engineered mosaic VLPs. FIG. 21 sets forth representative serum MN titer induced against H1N1 influenza strains for engineered mosaic VLPs.

Results

Taken together, these data demonstrate that engineered HA polypeptides as described herein promote broad immunity against H1N1 influenza strains. These exemplary HA polypeptides were developed using a novel computational strategy to create mosaic HA antigens based on conserved repertoires, referred to as SMARt. Exemplary HA polypeptides SP8 and SP9 (Table 8) were presented in the context of an HIVgag VLP to perform immunogenicity studies in murine animals. As shown in FIGS. 6 and 7, exemplary engineered mosaic HA polypeptides induced antibody responses predicted to provide protection against both A/California/07/2009 (the currently circulating H1N1 strain) as well as a historical swine flu strain, A/New Jersey/10/1976. More importantly, as shown in FIGS. 6 and 7, SP9 induced a broad antibody response, with significant titers induced against vaccine strains dating back to 1986. These data suggest that a vaccine utilizing the engineered mosaic design (e.g., SP9) may have been sufficient for protection from H1N1 strains circulating between the years of 1986 and 2007. Further, a combined immunization incorporating both SP8 and SP9 HA designs would potentially be effective against all H1N1 viruses that have been in circulation since 1986. Thus, the engineered mosaic HA designs as described herein provide candidate HA polypeptides for use in a universal H1N1 vaccine that can be used alone or in combination to induce immunity against a broad array of H1N1 viruses.

Having thus described several aspects of at least one embodiment of this invention, it is to be appreciated that various alterations, modifications, and improvements will readily be apparent to those skilled in the art. Such alterations, modifications, and improvements are intended to be part of this disclosure, and are intended to be within the spirit and scope of the invention. Accordingly, the foregoing description and drawings are by way of example only and the invention is described in detail by the claims that follow.

EQUIVALENTS

Use of ordinal terms such as "first," "second," "third," etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

The articles "a" and "an" as used herein in the specification and in the claims, unless clearly indicated to the contrary, should be understood to include the plural referents. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention also includes embodiments in which more than one, or the entire group members are present in, employed in, or otherwise relevant to a given product or process. Furthermore, it is to be understood that the invention encompasses all variations, combinations, and permutations in which one or more limitations, elements, clauses, descriptive terms, etc., from one or more of the listed claims is introduced into another claim dependent on the same base claim (or, as relevant, any other claim) unless otherwise indicated or unless it would be evident to one of ordinary skill in the art that a contradiction or inconsistency would arise. Where elements are presented as lists, (e.g., in Markush group or similar format) it is to be understood that each subgroup of the elements is also disclosed, and any element(s) can be removed from the group. It should be understood that, in general, where the invention, or aspects of the invention, is/are referred to as comprising particular elements, features, etc., certain embodiments of the invention or aspects of the invention consist, or consist essentially of, such elements, features, etc. For purposes of simplicity those embodiments have not in every case been specifically set forth in so many words herein. It should also be understood that any embodiment or aspect of the invention can be explicitly excluded from the claims, regardless of whether the specific exclusion is recited in the specification. The publications, websites and other reference materials referenced herein to describe the background of the invention and to provide additional detail regarding its practice are hereby incorporated by reference.

We claim:

1. A method of engineering a mosaic influenza hemagglutinin (HA) polypeptide, comprising
   aligning HA amino acid sequences from multiple circulating strains of a particular type and/or subtype of influenza virus to generate an alignment;
   identifying positions of amino acids corresponding to epitopes and antigenic regions, or defined set of residue positions;
   compiling amino acid residues across the alignment at the identified positions for epitopes and antigenic regions, or defined set of residue positions thereby generating antigenic repertoires;
   defining a set of amino acid sequence patterns within the antigenic repertoires for each epitope and antigenic region, or defined set of residue positions, wherein each amino acid sequence pattern in the set is represented only once;
   selecting one or more sequences based on the defined amino acid sequence patterns in the set for each epitope or antigenic region, or defined set of residue positions, thereby resulting in combinations of selected sequences for epitopes and antigenic regions or defined set of residue positions across the alignment according to pre-determined criteria; and
   inserting selected sequences into corresponding locations in a structural backbone of HA, thereby generating engineered mosaic influenza HA polypeptides, wherein the engineered mosaic influenza HA polypeptides are distinct from naturally circulating strains; and
   evaluating each of the engineered mosaic influenza HA polypeptides based on conformational stability and breadth of coverage across naturally occurring strains.

2. The method of claim 1, wherein the particular type and/or subtype of influenza virus is a type A influenza virus.

3. The method of claim 1, wherein the particular type and/or subtype of influenza virus is a type B influenza virus.

4. A method of engineering a mosaic influenza neuraminidase (NA) polypeptide, comprising:
   aligning NA amino acid sequences from multiple circulating strains of a particular type and/or subtype of influenza virus to generate an alignment;
   identifying positions of amino acids corresponding to epitopes and antigenic regions or defined set of residue positions;
   compiling amino acid residues across the alignment at the identified positions for epitopes and antigenic regions, or defined set of residue positions thereby generating antigenic repertoires;
   defining a set of amino acid sequence patterns within the antigenic repertoires for each epitope and antigenic region, or defined set of residue positions, wherein each amino acid sequence pattern in the set is represented only once;
   selecting one or more sequences based on the defined amino acid sequence patterns in the set for each epitope or antigenic region, or defined set of residue positions, thereby resulting in combinations of selected sequences for epitopes and antigenic regions, or defined set of residue positions across the alignment according to pre-determined criteria; and
   inserting selected sequences into corresponding locations in a structural backbone of NA, thereby generating engineered mosaic influenza NA polypeptides, wherein the engineered mosaic influenza NA polypeptides are distinct from naturally circulating strains; and
   evaluating each of the engineered mosaic influenza NA polypeptides based on conformational stability and breadth of coverage across naturally occurring strains.

5. The method of claim 1, wherein evaluating the conformational stability comprises calculating the folding energy of each of the engineered mosaic influenza HA polypeptides and selecting the engineered polypeptides that fold into a native-like conformation.

6. The method of claim 1, wherein the selecting step further comprises ranking the selected sequences by sequence identity, geographical location and isolation date of the type or subtype of influenza virus.

7. The method of claim 1, wherein the sequences are selected at random.

8. The method of claim 1, wherein the sequences are selected so the mosaic influenza HA polypeptide elicits a broadly neutralizing immune response against the multiple circulating influenza strains.

9. The method of claim 1, wherein prior to the selecting step, the amino acid sequence patterns in the set are weighted by their frequency of occurrence.

10. The method of claim 1, wherein the aligning obtaining step further comprises identifying redundant sequences by screening the HA amino acid sequences for those with greater than 99.9% sequence identity, and removing all but one of the redundant sequences.

11. The method of claim 4, wherein evaluating the conformational stability comprises calculating the folding energy of each of the engineered mosaic influenza NA polypeptides and selecting the engineered polypeptides that fold into a native-like conformation.

12. The method of claim 4, wherein the selecting step further comprises ranking the selected sequences by sequence identity, geographical location and isolation date of the type or subtype of influenza virus.

13. The method of claim 4, wherein the sequences are selected at random.

14. The method of claim 4, wherein the sequences are selected so the mosaic influenza NA polypeptide elicits a broadly neutralizing immune response against the multiple circulating influenza strains.

15. The method of claim 4, wherein prior to the selecting step, amino acid sequence patterns in the set are weighted by their frequency of occurrence.

16. The method of claim 4, wherein the aligning step further comprises identifying redundant sequences by screening the NA amino acid sequences for those with greater than 99.9% sequence identity, and removing all but one of the redundant sequences.

17. The method of claim 1, wherein the selecting step comprises generating a consensus sequence based on the defined amino acid sequence patterns in the set for each epitope or antigenic region.

18. The method of claim 17, wherein the consensus sequence for each epitope or antigenic region is selected.

19. The method of claim 1, wherein dominant sequences for each epitope or antigenic region are selected.

20. The method of claim 1, wherein the sequences for epitopes or antigenic regions are selected such that combination of the selected sequences maximize breadth of coverage across naturally occurring strains by year, geography and sequence cluster.

21. The method of claim 1, wherein more than 1000 HA amino acid sequences from multiple circulating influenza strains are aligned.

22. The method of claim 1, wherein the selected sequences result in millions of combinations for epitopes and antigenic regions across the alignment.

23. The method of claim 4, wherein the selecting step comprises generating a consensus sequence based on the defined amino acid sequence patterns in the set for each epitope or antigenic region.

24. The method of claim 23, wherein the consensus sequence is selected.

25. The method of claim 4, wherein dominant sequences for each epitope or antigenic region are selected.

26. The method of claim 4, wherein the sequences for epitopes or antigenic regions are selected such that combination of the selected sequences maximize breadth of coverage across naturally occurring strains by year, geography and sequence cluster.

27. The method of claim 4, wherein more than 1000 NA amino acid sequences from multiple circulating influenza strains are aligned.

28. The method of claim 4, wherein the selected sequences result in millions of combinations for epitopes and antigenic regions across the alignment.

\* \* \* \* \*

UNITED STATES PATENT AND TRADEMARK OFFICE
CERTIFICATE OF CORRECTION

PATENT NO. : 10,584,148 B2
APPLICATION NO. : 15/578880
DATED : March 10, 2020
INVENTOR(S) : Strugnell et al.

Page 1 of 1

It is certified that error appears in the above-identified patent and that said Letters Patent is hereby corrected as shown below:

In the Claims

Claim 10, Column 163, Line 10:
Delete the word "obtaining"

Signed and Sealed this
Fifth Day of May, 2020

Andrei Iancu
*Director of the United States Patent and Trademark Office*

SEQUENCE LISTING

<160> NUMBER OF SEQ ID NOS: 173

<210> SEQ ID NO 1
<211> LENGTH: 565
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 1

```
Met Lys Ala Lys Leu Leu Val Leu Leu Cys Thr Phe Thr Ala Thr Tyr
1               5                   10                  15

Ala Asp Thr Ile Cys Ile Gly Tyr His Ala Asn Asn Ser Thr Asp Thr
                20                  25                  30

Val Asp Thr Val Leu Glu Lys Asn Val Thr Val Thr His Ser Val Asn
            35                  40                  45

Leu Leu Glu Asp Ser His Asn Gly Lys Leu Cys Lys Leu Lys Gly Ile
        50                  55                  60

Ala Pro Leu Gln Leu Gly Lys Cys Ser Val Ala Gly Trp Ile Leu Gly
65                  70                  75                  80

Asn Pro Glu Cys Glu Ser Leu Ser Thr Ala Ser Ser Trp Ser Tyr Ile
                85                  90                  95

Val Glu Thr Ser Asn Pro Glu Asn Gly Thr Cys Tyr Pro Gly Tyr Phe
                100                 105                 110

Ala Asp Tyr Glu Glu Leu Arg Glu Gln Leu Ser Ser Val Ser Ser Phe
            115                 120                 125

Glu Arg Phe Glu Ile Phe Pro Lys Glu Ser Ser Trp Pro Asn His Thr
        130                 135                 140

Val Thr Gly Val Thr Ala Ser Cys Ser His Ala Gly Lys Ser Ser Phe
145                 150                 155                 160

Tyr Arg Asn Leu Leu Trp Leu Thr Gly Lys Asn Gly Ser Tyr Pro Asn
                165                 170                 175

Leu Ser Lys Ser Tyr Val Asn Asn Lys Glu Lys Glu Val Leu Val Leu
            180                 185                 190

Trp Gly Val His His Pro Ser Asn Ile Gly Asp Gln Gln Thr Leu Tyr
        195                 200                 205

Gln Thr Glu Asn Ala Tyr Val Ser Val Val Ser Ser Arg Tyr Ser Arg
    210                 215                 220

Arg Phe Thr Pro Glu Ile Ala Lys Arg Pro Lys Val Arg Asp Gln Glu
225                 230                 235                 240

Gly Arg Met Asn Tyr Tyr Trp Thr Leu Val Glu Pro Gly Asp Thr Ile
                245                 250                 255

Ile Phe Glu Ala Asn Gly Asn Leu Ile Ala Pro Trp Tyr Ala Phe Ala
            260                 265                 270

Leu Ser Arg Gly Phe Gly Ser Gly Ile Ile Thr Ser Asn Ala Pro Val
        275                 280                 285

His Asp Cys Asn Thr Lys Cys Gln Thr Pro Gln Gly Ala Ile Asn Ser
    290                 295                 300

Ser Leu Pro Phe Gln Asn Val His Pro Val Thr Ile Gly Glu Cys Pro
305                 310                 315                 320

Lys Tyr Val Arg Ser Ala Lys Leu Arg Met Ala Thr Gly Leu Arg Asn
                325                 330                 335

Ile Pro Ser Ile Gln Ser Arg Gly Leu Phe Gly Ala Ile Ala Gly Phe
            340                 345                 350
```

```
Ile Glu Gly Gly Trp Thr Gly Met Val Asp Gly Trp Tyr Gly Tyr His
        355                 360                 365

His Gln Asn Glu Gln Gly Ser Gly Tyr Ala Ala Asp Gln Lys Ser Thr
    370                 375                 380

Gln Asn Ala Ile Asp Gly Ile Thr Asn Lys Val Asn Ser Val Ile Glu
385                 390                 395                 400

Lys Met Asn Thr Gln Phe Thr Ala Val Gly Lys Glu Phe Asn Lys Leu
                405                 410                 415

Glu Arg Arg Met Glu Asn Leu Asn Lys Lys Val Asp Asp Gly Phe Leu
            420                 425                 430

Asp Ile Trp Thr Tyr Asn Ala Glu Leu Leu Val Leu Leu Glu Asn Glu
        435                 440                 445

Arg Thr Leu Asp Phe His Asp Ser Asn Val Lys Asn Leu Tyr Glu Lys
    450                 455                 460

Val Lys Ser Gln Leu Lys Asn Asn Ala Lys Glu Ile Gly Asn Gly Cys
465                 470                 475                 480

Phe Glu Phe Tyr His Lys Cys Asn Asn Thr Cys Met Glu Ser Val Lys
                485                 490                 495

Asn Gly Thr Tyr Asp Tyr Pro Lys Tyr Ser Glu Glu Ser Lys Leu Asn
            500                 505                 510

Arg Glu Lys Ile Asp Gly Val Lys Leu Glu Ser Met Gly Val Tyr Gln
        515                 520                 525

Ile Leu Ala Ile Tyr Ser Thr Val Ala Ser Ser Leu Val Leu Leu Val
    530                 535                 540

Ser Leu Gly Ala Ile Ser Phe Trp Met Cys Ser Asn Gly Ser Leu Gln
545                 550                 555                 560

Cys Arg Ile Cys Ile
            565

<210> SEQ ID NO 2
<211> LENGTH: 565
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 2

Met Lys Ala Lys Leu Leu Val Leu Leu Cys Thr Phe Thr Ala Thr Tyr
1               5                   10                  15

Ala Asp Thr Ile Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asp Ser His Asn Gly Lys Leu Cys Leu Leu Lys Gly Ile
    50                  55                  60

Ala Pro Leu Gln Leu Gly Asn Cys Ser Val Ala Gly Trp Ile Leu Gly
65                  70                  75                  80

Asn Pro Glu Cys Glu Leu Leu Ser Thr Lys Ser Ser Trp Ser Tyr Ile
                85                  90                  95

Val Glu Thr Pro Asn Pro Glu Asn Gly Thr Cys Tyr Pro Gly Tyr Phe
            100                 105                 110

Ala Asp Tyr Glu Glu Leu Arg Glu Gln Leu Ser Ser Val Ser Ser Phe
        115                 120                 125
```

-continued

Glu Arg Phe Glu Ile Phe Pro Lys Glu Ser Ser Trp Pro Asn His Asp
130                 135                 140

Val Thr Gly Val Ser Ala Ser Cys Ser His Asn Gly Ala Ser Ser Phe
145                 150                 155                 160

Tyr Arg Asn Leu Leu Trp Leu Thr Lys Asn Asn Leu Tyr Pro Asn
    165                 170                 175

Leu Ser Lys Ser Tyr Ala Asn Asn Lys Gly Lys Glu Val Leu Val Leu
        180                 185                 190

Trp Gly Val His His Pro Ser Thr Ile Ala Asp Gln Gln Thr Leu Tyr
            195                 200                 205

His Thr Glu Asn Ala Tyr Val Ser Val Val Ser Ser His Tyr Ser Arg
210                 215                 220

Arg Phe Thr Pro Glu Ile Ala Ile Arg Pro Lys Val Arg Asp Gln Glu
225                 230                 235                 240

Gly Arg Ile Asn Tyr Tyr Trp Thr Leu Leu Glu Pro Gly Asp Thr Ile
                245                 250                 255

Ile Phe Glu Ala Asn Gly Asn Leu Ile Ala Pro Trp Tyr Ala Phe Ala
            260                 265                 270

Leu Ser Arg Gly Phe Gly Ser Gly Ile Ile Thr Ser Asn Ala Pro Met
        275                 280                 285

Asp Glu Cys Asn Thr Thr Cys Gln Thr Pro Gln Gly Ala Ile Asn Ser
290                 295                 300

Ser Leu Pro Phe Gln Asn Val His Pro Val Thr Ile Gly Glu Cys Pro
305                 310                 315                 320

Lys Tyr Val Arg Ser Ala Lys Leu Arg Met Val Thr Gly Leu Arg Asn
                325                 330                 335

Ile Pro Ser Ile Gln Ser Arg Gly Leu Phe Gly Ala Ile Ala Gly Phe
            340                 345                 350

Ile Glu Gly Gly Trp Thr Gly Met Val Asp Gly Trp Tyr Gly Tyr His
        355                 360                 365

His Gln Asn Glu Gln Gly Ser Gly Tyr Ala Ala Asp Leu Lys Ser Thr
370                 375                 380

Gln Asn Ala Ile Asn Gly Ile Thr Asn Lys Val Asn Ser Val Ile Glu
385                 390                 395                 400

Lys Met Asn Thr Gln Phe Thr Ala Val Gly Lys Glu Phe Asn Lys Leu
                405                 410                 415

Glu Arg Arg Met Glu Asn Leu Asn Lys Lys Val Asp Asp Gly Phe Leu
            420                 425                 430

Asp Ile Trp Thr Tyr Asn Ala Glu Leu Leu Val Leu Leu Glu Asn Glu
        435                 440                 445

Arg Thr Leu Asp Phe His Asp Ser Asn Val Lys Asn Leu Tyr Glu Lys
450                 455                 460

Val Lys Ser Gln Leu Lys Asn Asn Ala Lys Glu Ile Gly Asn Gly Cys
465                 470                 475                 480

Phe Glu Phe Tyr His Lys Cys Asn Asn Glu Cys Met Glu Ser Val Lys
                485                 490                 495

Asn Gly Thr Tyr Asp Tyr Pro Lys Tyr Ser Glu Glu Ser Lys Leu Asn
            500                 505                 510

Arg Glu Lys Ile Asp Gly Val Lys Leu Glu Ser Met Gly Val Tyr Gln
        515                 520                 525

Ile Leu Ala Ile Tyr Ser Thr Val Ala Ser Ser Leu Val Leu Leu Val
530                 535                 540

Ser Leu Gly Ala Ile Ser Phe Trp Met Cys Ser Asn Gly Ser Leu Gln

Cys Arg Ile Cys Ile
            565

<210> SEQ ID NO 3
<211> LENGTH: 565
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 3

Met Lys Ala Lys Leu Leu Val Leu Leu Cys Thr Phe Thr Ala Thr Tyr
1               5                   10                  15

Ala Asp Thr Ile Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asp Ser His Asn Gly Lys Leu Cys Lys Leu Lys Gly Ile
    50                  55                  60

Ala Pro Leu Gln Leu Gly Lys Cys Ser Val Ala Gly Trp Ile Leu Gly
65                  70                  75                  80

Asn Pro Glu Cys Glu Ser Leu Ser Thr Ala Ser Ser Trp Ser Tyr Ile
                85                  90                  95

Val Glu Thr Ser Ser Pro Asp Asn Gly Thr Cys Tyr Pro Gly Tyr Phe
            100                 105                 110

Ala Asp Tyr Glu Glu Leu Arg Glu Gln Leu Ser Ser Val Ser Ser Phe
        115                 120                 125

Glu Arg Phe Glu Ile Phe Pro Lys Thr Ser Ser Trp Pro Asn His Asp
    130                 135                 140

Ser Asn Gly Val Thr Ala Ser Cys Pro His Ala Gly Ala Lys Ser Phe
145                 150                 155                 160

Tyr Arg Asn Leu Leu Trp Leu Val Lys Lys Gly Asn Ser Tyr Pro Lys
                165                 170                 175

Leu Ser Lys Ser Tyr Ile Asn Asp Lys Gly Lys Glu Val Leu Val Leu
            180                 185                 190

Trp Gly Val His His Pro Ser Thr Ser Ala Asp Gln Gln Ser Leu Tyr
        195                 200                 205

Gln Asn Ala Asn Ala Tyr Val Ser Val Thr Ser Arg Tyr Ser Arg
    210                 215                 220

Arg Phe Thr Pro Glu Ile Ala Ile Arg Pro Lys Val Arg Asp Gln Glu
225                 230                 235                 240

Gly Arg Met Asn Tyr Tyr Trp Thr Leu Val Glu Pro Gly Asp Thr Ile
                245                 250                 255

Ile Phe Glu Ala Thr Gly Asn Leu Ile Ala Pro Trp Tyr Ala Phe Ala
            260                 265                 270

Leu Ser Arg Gly Phe Gly Ser Gly Ile Ile Thr Ser Asp Thr Pro Val
        275                 280                 285

His Asp Cys Asn Thr Thr Cys Gln Thr Pro Gln Gly Ala Ile Asn Ser
    290                 295                 300

Ser Leu Pro Phe Gln Asn Val His Pro Val Thr Ile Gly Glu Cys Pro
305                 310                 315                 320

Lys Tyr Val Arg Ser Ala Lys Leu Arg Met Ala Thr Gly Leu Arg Asn
                325                 330                 335

Ile Pro Ser Ile Gln Ser Arg Gly Leu Phe Gly Ala Ile Ala Gly Phe
                340                 345                 350

Ile Glu Gly Gly Trp Thr Gly Met Val Asp Gly Trp Tyr Gly Tyr His
            355                 360                 365

His Gln Asn Glu Gln Gly Ser Gly Tyr Ala Ala Asp Leu Lys Ser Thr
370                 375                 380

Gln Asn Ala Ile Asp Gly Ile Thr Asn Lys Val Asn Ser Val Ile Glu
385                 390                 395                 400

Lys Met Asn Thr Gln Phe Thr Ala Val Gly Lys Glu Phe Asn Lys Leu
                405                 410                 415

Glu Arg Arg Met Glu Asn Leu Asn Lys Lys Val Asp Asp Gly Phe Leu
            420                 425                 430

Asp Ile Trp Thr Tyr Asn Ala Glu Leu Leu Val Leu Leu Glu Asn Glu
        435                 440                 445

Arg Thr Leu Asp Phe His Asp Ser Asn Val Lys Asn Leu Tyr Glu Lys
    450                 455                 460

Val Lys Ser Gln Leu Lys Asn Asn Ala Lys Glu Ile Gly Asn Gly Cys
465                 470                 475                 480

Phe Glu Phe Tyr His Lys Cys Asn Asn Thr Cys Met Glu Ser Val Lys
                485                 490                 495

Asn Gly Thr Tyr Asp Tyr Pro Lys Tyr Ser Glu Glu Ser Lys Leu Asn
            500                 505                 510

Arg Glu Lys Ile Asp Gly Val Lys Leu Glu Ser Met Gly Val Tyr Gln
        515                 520                 525

Ile Leu Ala Ile Tyr Ser Thr Val Ala Ser Ser Leu Val Leu Leu Val
    530                 535                 540

Ser Leu Gly Ala Ile Ser Phe Trp Met Cys Ser Asn Gly Ser Leu Gln
545                 550                 555                 560

Cys Arg Ile Cys Ile
            565

<210> SEQ ID NO 4
<211> LENGTH: 565
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 4

Met Lys Ala Lys Leu Leu Val Leu Leu Cys Thr Phe Thr Ala Thr Tyr
1               5                   10                  15

Ala Asp Thr Ile Cys Ile Gly Tyr His Ala Asn Asn Ser Thr Asp Thr
                20                  25                  30

Val Asp Thr Val Leu Glu Lys Asn Val Thr Val Thr His Ser Val Asn
            35                  40                  45

Ile Leu Glu Asp Ser His Asn Gly Lys Leu Cys Leu Leu Lys Gly Ile
        50                  55                  60

Ala Pro Leu Gln Leu Gly Asn Cys Ser Val Ala Gly Trp Ile Leu Gly
65                  70                  75                  80

Asn Pro Glu Cys Glu Leu Leu Ile Ser Lys Glu Ser Trp Ser Tyr Ile
                85                  90                  95

Val Glu Lys Pro Asn Pro Glu Asn Gly Thr Cys Tyr Pro Gly Tyr Phe
            100                 105                 110

```
Ala Asp Tyr Glu Glu Leu Arg Glu Gln Leu Ser Ser Val Ser Ser Phe
        115                 120                 125

Glu Arg Phe Glu Ile Phe Pro Lys Glu Ser Ser Trp Pro Asn His Thr
130                 135                 140

Val Thr Gly Val Ser Ala Ser Cys Ser His Asn Gly Lys Ser Ser Phe
145                 150                 155                 160

Tyr Arg Asn Leu Leu Trp Leu Thr Gly Lys Asn Gly Leu Tyr Pro Asn
                165                 170                 175

Leu Ser Lys Ser Tyr Ala Asn Asn Lys Glu Lys Glu Val Leu Val Leu
            180                 185                 190

Trp Gly Val His His Pro Pro Asn Ile Gly Asp Gln Arg Ala Leu Tyr
        195                 200                 205

His Thr Glu Asn Ala Tyr Val Ser Val Val Ser Ser His Tyr Ser Arg
210                 215                 220

Arg Phe Thr Pro Glu Ile Ala Lys Arg Pro Lys Val Arg Asp Gln Glu
225                 230                 235                 240

Gly Arg Ile Asn Tyr Tyr Trp Thr Leu Leu Glu Pro Gly Asp Thr Ile
                245                 250                 255

Ile Phe Glu Ala Asn Gly Asn Leu Ile Ala Pro Trp Tyr Ala Phe Ala
            260                 265                 270

Leu Ser Arg Gly Phe Gly Ser Gly Ile Ile Thr Ser Asn Ala Pro Met
        275                 280                 285

Asp Lys Cys Asp Ala Lys Cys Gln Thr Pro Gln Gly Ala Ile Asn Ser
290                 295                 300

Ser Leu Pro Phe Gln Asn Val His Pro Val Thr Ile Gly Glu Cys Pro
305                 310                 315                 320

Lys Tyr Val Arg Ser Ala Lys Leu Arg Met Val Thr Gly Leu Arg Asn
                325                 330                 335

Ile Pro Phe Ile Gln Ser Arg Gly Leu Phe Gly Ala Ile Ala Gly Phe
            340                 345                 350

Ile Glu Gly Gly Trp Thr Gly Met Val Asp Gly Trp Tyr Gly Tyr His
        355                 360                 365

His Gln Asn Glu Gln Gly Ser Gly Tyr Ala Ala Asp Gln Lys Ser Thr
370                 375                 380

Gln Asn Ala Ile Asn Gly Ile Thr Asn Lys Val Asn Ser Val Ile Glu
385                 390                 395                 400

Lys Met Asn Thr Gln Phe Thr Ala Val Gly Lys Glu Phe Asn Lys Leu
                405                 410                 415

Glu Arg Arg Met Glu Asn Leu Asn Lys Lys Val Asp Asp Gly Phe Leu
            420                 425                 430

Asp Ile Trp Thr Tyr Asn Ala Glu Leu Leu Val Leu Leu Glu Asn Glu
        435                 440                 445

Arg Thr Leu Asp Phe His Asp Ser Asn Val Lys Asn Leu Tyr Glu Lys
450                 455                 460

Val Lys Ser Gln Leu Lys Asn Asn Ala Lys Glu Ile Gly Asn Gly Cys
465                 470                 475                 480

Phe Glu Phe Tyr His Lys Cys Asn Asp Glu Cys Met Glu Ser Val Lys
                485                 490                 495

Asn Gly Thr Tyr Asp Tyr Pro Lys Tyr Ser Glu Glu Ser Lys Leu Asn
            500                 505                 510

Arg Glu Lys Ile Asp Gly Val Lys Leu Glu Ser Met Gly Val Tyr Gln
        515                 520                 525

Ile Leu Ala Ile Tyr Ser Thr Val Ala Ser Ser Leu Val Leu Leu Val
```

```
            530                 535                 540
Ser Leu Gly Ala Ile Ser Phe Trp Met Cys Ser Asn Gly Ser Leu Gln
545                 550                 555                 560

Cys Arg Ile Cys Ile
            565

<210> SEQ ID NO 5
<211> LENGTH: 565
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 5

Met Lys Ala Lys Leu Leu Val Leu Cys Thr Phe Thr Ala Thr Tyr
1               5                   10                  15

Ala Asp Thr Ile Cys Ile Gly Tyr His Ala Asn Asn Ser Thr Asp Thr
                20                  25                  30

Val Asp Thr Val Leu Glu Lys Asn Val Thr Val Thr His Ser Val Asn
            35                  40                  45

Ile Leu Glu Asp Ser His Asn Gly Lys Leu Cys Leu Leu Lys Gly Ile
        50                  55                  60

Ala Pro Leu Gln Leu Gly Asn Cys Ser Val Ala Gly Trp Ile Leu Gly
65                  70                  75                  80

Asn Pro Glu Cys Glu Leu Leu Ile Ser Lys Glu Ser Trp Ser Tyr Ile
                85                  90                  95

Val Glu Lys Pro Asn Pro Glu Asn Gly Thr Cys Tyr Pro Gly Tyr Phe
            100                 105                 110

Ala Asp Tyr Glu Glu Leu Arg Glu Gln Leu Ser Ser Val Ser Ser Phe
        115                 120                 125

Glu Arg Phe Glu Ile Phe Pro Lys Glu Ser Ser Trp Pro Asn His Thr
130                 135                 140

Val Thr Gly Val Ser Ala Ser Cys Pro His Asn Gly Glu Ser Ser Phe
145                 150                 155                 160

Tyr Arg Asn Leu Leu Trp Leu Thr Gly Lys Asn Gly Leu Tyr Pro Asn
                165                 170                 175

Leu Ser Lys Ser Tyr Ala Asn Asn Lys Glu Lys Glu Val Leu Val Leu
            180                 185                 190

Trp Gly Val His His Pro Pro Asn Ile Gly Asp Gln Lys Thr Leu Tyr
        195                 200                 205

His Thr Glu Asn Ala Tyr Val Ser Val Val Ser Ser His Tyr Ser Arg
210                 215                 220

Arg Phe Thr Pro Glu Ile Ala Lys Arg Pro Lys Val Arg Asp Gln Glu
225                 230                 235                 240

Gly Arg Ile Asn Tyr Tyr Trp Thr Leu Leu Glu Pro Gly Asp Thr Ile
                245                 250                 255

Ile Phe Glu Ala Asn Gly Asn Leu Ile Ala Pro Trp Tyr Ala Phe Ala
            260                 265                 270

Leu Ser Arg Gly Phe Gly Ser Gly Ile Ile Thr Ser Asn Ala Pro Met
        275                 280                 285

Asp Lys Cys Asp Ala Lys Cys Gln Thr Pro Gln Gly Ala Ile Asn Ser
    290                 295                 300

Ser Leu Pro Phe Gln Asn Val His Pro Val Thr Ile Gly Glu Cys Pro
305                 310                 315                 320
```

-continued

```
Lys Tyr Val Arg Ser Ala Lys Leu Arg Met Ala Thr Gly Leu Arg Asn
            325                 330                 335

Ile Gln Ser Ile Gln Ser Arg Gly Leu Phe Gly Ala Ile Ala Gly Phe
            340                 345                 350

Ile Glu Gly Gly Trp Thr Gly Met Val Asp Gly Trp Tyr Gly Tyr His
            355                 360                 365

His Gln Asn Glu Gln Gly Ser Gly Tyr Ala Ala Asp Leu Lys Ser Thr
            370                 375                 380

Gln Asn Ala Ile Asn Gly Ile Thr Asn Lys Val Asn Ser Val Ile Glu
385                 390                 395                 400

Lys Met Asn Thr Gln Phe Thr Ala Val Gly Lys Glu Phe Asn Lys Leu
            405                 410                 415

Glu Arg Arg Met Glu Asn Leu Asn Lys Lys Val Asp Asp Gly Phe Leu
            420                 425                 430

Asp Ile Trp Thr Tyr Asn Ala Glu Leu Leu Val Leu Leu Glu Asn Glu
            435                 440                 445

Arg Thr Leu Asp Phe His Asp Ser Asn Val Lys Asn Leu Tyr Glu Lys
        450                 455                 460

Val Lys Ser Gln Leu Lys Asn Asn Ala Lys Glu Ile Gly Asn Gly Cys
465                 470                 475                 480

Phe Glu Phe Tyr His Lys Cys Asn Asn Thr Cys Met Glu Ser Val Lys
            485                 490                 495

Asn Gly Thr Tyr Asp Tyr Pro Lys Tyr Ser Glu Glu Ser Lys Leu Asn
            500                 505                 510

Arg Glu Lys Ile Asp Gly Val Lys Leu Glu Ser Met Gly Val Tyr Gln
            515                 520                 525

Ile Leu Ala Ile Tyr Ser Thr Val Ala Ser Ser Leu Val Leu Leu Val
            530                 535                 540

Ser Leu Gly Ala Ile Ser Phe Trp Met Cys Ser Asn Gly Ser Leu Gln
545                 550                 555                 560

Cys Arg Ile Cys Ile
            565
```

<210> SEQ ID NO 6
<211> LENGTH: 566
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 6

```
Met Lys Ala Ile Leu Val Val Leu Leu Tyr Thr Phe Ala Thr Ala Asn
1               5                   10                  15

Ala Asp Thr Leu Cys Ile Gly Tyr His Ala Asn Asn Ser Thr Asp Thr
            20                  25                  30

Val Asp Thr Val Leu Glu Lys Asn Val Thr Val Thr His Ser Val Asn
            35                  40                  45

Leu Leu Glu Asp Lys His Asn Gly Lys Leu Cys Lys Leu Arg Gly Val
        50                  55                  60

Ala Pro Leu His Leu Gly Lys Cys Asn Ile Ala Gly Trp Ile Leu Gly
65                  70                  75                  80

Asn Pro Glu Cys Glu Ser Leu Ser Thr Ala Ser Ser Trp Ser Tyr Ile
            85                  90                  95
```

```
Val Glu Thr Ser Asn Ser Glu Asn Gly Thr Cys Tyr Pro Gly Asp Phe
            100                 105                 110

Ile Asp Tyr Glu Glu Leu Arg Glu Gln Leu Ser Ser Val Ser Ser Phe
        115                 120                 125

Glu Arg Phe Glu Ile Phe Pro Lys Glu Ser Ser Trp Pro Asn His Thr
    130                 135                 140

Val Thr Lys Gly Val Thr Ala Ala Cys Ser His Ala Gly Lys Ser Ser
145                 150                 155                 160

Phe Tyr Lys Asn Leu Ile Trp Leu Thr Gly Lys Asn Gly Ser Tyr Pro
                165                 170                 175

Asn Leu Ser Lys Ser Tyr Val Asn Asn Lys Glu Lys Glu Val Leu Val
            180                 185                 190

Leu Trp Gly Ile His His Pro Ser Asn Ile Gly Asp Gln Gln Thr Leu
        195                 200                 205

Tyr Gln Thr Glu Asp Thr Tyr Val Phe Val Gly Ser Ser Arg Tyr Ser
    210                 215                 220

Lys Lys Phe Lys Pro Glu Ile Ala Lys Arg Pro Lys Val Arg Asp Gln
225                 230                 235                 240

Glu Gly Arg Met Asn Tyr Tyr Trp Thr Leu Val Glu Pro Gly Asp Lys
                245                 250                 255

Ile Thr Phe Glu Ala Asn Gly Asn Leu Val Val Pro Arg Tyr Ala Phe
            260                 265                 270

Ala Met Glu Arg Asn Ala Gly Ser Gly Ile Ile Ile Ser Asn Ala Pro
        275                 280                 285

Val His Asp Cys Asn Thr Lys Cys Gln Thr Pro Lys Gly Ala Ile Asn
    290                 295                 300

Thr Ser Leu Pro Phe Gln Asn Ile His Pro Ile Thr Ile Gly Lys Cys
305                 310                 315                 320

Pro Lys Tyr Val Lys Ser Thr Lys Leu Arg Leu Ala Thr Gly Leu Arg
                325                 330                 335

Asn Ile Pro Ser Ile Gln Ser Arg Gly Leu Phe Gly Ala Ile Ala Gly
            340                 345                 350

Phe Ile Glu Gly Gly Trp Thr Gly Met Val Asp Gly Trp Tyr Gly Tyr
        355                 360                 365

His His Gln Asn Glu Gln Gly Ser Gly Tyr Ala Ala Asp Gln Lys Ser
    370                 375                 380

Thr Gln Asn Ala Ile Asp Glu Ile Thr Asn Lys Val Asn Ser Val Ile
385                 390                 395                 400

Glu Lys Met Asn Thr Gln Phe Thr Ala Val Gly Lys Glu Phe Asn His
                405                 410                 415

Leu Glu Lys Arg Ile Glu Asn Leu Asn Lys Lys Val Asp Asp Gly Phe
            420                 425                 430

Leu Asp Ile Trp Thr Tyr Asn Ala Glu Leu Leu Val Leu Leu Glu Asn
        435                 440                 445

Glu Arg Thr Leu Asp Tyr His Asp Ser Asn Val Lys Asn Leu Tyr Glu
    450                 455                 460

Lys Val Arg Ser Gln Leu Lys Asn Asn Ala Lys Glu Ile Gly Asn Gly
465                 470                 475                 480

Cys Phe Glu Phe Tyr His Lys Cys Asp Asn Thr Cys Met Glu Ser Val
                485                 490                 495

Lys Asn Gly Thr Tyr Asp Tyr Pro Lys Tyr Ser Glu Glu Ala Lys Leu
            500                 505                 510

Asn Arg Glu Glu Ile Asp Gly Val Lys Leu Glu Ser Thr Arg Ile Tyr
```

-continued

```
                515                 520                 525
Gln Ile Leu Ala Ile Tyr Ser Thr Val Ala Ser Ser Leu Val Leu Val
            530                 535                 540

Val Ser Leu Gly Ala Ile Ser Phe Trp Met Cys Ser Asn Gly Ser Leu
545                 550                 555                 560

Gln Cys Arg Ile Cys Ile
                565

<210> SEQ ID NO 7
<211> LENGTH: 566
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 7

Met Lys Ala Ile Leu Val Val Leu Leu Tyr Thr Phe Ala Thr Ala Asn
1               5                   10                  15

Ala Asp Thr Leu Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asp Lys His Asn Gly Lys Leu Cys Leu Leu Arg Gly Val
50                  55                  60

Ala Pro Leu His Leu Gly Asn Cys Asn Ile Ala Gly Trp Ile Leu Gly
65                  70                  75                  80

Asn Pro Glu Cys Glu Leu Leu Ser Thr Lys Ser Ser Trp Ser Tyr Ile
                85                  90                  95

Val Glu Thr Pro Asn Ser Glu Asn Gly Thr Cys Tyr Pro Gly Asp Phe
            100                 105                 110

Ile Asp Tyr Glu Glu Leu Arg Glu Gln Leu Ser Ser Val Ser Ser Phe
        115                 120                 125

Glu Arg Phe Glu Ile Phe Pro Lys Glu Ser Ser Trp Pro Asn His Asp
130                 135                 140

Val Thr Lys Gly Val Ser Ala Ala Cys Ser His Asn Gly Ala Ser Ser
145                 150                 155                 160

Phe Tyr Lys Asn Leu Ile Trp Leu Thr Lys Lys Asn Asn Leu Tyr Pro
                165                 170                 175

Asn Leu Ser Lys Ser Tyr Ala Asn Asn Lys Gly Lys Glu Val Leu Val
            180                 185                 190

Leu Trp Gly Ile His His Pro Ser Thr Ile Ala Asp Gln Gln Thr Leu
        195                 200                 205

Tyr His Thr Glu Asp Thr Tyr Val Phe Val Gly Ser Ser His Tyr Ser
210                 215                 220

Lys Lys Phe Lys Pro Glu Ile Ala Ile Arg Pro Lys Val Arg Asp Gln
225                 230                 235                 240

Glu Gly Arg Ile Asn Tyr Tyr Trp Thr Leu Leu Glu Pro Gly Asp Lys
                245                 250                 255

Ile Thr Phe Glu Ala Asn Gly Asn Leu Val Val Pro Arg Tyr Ala Phe
            260                 265                 270

Ala Met Glu Arg Asn Ala Gly Ser Gly Ile Ile Ile Ser Asn Ala Pro
        275                 280                 285

Met Asp Glu Cys Asn Thr Thr Cys Gln Thr Pro Lys Gly Ala Ile Asn
290                 295                 300
```

```
Thr Ser Leu Pro Phe Gln Asn Ile His Pro Ile Thr Ile Gly Lys Cys
305                 310                 315                 320

Pro Lys Tyr Val Lys Ser Thr Lys Leu Arg Leu Val Thr Gly Leu Arg
                325                 330                 335

Asn Ile Pro Ser Ile Gln Ser Arg Gly Leu Phe Gly Ala Ile Ala Gly
            340                 345                 350

Phe Ile Glu Gly Gly Trp Thr Gly Met Val Asp Gly Trp Tyr Gly Tyr
        355                 360                 365

His His Gln Asn Glu Gln Gly Ser Gly Tyr Ala Ala Asp Leu Lys Ser
    370                 375                 380

Thr Gln Asn Ala Ile Asn Glu Ile Thr Asn Lys Val Asn Ser Val Ile
385                 390                 395                 400

Glu Lys Met Asn Thr Gln Phe Thr Ala Val Gly Lys Glu Phe Asn His
                405                 410                 415

Leu Glu Lys Arg Ile Glu Asn Leu Asn Lys Lys Val Asp Asp Gly Phe
            420                 425                 430

Leu Asp Ile Trp Thr Tyr Asn Ala Glu Leu Leu Val Leu Leu Glu Asn
        435                 440                 445

Glu Arg Thr Leu Asp Tyr His Asp Ser Asn Val Lys Asn Leu Tyr Glu
    450                 455                 460

Lys Val Arg Ser Gln Leu Lys Asn Asn Ala Lys Glu Ile Gly Asn Gly
465                 470                 475                 480

Cys Phe Glu Phe Tyr His Lys Cys Asp Asn Glu Cys Met Glu Ser Val
                485                 490                 495

Lys Asn Gly Thr Tyr Asp Tyr Pro Lys Tyr Ser Glu Glu Ala Lys Leu
            500                 505                 510

Asn Arg Glu Glu Ile Asp Gly Val Lys Leu Glu Ser Thr Arg Ile Tyr
        515                 520                 525

Gln Ile Leu Ala Ile Tyr Ser Thr Val Ala Ser Ser Leu Val Leu Val
    530                 535                 540

Val Ser Leu Gly Ala Ile Ser Phe Trp Met Cys Ser Asn Gly Ser Leu
545                 550                 555                 560

Gln Cys Arg Ile Cys Ile
                565

<210> SEQ ID NO 8
<211> LENGTH: 566
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 8

Met Lys Ala Ile Leu Val Val Leu Leu Tyr Thr Phe Ala Thr Ala Asn
1               5                   10                  15

Ala Asp Thr Leu Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asp Lys His Asn Gly Lys Leu Cys Lys Leu Arg Gly Val
    50                  55                  60

Ala Pro Leu His Leu Gly Lys Cys Asn Ile Ala Gly Trp Ile Leu Gly
65                  70                  75                  80
```

```
Asn Pro Glu Cys Glu Ser Leu Ser Thr Ala Ser Ser Trp Ser Tyr Ile
                85                  90                  95

Val Glu Thr Ser Ser Ser Asp Asn Gly Thr Cys Tyr Pro Gly Asp Phe
            100                 105                 110

Ile Asp Tyr Glu Glu Leu Arg Glu Gln Leu Ser Ser Val Ser Ser Phe
            115                 120                 125

Glu Arg Phe Glu Ile Phe Pro Lys Thr Ser Ser Trp Pro Asn His Asp
            130                 135                 140

Ser Asn Lys Gly Val Thr Ala Ala Cys Pro His Ala Gly Ala Lys Ser
145                 150                 155                 160

Phe Tyr Lys Asn Leu Ile Trp Leu Val Lys Lys Gly Asn Ser Tyr Pro
                165                 170                 175

Lys Leu Ser Lys Ser Tyr Ile Asn Asp Lys Gly Lys Glu Val Leu Val
                180                 185                 190

Leu Trp Gly Ile His His Pro Ser Thr Ser Ala Asp Gln Gln Ser Leu
                195                 200                 205

Tyr Gln Asn Ala Asp Thr Tyr Val Phe Val Gly Thr Ser Arg Tyr Ser
    210                 215                 220

Lys Lys Phe Lys Pro Glu Ile Ala Ile Arg Pro Lys Val Arg Asp Gln
225                 230                 235                 240

Glu Gly Arg Met Asn Tyr Tyr Trp Thr Leu Val Glu Pro Gly Asp Lys
                245                 250                 255

Ile Thr Phe Glu Ala Thr Gly Asn Leu Val Val Pro Arg Tyr Ala Phe
                260                 265                 270

Ala Met Glu Arg Asn Ala Gly Ser Gly Ile Ile Ile Ser Asp Thr Pro
                275                 280                 285

Val His Asp Cys Asn Thr Thr Cys Gln Thr Pro Lys Gly Ala Ile Asn
    290                 295                 300

Thr Ser Leu Pro Phe Gln Asn Ile His Pro Ile Thr Ile Gly Lys Cys
305                 310                 315                 320

Pro Lys Tyr Val Lys Ser Thr Lys Leu Arg Leu Ala Thr Gly Leu Arg
                325                 330                 335

Asn Ile Pro Ser Ile Gln Ser Arg Gly Leu Phe Gly Ala Ile Ala Gly
                340                 345                 350

Phe Ile Glu Gly Gly Trp Thr Gly Met Val Asp Gly Trp Tyr Gly Tyr
                355                 360                 365

His His Gln Asn Glu Gln Gly Ser Gly Tyr Ala Ala Asp Leu Lys Ser
    370                 375                 380

Thr Gln Asn Ala Ile Asp Glu Ile Thr Asn Lys Val Asn Ser Val Ile
385                 390                 395                 400

Glu Lys Met Asn Thr Gln Phe Thr Ala Val Gly Lys Glu Phe Asn His
                405                 410                 415

Leu Glu Lys Arg Ile Glu Asn Leu Asn Lys Lys Val Asp Asp Gly Phe
                420                 425                 430

Leu Asp Ile Trp Thr Tyr Asn Ala Glu Leu Leu Val Leu Leu Glu Asn
                435                 440                 445

Glu Arg Thr Leu Asp Tyr His Asp Ser Asn Val Lys Asn Leu Tyr Glu
    450                 455                 460

Lys Val Arg Ser Gln Leu Lys Asn Asn Ala Lys Glu Ile Gly Asn Gly
465                 470                 475                 480

Cys Phe Glu Phe Tyr His Lys Cys Asp Asn Thr Cys Met Glu Ser Val
                485                 490                 495

Lys Asn Gly Thr Tyr Asp Tyr Pro Lys Tyr Ser Glu Glu Ala Lys Leu
```

500                 505                 510
Asn Arg Glu Glu Ile Asp Gly Val Lys Leu Glu Ser Thr Arg Ile Tyr
            515                 520                 525

Gln Ile Leu Ala Ile Tyr Ser Thr Val Ala Ser Ser Leu Val Leu Val
        530                 535                 540

Val Ser Leu Gly Ala Ile Ser Phe Trp Met Cys Ser Asn Gly Ser Leu
545                 550                 555                 560

Gln Cys Arg Ile Cys Ile
            565

<210> SEQ ID NO 9
<211> LENGTH: 566
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 9

Met Lys Ala Ile Leu Val Val Leu Leu Tyr Thr Phe Ala Thr Ala Asn
1               5                   10                  15

Ala Asp Thr Leu Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Ile Leu Glu Asp Lys His Asn Gly Lys Leu Cys Leu Leu Arg Gly Val
50                  55                  60

Ala Pro Leu His Leu Gly Asn Cys Asn Ile Ala Gly Trp Ile Leu Gly
65                  70                  75                  80

Asn Pro Glu Cys Glu Leu Leu Ile Ser Lys Ser Trp Ser Tyr Ile
                85                  90                  95

Val Glu Lys Pro Asn Ser Glu Asn Gly Thr Cys Tyr Pro Gly Asp Phe
            100                 105                 110

Ile Asp Tyr Glu Glu Leu Arg Glu Gln Leu Ser Ser Val Ser Ser Phe
        115                 120                 125

Glu Arg Phe Glu Ile Phe Pro Lys Glu Ser Ser Trp Pro Asn His Thr
130                 135                 140

Val Thr Lys Gly Val Ser Ala Ala Cys Ser His Asn Gly Lys Ser Ser
145                 150                 155                 160

Phe Tyr Lys Asn Leu Ile Trp Leu Thr Gly Lys Asn Gly Leu Tyr Pro
                165                 170                 175

Asn Leu Ser Lys Ser Tyr Ala Asn Asn Lys Glu Lys Glu Val Leu Val
            180                 185                 190

Leu Trp Gly Ile His His Pro Pro Asn Ile Gly Asp Gln Arg Ala Leu
        195                 200                 205

Tyr His Thr Glu Asp Thr Tyr Val Phe Val Gly Ser Ser His Tyr Ser
210                 215                 220

Lys Lys Phe Lys Pro Glu Ile Ala Lys Arg Pro Lys Val Arg Asp Gln
225                 230                 235                 240

Glu Gly Arg Ile Asn Tyr Tyr Trp Thr Leu Leu Glu Pro Gly Asp Lys
                245                 250                 255

Ile Thr Phe Glu Ala Asn Gly Asn Leu Val Val Pro Arg Tyr Ala Phe
            260                 265                 270

Ala Met Glu Arg Asn Ala Gly Ser Gly Ile Ile Ile Ser Asn Ala Pro
        275                 280                 285

-continued

```
Met Asp Lys Cys Asp Ala Lys Cys Gln Thr Pro Lys Gly Ala Ile Asn
290                 295                 300

Thr Ser Leu Pro Phe Gln Asn Ile His Pro Ile Thr Ile Gly Lys Cys
305                 310                 315                 320

Pro Lys Tyr Val Lys Ser Thr Lys Leu Arg Leu Val Thr Gly Leu Arg
                325                 330                 335

Asn Ile Pro Phe Ile Gln Ser Arg Gly Leu Phe Gly Ala Ile Ala Gly
                340                 345                 350

Phe Ile Glu Gly Gly Trp Thr Gly Met Val Asp Gly Trp Tyr Gly Tyr
            355                 360                 365

His His Gln Asn Glu Gln Gly Ser Gly Tyr Ala Ala Asp Gln Lys Ser
        370                 375                 380

Thr Gln Asn Ala Ile Asn Glu Ile Thr Asn Lys Val Asn Ser Val Ile
385                 390                 395                 400

Glu Lys Met Asn Thr Gln Phe Thr Ala Val Gly Lys Glu Phe Asn His
                405                 410                 415

Leu Glu Lys Arg Ile Glu Asn Leu Asn Lys Lys Val Asp Asp Gly Phe
                420                 425                 430

Leu Asp Ile Trp Thr Tyr Asn Ala Glu Leu Leu Val Leu Leu Glu Asn
            435                 440                 445

Glu Arg Thr Leu Asp Tyr His Asp Ser Asn Val Lys Asn Leu Tyr Glu
        450                 455                 460

Lys Val Arg Ser Gln Leu Lys Asn Asn Ala Lys Glu Ile Gly Asn Gly
465                 470                 475                 480

Cys Phe Glu Phe Tyr His Lys Cys Asp Asp Glu Cys Met Glu Ser Val
                485                 490                 495

Lys Asn Gly Thr Tyr Asp Tyr Pro Lys Tyr Ser Glu Glu Ala Lys Leu
            500                 505                 510

Asn Arg Glu Glu Ile Asp Gly Val Lys Leu Glu Ser Thr Arg Ile Tyr
        515                 520                 525

Gln Ile Leu Ala Ile Tyr Ser Thr Val Ala Ser Ser Leu Val Leu Val
530                 535                 540

Val Ser Leu Gly Ala Ile Ser Phe Trp Met Cys Ser Asn Gly Ser Leu
545                 550                 555                 560

Gln Cys Arg Ile Cys Ile
                565

<210> SEQ ID NO 10
<211> LENGTH: 566
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 10

Met Lys Ala Ile Leu Val Val Leu Leu Tyr Thr Phe Ala Thr Ala Asn
1               5                   10                  15

Ala Asp Thr Leu Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Ile Leu Glu Asp Lys His Asn Gly Lys Leu Cys Leu Leu Arg Gly Val
50                  55                  60
```

```
Ala Pro Leu His Leu Gly Asn Cys Asn Ile Ala Gly Trp Ile Leu Gly
 65                  70                  75                  80

Asn Pro Glu Cys Glu Leu Leu Ile Ser Lys Glu Ser Trp Ser Tyr Ile
                 85                  90                  95

Val Glu Lys Pro Asn Ser Glu Asn Gly Thr Cys Tyr Pro Gly Asp Phe
            100                 105                 110

Ile Asp Tyr Glu Glu Leu Arg Glu Gln Leu Ser Ser Val Ser Ser Phe
        115                 120                 125

Glu Arg Phe Glu Ile Phe Pro Lys Glu Ser Ser Trp Pro Asn His Thr
    130                 135                 140

Val Thr Lys Gly Val Ser Ala Ala Cys Pro His Asn Gly Glu Ser Ser
145                 150                 155                 160

Phe Tyr Lys Asn Leu Ile Trp Leu Thr Gly Lys Asn Gly Leu Tyr Pro
                165                 170                 175

Asn Leu Ser Lys Ser Tyr Ala Asn Asn Lys Glu Lys Glu Val Leu Val
            180                 185                 190

Leu Trp Gly Ile His His Pro Pro Asn Ile Gly Asp Gln Lys Thr Leu
        195                 200                 205

Tyr His Thr Glu Asp Thr Tyr Val Phe Val Gly Ser Ser His Tyr Ser
    210                 215                 220

Lys Lys Phe Lys Pro Glu Ile Ala Lys Arg Pro Lys Val Arg Asp Gln
225                 230                 235                 240

Glu Gly Arg Ile Asn Tyr Tyr Trp Thr Leu Leu Glu Pro Gly Asp Lys
                245                 250                 255

Ile Thr Phe Glu Ala Asn Gly Asn Leu Val Val Pro Arg Tyr Ala Phe
            260                 265                 270

Ala Met Glu Arg Asn Ala Gly Ser Gly Ile Ile Ile Ser Asn Ala Pro
        275                 280                 285

Met Asp Lys Cys Asp Ala Lys Cys Gln Thr Pro Lys Gly Ala Ile Asn
    290                 295                 300

Thr Ser Leu Pro Phe Gln Asn Ile His Pro Ile Thr Ile Gly Lys Cys
305                 310                 315                 320

Pro Lys Tyr Val Lys Ser Thr Lys Leu Arg Leu Ala Thr Gly Leu Arg
                325                 330                 335

Asn Ile Gln Ser Ile Gln Ser Arg Gly Leu Phe Gly Ala Ile Ala Gly
            340                 345                 350

Phe Ile Glu Gly Gly Trp Thr Gly Met Val Asp Gly Trp Tyr Gly Tyr
        355                 360                 365

His His Gln Asn Glu Gln Gly Ser Gly Tyr Ala Ala Asp Leu Lys Ser
    370                 375                 380

Thr Gln Asn Ala Ile Asn Glu Ile Thr Asn Lys Val Asn Ser Val Ile
385                 390                 395                 400

Glu Lys Met Asn Thr Gln Phe Thr Ala Val Gly Lys Glu Phe Asn His
                405                 410                 415

Leu Glu Lys Arg Ile Glu Asn Leu Asn Lys Lys Val Asp Asp Gly Phe
            420                 425                 430

Leu Asp Ile Trp Thr Tyr Asn Ala Glu Leu Leu Val Leu Leu Glu Asn
        435                 440                 445

Glu Arg Thr Leu Asp Tyr His Asp Ser Asn Val Lys Asn Leu Tyr Glu
    450                 455                 460

Lys Val Arg Ser Gln Leu Lys Asn Asn Ala Lys Glu Ile Gly Asn Gly
465                 470                 475                 480

Cys Phe Glu Phe Tyr His Lys Cys Asp Asn Thr Cys Met Glu Ser Val
```

```
                    485                 490                 495
Lys Asn Gly Thr Tyr Asp Tyr Pro Lys Tyr Ser Glu Glu Ala Lys Leu
                500                 505                 510

Asn Arg Glu Glu Ile Asp Gly Val Lys Leu Glu Ser Thr Arg Ile Tyr
            515                 520                 525

Gln Ile Leu Ala Ile Tyr Ser Thr Val Ala Ser Ser Leu Val Leu Val
    530                 535                 540

Val Ser Leu Gly Ala Ile Ser Phe Trp Met Cys Ser Asn Gly Ser Leu
545                 550                 555                 560

Gln Cys Arg Ile Cys Ile
                565
```

<210> SEQ ID NO 11
<211> LENGTH: 26
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic peptide"

<400> SEQUENCE: 11

```
Gly Val Thr Ala Ser Ser Trp Leu Thr His His Pro Ser Asn Gly Asp
1               5                   10                  15

Gln Gln Thr Leu Lys Asp Gln Glu Gly Arg
            20                  25
```

<210> SEQ ID NO 12
<211> LENGTH: 26
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic peptide"

<400> SEQUENCE: 12

```
Gly Val Ser Ala Ser Ser Trp Leu Thr His His Pro Ser Thr Ala Asp
1               5                   10                  15

Gln Gln Thr Leu Lys Asp Gln Glu Gly Arg
            20                  25
```

<210> SEQ ID NO 13
<211> LENGTH: 26
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic peptide"

<400> SEQUENCE: 13

```
Gly Val Thr Ala Ser Lys Trp Leu Val His His Pro Ser Thr Ala Asp
1               5                   10                  15

Gln Gln Ser Leu Lys Asp Gln Glu Gly Arg
            20                  25
```

<210> SEQ ID NO 14
<211> LENGTH: 26
<212> TYPE: PRT
<213> ORGANISM: Artificial Sequence
<220> FEATURE:
<221> NAME/KEY: source
<223> OTHER INFORMATION: /note="Description of Artificial Sequence:

Synthetic peptide"

<400> SEQUENCE: 14

Gly Val Ser Ala Ser Ser Trp Leu Thr His His Pro Pro Asn Gly Asp
1               5                   10                  15

Gln Arg Ala Leu Lys Asp Gln Glu Gly Arg
            20                  25

<210> SEQ ID NO 15
<211> LENGTH: 26
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 15

Gly Val Ser Ala Ser Ser Trp Leu Thr His His Pro Pro Asn Gly Asp
1               5                   10                  15

Gln Lys Thr Leu Lys Asp Gln Glu Gly Arg
            20                  25

<210> SEQ ID NO 16
<211> LENGTH: 26
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 16

Gly Val Ser Ala Ala Ser Trp Leu Thr His His Pro Ser Thr Ala Asp
1               5                   10                  15

Gln Gln Thr Leu Lys Asp Gln Glu Gly Arg
            20                  25

<210> SEQ ID NO 17
<211> LENGTH: 26
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 17

Gly Val Thr Ala Ala Lys Trp Leu Val His His Pro Ser Thr Ala Asp
1               5                   10                  15

Gln Gln Ser Leu Lys Asp Gln Glu Gly Arg
            20                  25

<210> SEQ ID NO 18
<211> LENGTH: 26
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 18

Gly Val Ser Ala Ala Ser Trp Leu Thr His His Pro Pro Asn Gly Asp
1               5                   10                  15

Gln Arg Ala Leu Lys Asp Gln Glu Gly Arg
            20                  25

<210> SEQ ID NO 19
<211> LENGTH: 26
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 19

Gly Val Ser Ala Ala Ser Trp Leu Thr His His Pro Pro Asn Gly Asp
1               5                   10                  15

Gln Lys Thr Leu Lys Asp Gln Glu Gly Arg
            20                  25

<210> SEQ ID NO 20
<211> LENGTH: 54
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 20

Cys Tyr Pro Thr Val Thr Gly Val Thr Ala Ser Cys Ser Lys Ser Ser
1               5                   10                  15

Phe Leu Trp Leu Thr Gly Val His His Pro Ser Asn Ile Gly Asp Gln
            20                  25                  30

Gln Thr Leu Tyr Gln Glu Ile Ala Lys Arg Pro Lys Val Arg Asp Gln
        35                  40                  45

Glu Gly Arg Met Asn Ile
    50

<210> SEQ ID NO 21
<211> LENGTH: 54
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 21

Cys Tyr Pro Asp Val Thr Gly Val Ser Ala Ser Cys Ser Ala Ser Ser
1               5                   10                  15

Phe Leu Trp Leu Thr Lys Val His His Pro Ser Thr Ile Ala Asp Gln
            20                  25                  30

Gln Thr Leu Tyr His Glu Ile Ala Ile Arg Pro Lys Val Arg Asp Gln
        35                  40                  45

Glu Gly Arg Ile Asn Ile
    50

<210> SEQ ID NO 22
<211> LENGTH: 54
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

```
<400> SEQUENCE: 22

Cys Tyr Pro Asp Ser Asn Gly Val Thr Ala Ser Cys Pro Ala Lys Ser
1               5                   10                  15

Phe Leu Trp Leu Val Lys Val His His Pro Ser Thr Ser Ala Asp Gln
            20                  25                  30

Gln Ser Leu Tyr Gln Glu Ile Ala Ile Arg Pro Lys Val Arg Asp Gln
        35                  40                  45

Glu Gly Arg Met Asn Ile
    50

<210> SEQ ID NO 23
<211> LENGTH: 54
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 23

Cys Tyr Pro Thr Val Thr Gly Val Ser Ala Ser Cys Ser Lys Ser Ser
1               5                   10                  15

Phe Leu Trp Leu Thr Gly Val His His Pro Pro Asn Ile Gly Asp Gln
            20                  25                  30

Arg Ala Leu Tyr His Glu Ile Ala Lys Arg Pro Lys Val Arg Asp Gln
        35                  40                  45

Glu Gly Arg Ile Asn Ile
    50

<210> SEQ ID NO 24
<211> LENGTH: 54
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 24

Cys Tyr Pro Thr Val Thr Gly Val Ser Ala Ser Cys Pro Glu Ser Ser
1               5                   10                  15

Phe Leu Trp Leu Thr Gly Val His His Pro Pro Asn Ile Gly Asp Gln
            20                  25                  30

Lys Thr Leu Tyr His Glu Ile Ala Lys Arg Pro Lys Val Arg Asp Gln
        35                  40                  45

Glu Gly Arg Ile Asn Ile
    50

<210> SEQ ID NO 25
<211> LENGTH: 55
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 25

Cys Tyr Pro Thr Val Thr Lys Gly Val Thr Ala Ala Cys Ser Lys Ser
1               5                   10                  15

Ser Phe Ile Trp Leu Thr Gly Ile His His Pro Ser Asn Ile Gly Asp
            20                  25                  30
```

-continued

Gln Gln Thr Leu Tyr Gln Glu Ile Ala Lys Arg Pro Lys Val Arg Asp
        35                  40                  45

Gln Glu Gly Arg Met Asn Val
    50                  55

<210> SEQ ID NO 26
<211> LENGTH: 55
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 26

Cys Tyr Pro Asp Val Thr Lys Gly Val Ser Ala Ala Cys Ser Ala Ser
1               5                   10                  15

Ser Phe Ile Trp Leu Thr Lys Ile His His Pro Ser Thr Ile Ala Asp
                20                  25                  30

Gln Gln Thr Leu Tyr His Glu Ile Ala Ile Arg Pro Lys Val Arg Asp
        35                  40                  45

Gln Glu Gly Arg Ile Asn Val
    50                  55

<210> SEQ ID NO 27
<211> LENGTH: 55
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 27

Cys Tyr Pro Asp Ser Asn Lys Gly Val Thr Ala Ala Cys Pro Ala Lys
1               5                   10                  15

Ser Phe Ile Trp Leu Val Lys Ile His His Pro Ser Thr Ser Ala Asp
                20                  25                  30

Gln Gln Ser Leu Tyr Gln Glu Ile Ala Ile Arg Pro Lys Val Arg Asp
        35                  40                  45

Gln Glu Gly Arg Met Asn Val
    50                  55

<210> SEQ ID NO 28
<211> LENGTH: 55
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 28

Cys Tyr Pro Thr Val Thr Lys Gly Val Ser Ala Ala Cys Ser Lys Ser
1               5                   10                  15

Ser Phe Ile Trp Leu Thr Gly Ile His His Pro Pro Asn Ile Gly Asp
                20                  25                  30

Gln Arg Ala Leu Tyr His Glu Ile Ala Lys Arg Pro Lys Val Arg Asp
        35                  40                  45

Gln Glu Gly Arg Ile Asn Val
    50                  55

```
<210> SEQ ID NO 29
<211> LENGTH: 55
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 29

Cys Tyr Pro Thr Val Thr Lys Gly Val Ser Ala Ala Cys Pro Glu Ser
1               5                   10                  15

Ser Phe Ile Trp Leu Thr Gly Ile His His Pro Pro Asn Ile Gly Asp
            20                  25                  30

Gln Lys Thr Leu Tyr His Glu Ile Ala Lys Arg Pro Lys Val Arg Asp
        35                  40                  45

Gln Glu Gly Arg Ile Asn Val
    50                  55

<210> SEQ ID NO 30
<211> LENGTH: 97
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 30

Leu Gly Asn Pro Gly Thr Cys Tyr Pro Gly Tyr Lys Trp Asn His Thr
1               5                   10                  15

Val Thr Gly Val Thr Ala Ser Cys Ser His Ala Gly Lys Ser Ser Phe
            20                  25                  30

Tyr Arg Asn Leu Leu Trp Leu Thr Gly Lys Asn Gly Ser Tyr Pro Trp
        35                  40                  45

Gly Val His His Pro Ser Asn Ile Gly Asp Gln Gln Thr Leu Tyr Gln
    50                  55                  60

Thr Glu Asn Ala Phe Thr Pro Glu Ile Ala Lys Arg Pro Lys Val Arg
65                  70                  75                  80

Asp Gln Glu Gly Arg Met Asn Tyr Ala Asn Gly Asn Leu Ile Ala Pro
                85                  90                  95

Trp

<210> SEQ ID NO 31
<211> LENGTH: 97
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 31

Leu Gly Asn Pro Gly Thr Cys Tyr Pro Gly Tyr Lys Trp Asn His Asp
1               5                   10                  15

Val Thr Gly Val Ser Ala Ser Cys Ser His Asn Gly Ala Ser Ser Phe
            20                  25                  30

Tyr Arg Asn Leu Leu Trp Leu Thr Lys Lys Asn Asn Leu Tyr Pro Trp
        35                  40                  45

Gly Val His His Pro Ser Thr Ile Ala Asp Gln Gln Thr Leu Tyr His
    50                  55                  60
```

Thr Glu Asn Ala Phe Thr Pro Glu Ile Ala Ile Arg Pro Lys Val Arg
65                  70                  75                  80

Asp Gln Glu Gly Arg Ile Asn Tyr Ala Asn Gly Asn Leu Ile Ala Pro
                85                  90                  95

Trp

<210> SEQ ID NO 32
<211> LENGTH: 97
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 32

Leu Gly Asn Pro Gly Thr Cys Tyr Pro Gly Tyr Lys Trp Asn His Asp
1               5                   10                  15

Ser Asn Gly Val Thr Ala Ser Cys Pro His Ala Gly Ala Lys Ser Phe
            20                  25                  30

Tyr Arg Asn Leu Leu Trp Leu Val Lys Lys Gly Asn Ser Tyr Pro Trp
        35                  40                  45

Gly Val His His Pro Ser Thr Ser Ala Asp Gln Gln Ser Leu Tyr Gln
    50                  55                  60

Asn Ala Asn Ala Phe Thr Pro Glu Ile Ala Ile Arg Pro Lys Val Arg
65                  70                  75                  80

Asp Gln Glu Gly Arg Met Asn Tyr Ala Thr Gly Asn Leu Ile Ala Pro
                85                  90                  95

Trp

<210> SEQ ID NO 33
<211> LENGTH: 97
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 33

Leu Gly Asn Pro Gly Thr Cys Tyr Pro Gly Tyr Lys Trp Asn His Thr
1               5                   10                  15

Val Thr Gly Val Ser Ala Ser Cys Ser His Asn Gly Lys Ser Ser Phe
            20                  25                  30

Tyr Arg Asn Leu Leu Trp Leu Thr Gly Lys Asn Gly Leu Tyr Pro Trp
        35                  40                  45

Gly Val His His Pro Pro Asn Ile Gly Asp Gln Arg Ala Leu Tyr His
    50                  55                  60

Thr Glu Asn Ala Phe Thr Pro Glu Ile Ala Lys Arg Pro Lys Val Arg
65                  70                  75                  80

Asp Gln Glu Gly Arg Ile Asn Tyr Ala Asn Gly Asn Leu Ile Ala Pro
                85                  90                  95

Trp

<210> SEQ ID NO 34
<211> LENGTH: 97
<212> TYPE: PRT
<213> ORGANISM: Artificial Sequence
<220> FEATURE:

```
<221> NAME/KEY: source
<223> OTHER INFORMATION: /note="Description of Artificial Sequence:
      Synthetic polypeptide"

<400> SEQUENCE: 34
```

Leu Gly Asn Pro Gly Thr Cys Tyr Pro Gly Tyr Lys Trp Asn His Thr
1               5                   10                  15

Val Thr Gly Val Ser Ala Ser Cys Pro His Asn Gly Glu Ser Ser Phe
            20                  25                  30

Tyr Arg Asn Leu Leu Trp Leu Thr Gly Lys Asn Gly Leu Tyr Pro Trp
        35                  40                  45

Gly Val His His Pro Pro Asn Ile Gly Asp Gln Lys Thr Leu Tyr His
    50                  55                  60

Thr Glu Asn Ala Phe Thr Pro Glu Ile Ala Lys Arg Pro Lys Val Arg
65                  70                  75                  80

Asp Gln Glu Gly Arg Ile Asn Tyr Ala Asn Gly Asn Leu Ile Ala Pro
                85                  90                  95

Trp

```
<210> SEQ ID NO 35
<211> LENGTH: 98
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 35
```

Leu Gly Asn Pro Gly Thr Cys Tyr Pro Gly Asp Lys Trp Asn His Thr
1               5                   10                  15

Val Thr Lys Gly Val Thr Ala Ala Cys Ser His Ala Gly Lys Ser Ser
            20                  25                  30

Phe Tyr Lys Asn Leu Ile Trp Leu Thr Gly Lys Asn Gly Ser Tyr Pro
        35                  40                  45

Trp Gly Ile His His Pro Ser Asn Ile Gly Asp Gln Gln Thr Leu Tyr
    50                  55                  60

Gln Thr Glu Asp Thr Phe Lys Pro Glu Ile Ala Lys Arg Pro Lys Val
65                  70                  75                  80

Arg Asp Gln Glu Gly Arg Met Asn Tyr Ala Asn Gly Asn Leu Val Val
                85                  90                  95

Pro Arg

```
<210> SEQ ID NO 36
<211> LENGTH: 98
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 36
```

Leu Gly Asn Pro Gly Thr Cys Tyr Pro Gly Asp Lys Trp Asn His Asp
1               5                   10                  15

Val Thr Lys Gly Val Ser Ala Ala Cys Ser His Asn Gly Ala Ser Ser
            20                  25                  30

Phe Tyr Lys Asn Leu Ile Trp Leu Thr Lys Lys Asn Asn Leu Tyr Pro
        35                  40                  45

Trp Gly Ile His His Pro Ser Thr Ile Ala Asp Gln Gln Thr Leu Tyr
          50                  55                  60

His Thr Glu Asp Thr Phe Lys Pro Glu Ile Ala Ile Arg Pro Lys Val
 65                  70                  75                  80

Arg Asp Gln Glu Gly Arg Ile Asn Tyr Ala Asn Gly Asn Leu Val Val
                 85                  90                  95

Pro Arg

<210> SEQ ID NO 37
<211> LENGTH: 98
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 37

Leu Gly Asn Pro Gly Thr Cys Tyr Pro Gly Asp Lys Trp Asn His Asp
 1               5                  10                  15

Ser Asn Lys Gly Val Thr Ala Ala Cys Pro His Ala Gly Ala Lys Ser
                 20                  25                  30

Phe Tyr Lys Asn Leu Ile Trp Leu Val Lys Lys Gly Asn Ser Tyr Pro
             35                  40                  45

Trp Gly Ile His His Pro Ser Thr Ser Ala Asp Gln Gln Ser Leu Tyr
          50                  55                  60

Gln Asn Ala Asp Thr Phe Lys Pro Glu Ile Ala Ile Arg Pro Lys Val
 65                  70                  75                  80

Arg Asp Gln Glu Gly Arg Met Asn Tyr Ala Thr Gly Asn Leu Val Val
                 85                  90                  95

Pro Arg

<210> SEQ ID NO 38
<211> LENGTH: 98
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 38

Leu Gly Asn Pro Gly Thr Cys Tyr Pro Gly Asp Lys Trp Asn His Thr
 1               5                  10                  15

Val Thr Lys Gly Val Ser Ala Ala Cys Ser His Asn Gly Lys Ser Ser
                 20                  25                  30

Phe Tyr Lys Asn Leu Ile Trp Leu Thr Gly Lys Asn Gly Leu Tyr Pro
             35                  40                  45

Trp Gly Ile His His Pro Pro Asn Ile Gly Asp Gln Arg Ala Leu Tyr
          50                  55                  60

His Thr Glu Asp Thr Phe Lys Pro Glu Ile Ala Lys Arg Pro Lys Val
 65                  70                  75                  80

Arg Asp Gln Glu Gly Arg Ile Asn Tyr Ala Asn Gly Asn Leu Val Val
                 85                  90                  95

Pro Arg

<210> SEQ ID NO 39
<211> LENGTH: 98
<212> TYPE: PRT

```
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 39

Leu Gly Asn Pro Gly Thr Cys Tyr Pro Gly Asp Lys Trp Asn His Thr
1               5                   10                  15

Val Thr Lys Gly Val Ser Ala Ala Cys Pro His Asn Gly Glu Ser Ser
            20                  25                  30

Phe Tyr Lys Asn Leu Ile Trp Leu Thr Gly Lys Asn Gly Leu Tyr Pro
        35                  40                  45

Trp Gly Ile His His Pro Pro Asn Ile Gly Asp Gln Lys Thr Leu Tyr
    50                  55                  60

His Thr Glu Asp Thr Phe Lys Pro Glu Ile Ala Lys Arg Pro Lys Val
65                  70                  75                  80

Arg Asp Gln Glu Gly Arg Ile Asn Tyr Ala Asn Gly Asn Leu Val Val
                85                  90                  95

Pro Arg

<210> SEQ ID NO 40
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 40

Gly Lys Ala Pro Leu Lys Pro Glu Ser Leu Thr Ser Asp Gly Asp Pro
1               5                   10                  15

Val His

<210> SEQ ID NO 41
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 41

Gly Lys Ala Pro Leu Asn Pro Glu Leu Leu Lys Asn Glu Gly Trp Pro
1               5                   10                  15

Met Asp

<210> SEQ ID NO 42
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 42

Gly Lys Ala Pro Leu Asn Pro Glu Leu Leu Thr Asn Glu Gly Asn Pro
1               5                   10                  15

Met Asp
```

<210> SEQ ID NO 43
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 43

Gly Lys Ala Pro Leu Lys Pro Glu Thr Leu Thr Ser Asp Gly Asp Pro
1               5                   10                  15

Val His

<210> SEQ ID NO 44
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 44

Gly Lys Ala Pro Leu Asn Pro Glu Leu Leu Thr Asn Glu Gly Asn Pro
1               5                   10                  15

Met Gly

<210> SEQ ID NO 45
<211> LENGTH: 30
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 45

Tyr Asp Asn Lys Gly Val Thr Ala Lys Trp Val Lys Lys Gly Asn Ser
1               5                   10                  15

His Ser Thr Ser Ala Asp Gln Ser Leu Gln Ile Asp Gln Glu
            20                  25                  30

<210> SEQ ID NO 46
<211> LENGTH: 30
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 46

Tyr Asp Asn Lys Gly Val Thr Ala Lys Trp Val Lys Lys Gly Asn Ser
1               5                   10                  15

His Ser Thr Thr Ala Asp Gln Ser Leu Gln Ile Asp Gln Glu
            20                  25                  30

<210> SEQ ID NO 47
<211> LENGTH: 29
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

```
<400> SEQUENCE: 47

Tyr Thr Thr Gly Val Ser Ala Ser Trp Thr Gly Lys Asn Gly Leu His
1               5                   10                  15

Pro Asn Ile Gly Asp Arg Ala Leu His Lys Asp Gln Glu
            20                  25

<210> SEQ ID NO 48
<211> LENGTH: 30
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 48

Tyr Asp Asn Lys Gly Val Thr Ala Lys Trp Val Lys Lys Gly Asn Ser
1               5                   10                  15

His Ser Thr Ser Ala Asp Gln Ser Leu Gln Ile Glu Gln Glu
            20                  25                  30

<210> SEQ ID NO 49
<211> LENGTH: 29
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 49

Tyr Thr Thr Gly Val Ser Ala Ser Trp Thr Gly Lys Asn Gly Leu His
1               5                   10                  15

Pro Asn Ile Gly Asp Lys Ala Leu His Lys Asp Gln Glu
            20                  25

<210> SEQ ID NO 50
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 50

Ser His Asn Gly Glu Ser Arg Asp
1               5

<210> SEQ ID NO 51
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 51

Ser His Asn Gly Lys Ser Arg Asp
1               5

<210> SEQ ID NO 52
<211> LENGTH: 8
<212> TYPE: PRT
```

```
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 52

Pro His Ala Gly Ala Lys Arg Glu
1               5

<210> SEQ ID NO 53
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 53

Pro His Ala Gly Ala Lys Arg Gly
1               5

<210> SEQ ID NO 54
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 54

Pro His Ala Gly Ala Lys Arg Gly
1               5

<210> SEQ ID NO 55
<211> LENGTH: 23
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 55

Tyr His His Ser Leu Val Asp Gly Trp Leu Thr Gln Ala Ile Asp Ile
1               5                   10                  15

Thr Lys Val Asn Val Ile Thr
            20

<210> SEQ ID NO 56
<211> LENGTH: 23
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 56

Tyr His His Ser Leu Val Asp Gly Trp Gln Thr Gln Ala Ile Asn Ile
1               5                   10                  15

Thr Lys Val Asn Val Ile Thr
            20

<210> SEQ ID NO 57
```

-continued

```
<211> LENGTH: 23
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 57

Tyr His His Ser Leu Ile Asp Gly Trp Gln Thr Gln Ala Ile Asn Ile
1               5                   10                  15

Thr Lys Val Asn Val Ile Thr
            20

<210> SEQ ID NO 58
<211> LENGTH: 22
<212> TYPE: PRT
<213> ORGANISM: Influenza virus

<400> SEQUENCE: 58

Ile Leu Gly Asn Ser Glu Cys Glu Leu Leu Ile Ser Lys Glu Ser Trp
1               5                   10                  15

Ser Tyr Ile Val Glu Lys
            20

<210> SEQ ID NO 59
<211> LENGTH: 22
<212> TYPE: PRT
<213> ORGANISM: Influenza virus

<400> SEQUENCE: 59

Ile Leu Gly Asn Pro Glu Cys Asp Ser Leu Leu Pro Ala Ser Ser Trp
1               5                   10                  15

Ser Tyr Ile Val Glu Thr
            20

<210> SEQ ID NO 60
<211> LENGTH: 22
<212> TYPE: PRT
<213> ORGANISM: Influenza virus

<400> SEQUENCE: 60

Val Leu Gly Asn Pro Glu Cys Glu Ser Leu Leu Ser Asn Arg Ser Trp
1               5                   10                  15

Ser Tyr Ile Ala Glu Thr
            20

<210> SEQ ID NO 61
<211> LENGTH: 22
<212> TYPE: PRT
<213> ORGANISM: Influenza virus

<400> SEQUENCE: 61

Leu Leu Gly Asn Pro Glu Cys Asp Pro Leu Leu Pro Val Arg Ser Trp
1               5                   10                  15

Ser Tyr Ile Val Glu Thr
            20

<210> SEQ ID NO 62
<211> LENGTH: 22
<212> TYPE: PRT
<213> ORGANISM: Influenza virus

<400> SEQUENCE: 62
```

```
Leu Leu Gly Asn Pro Glu Cys Asp Ser Leu Pro Ala Ser Ser Trp
1               5                   10                  15

Ser Tyr Ile Val Glu Thr
            20
```

<210> SEQ ID NO 63
<211> LENGTH: 22
<212> TYPE: PRT
<213> ORGANISM: Influenza virus

<400> SEQUENCE: 63

```
Ile Leu Gly Asn Pro Glu Cys Glu Leu Leu Val Ser Lys Glu Ser Trp
1               5                   10                  15

Ser Tyr Ile Val Glu Lys
            20
```

<210> SEQ ID NO 64
<211> LENGTH: 22
<212> TYPE: PRT
<213> ORGANISM: Influenza virus

<400> SEQUENCE: 64

```
Val Leu Gly Asn Pro Glu Cys Glu Ser Leu Leu Ser Asn Arg Ser Trp
1               5                   10                  15

Ser Tyr Ile Ala Glu Thr
            20
```

<210> SEQ ID NO 65
<211> LENGTH: 22
<212> TYPE: PRT
<213> ORGANISM: Influenza virus

<400> SEQUENCE: 65

```
Leu Leu Gly Asn Pro Glu Cys Asp Pro Leu Leu Pro Ala Arg Ser Trp
1               5                   10                  15

Ser Tyr Ile Val Glu Thr
            20
```

<210> SEQ ID NO 66
<211> LENGTH: 22
<212> TYPE: PRT
<213> ORGANISM: Influenza virus

<400> SEQUENCE: 66

```
Leu Leu Gly Asn Pro Glu Cys Asp Ser Leu Leu Pro Ala Arg Ser Trp
1               5                   10                  15

Ser Tyr Ile Val Glu Thr
            20
```

<210> SEQ ID NO 67
<211> LENGTH: 22
<212> TYPE: PRT
<213> ORGANISM: Influenza virus

<400> SEQUENCE: 67

```
Leu Leu Gly Asn Pro Glu Cys Asp Pro Leu Leu Pro Val Arg Ser Trp
1               5                   10                  15

Ser Tyr Ile Val Glu Thr
            20
```

<210> SEQ ID NO 68

```
<211> LENGTH: 22
<212> TYPE: PRT
<213> ORGANISM: Influenza virus

<400> SEQUENCE: 68

Leu Leu Gly Asn Pro Glu Cys Asp Pro Leu Leu Pro Val Arg Ser Trp
1               5                   10                  15

Ser Tyr Ile Val Glu Thr
            20

<210> SEQ ID NO 69
<211> LENGTH: 22
<212> TYPE: PRT
<213> ORGANISM: Influenza virus

<400> SEQUENCE: 69

Leu Leu Gly Asn Pro Glu Cys Asp Pro Leu Leu Pro Val Arg Ser Trp
1               5                   10                  15

Ser Tyr Ile Val Glu Thr
            20

<210> SEQ ID NO 70
<211> LENGTH: 22
<212> TYPE: PRT
<213> ORGANISM: Influenza virus

<400> SEQUENCE: 70

Leu Leu Gly Asn Pro Glu Cys Asp Ser Leu Leu Pro Ala Arg Ser Trp
1               5                   10                  15

Ser Tyr Ile Val Glu Thr
            20

<210> SEQ ID NO 71
<211> LENGTH: 22
<212> TYPE: PRT
<213> ORGANISM: Influenza virus

<400> SEQUENCE: 71

Leu Leu Gly Asn Pro Glu Cys Asp Ser Leu Leu Pro Ala Arg Ser Trp
1               5                   10                  15

Ser Tyr Ile Val Glu Thr
            20

<210> SEQ ID NO 72
<211> LENGTH: 22
<212> TYPE: PRT
<213> ORGANISM: Influenza virus

<400> SEQUENCE: 72

Leu Leu Gly Asn Pro Glu Cys Glu Leu Leu Leu Thr Val Ser Ser Trp
1               5                   10                  15

Ser Tyr Ile Val Glu Thr
            20

<210> SEQ ID NO 73
<211> LENGTH: 22
<212> TYPE: PRT
<213> ORGANISM: Influenza virus

<400> SEQUENCE: 73

Leu Leu Gly Asn Pro Glu Cys Glu Leu Leu Leu Thr Val Ser Ser Trp
1               5                   10                  15
```

Ser Tyr Ile Val Glu Thr
            20

<210> SEQ ID NO 74
<211> LENGTH: 22
<212> TYPE: PRT
<213> ORGANISM: Influenza virus

<400> SEQUENCE: 74

Leu Leu Gly Asn Pro Glu Cys Glu Leu Leu Phe Thr Ala Ser Ser Trp
1               5                   10                  15

Ser Tyr Ile Val Glu Thr
            20

<210> SEQ ID NO 75
<211> LENGTH: 22
<212> TYPE: PRT
<213> ORGANISM: Influenza virus

<400> SEQUENCE: 75

Leu Leu Gly Asn Pro Glu Cys Glu Leu Leu Phe Thr Ala Ser Ser Trp
1               5                   10                  15

Ser Tyr Ile Val Glu Thr
            20

<210> SEQ ID NO 76
<211> LENGTH: 22
<212> TYPE: PRT
<213> ORGANISM: Influenza virus

<400> SEQUENCE: 76

Leu Leu Gly Asn Pro Glu Cys Glu Leu Leu Phe Thr Ala Ser Ser Trp
1               5                   10                  15

Ser Tyr Ile Val Glu Thr
            20

<210> SEQ ID NO 77
<211> LENGTH: 22
<212> TYPE: PRT
<213> ORGANISM: Influenza virus

<400> SEQUENCE: 77

Leu Leu Gly Asn Pro Glu Cys Glu Ser Leu Ser Thr Ala Ser Ser Trp
1               5                   10                  15

Ser Tyr Ile Val Glu Thr
            20

<210> SEQ ID NO 78
<211> LENGTH: 22
<212> TYPE: PRT
<213> ORGANISM: Influenza virus

<400> SEQUENCE: 78

Leu Leu Gly Asn Pro Glu Cys Glu Leu Leu Phe Thr Val Ser Ser Trp
1               5                   10                  15

Ser Tyr Ile Val Glu Thr
            20

<210> SEQ ID NO 79
<211> LENGTH: 6
<212> TYPE: PRT
<213> ORGANISM: Influenza virus

```
<400> SEQUENCE: 79

Leu Ile Ser Lys Glu Ser
1               5

<210> SEQ ID NO 80
<211> LENGTH: 6
<212> TYPE: PRT
<213> ORGANISM: Influenza virus

<400> SEQUENCE: 80

Leu Leu Pro Ala Ser Ser
1               5

<210> SEQ ID NO 81
<211> LENGTH: 6
<212> TYPE: PRT
<213> ORGANISM: Influenza virus

<400> SEQUENCE: 81

Leu Leu Ser Asn Arg Ser
1               5

<210> SEQ ID NO 82
<211> LENGTH: 6
<212> TYPE: PRT
<213> ORGANISM: Influenza virus

<400> SEQUENCE: 82

Leu Leu Pro Val Arg Ser
1               5

<210> SEQ ID NO 83
<211> LENGTH: 6
<212> TYPE: PRT
<213> ORGANISM: Influenza virus

<400> SEQUENCE: 83

Leu Leu Pro Ala Ser Ser
1               5

<210> SEQ ID NO 84
<211> LENGTH: 6
<212> TYPE: PRT
<213> ORGANISM: Influenza virus

<400> SEQUENCE: 84

Leu Val Ser Lys Glu Ser
1               5

<210> SEQ ID NO 85
<211> LENGTH: 6
<212> TYPE: PRT
<213> ORGANISM: Influenza virus

<400> SEQUENCE: 85

Leu Leu Ser Asn Arg Ser
1               5

<210> SEQ ID NO 86
<211> LENGTH: 6
<212> TYPE: PRT
<213> ORGANISM: Influenza virus

<400> SEQUENCE: 86
```

Leu Leu Pro Ala Arg Ser
1               5

<210> SEQ ID NO 87
<211> LENGTH: 6
<212> TYPE: PRT
<213> ORGANISM: Influenza virus

<400> SEQUENCE: 87

Leu Leu Pro Ala Arg Ser
1               5

<210> SEQ ID NO 88
<211> LENGTH: 6
<212> TYPE: PRT
<213> ORGANISM: Influenza virus

<400> SEQUENCE: 88

Leu Leu Pro Val Arg Ser
1               5

<210> SEQ ID NO 89
<211> LENGTH: 6
<212> TYPE: PRT
<213> ORGANISM: Influenza virus

<400> SEQUENCE: 89

Leu Leu Pro Val Arg Ser
1               5

<210> SEQ ID NO 90
<211> LENGTH: 6
<212> TYPE: PRT
<213> ORGANISM: Influenza virus

<400> SEQUENCE: 90

Leu Leu Pro Val Arg Ser
1               5

<210> SEQ ID NO 91
<211> LENGTH: 6
<212> TYPE: PRT
<213> ORGANISM: Influenza virus

<400> SEQUENCE: 91

Leu Leu Pro Ala Arg Ser
1               5

<210> SEQ ID NO 92
<211> LENGTH: 6
<212> TYPE: PRT
<213> ORGANISM: Influenza virus

<400> SEQUENCE: 92

Leu Leu Pro Ala Arg Ser
1               5

<210> SEQ ID NO 93
<211> LENGTH: 6
<212> TYPE: PRT
<213> ORGANISM: Influenza virus

<400> SEQUENCE: 93

Leu Leu Thr Val Ser Ser
1               5

```
<210> SEQ ID NO 94
<211> LENGTH: 6
<212> TYPE: PRT
<213> ORGANISM: Influenza virus

<400> SEQUENCE: 94

Leu Leu Thr Val Ser Ser
1               5

<210> SEQ ID NO 95
<211> LENGTH: 6
<212> TYPE: PRT
<213> ORGANISM: Influenza virus

<400> SEQUENCE: 95

Leu Phe Thr Ala Ser Ser
1               5

<210> SEQ ID NO 96
<211> LENGTH: 6
<212> TYPE: PRT
<213> ORGANISM: Influenza virus

<400> SEQUENCE: 96

Leu Phe Thr Ala Ser Ser
1               5

<210> SEQ ID NO 97
<211> LENGTH: 6
<212> TYPE: PRT
<213> ORGANISM: Influenza virus

<400> SEQUENCE: 97

Leu Phe Thr Ala Ser Ser
1               5

<210> SEQ ID NO 98
<211> LENGTH: 6
<212> TYPE: PRT
<213> ORGANISM: Influenza virus

<400> SEQUENCE: 98

Leu Ser Thr Ala Ser Ser
1               5

<210> SEQ ID NO 99
<211> LENGTH: 6
<212> TYPE: PRT
<213> ORGANISM: Influenza virus

<400> SEQUENCE: 99

Leu Phe Thr Val Ser Ser
1               5

<210> SEQ ID NO 100
<211> LENGTH: 6
<212> TYPE: PRT
<213> ORGANISM: Influenza virus

<400> SEQUENCE: 100

Leu Ile Ser Lys Glu Ser
1               5
```

```
<210> SEQ ID NO 101
<211> LENGTH: 6
<212> TYPE: PRT
<213> ORGANISM: Influenza virus

<400> SEQUENCE: 101

Leu Leu Pro Ala Ser Ser
1               5

<210> SEQ ID NO 102
<211> LENGTH: 6
<212> TYPE: PRT
<213> ORGANISM: Influenza virus

<400> SEQUENCE: 102

Leu Leu Ser Asn Arg Ser
1               5

<210> SEQ ID NO 103
<211> LENGTH: 6
<212> TYPE: PRT
<213> ORGANISM: Influenza virus

<400> SEQUENCE: 103

Leu Leu Pro Val Arg Ser
1               5

<210> SEQ ID NO 104
<211> LENGTH: 6
<212> TYPE: PRT
<213> ORGANISM: Influenza virus

<400> SEQUENCE: 104

Leu Val Ser Lys Glu Ser
1               5

<210> SEQ ID NO 105
<211> LENGTH: 6
<212> TYPE: PRT
<213> ORGANISM: Influenza virus

<400> SEQUENCE: 105

Leu Leu Pro Ala Arg Ser
1               5

<210> SEQ ID NO 106
<211> LENGTH: 6
<212> TYPE: PRT
<213> ORGANISM: Influenza virus

<400> SEQUENCE: 106

Leu Leu Thr Val Ser Ser
1               5

<210> SEQ ID NO 107
<211> LENGTH: 6
<212> TYPE: PRT
<213> ORGANISM: Influenza virus

<400> SEQUENCE: 107

Leu Phe Thr Ala Ser Ser
1               5

<210> SEQ ID NO 108
<211> LENGTH: 6
```

```
<212> TYPE: PRT
<213> ORGANISM: Influenza virus

<400> SEQUENCE: 108

Leu Ser Thr Ala Ser Ser
1               5

<210> SEQ ID NO 109
<211> LENGTH: 6
<212> TYPE: PRT
<213> ORGANISM: Influenza virus

<400> SEQUENCE: 109

Leu Phe Thr Val Ser Ser
1               5

<210> SEQ ID NO 110
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 110

Leu Ile Ser Lys Glu Ser
1               5

<210> SEQ ID NO 111
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 111

Leu Leu Pro Val Arg Ser
1               5

<210> SEQ ID NO 112
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 112

Leu Leu Thr Val Ser Ser
1               5

<210> SEQ ID NO 113
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 113

Leu Leu Pro Ala Ser Ser
1               5
```

```
<210> SEQ ID NO 114
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 114

Leu Val Ser Lys Glu Ser
1               5

<210> SEQ ID NO 115
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 115

Leu Phe Thr Ala Ser Ser
1               5

<210> SEQ ID NO 116
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 116

Leu Leu Ser Asn Arg Ser
1               5

<210> SEQ ID NO 117
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 117

Leu Leu Pro Ala Arg Ser
1               5

<210> SEQ ID NO 118
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 118

Leu Ser Thr Ala Ser Ser
1               5

<210> SEQ ID NO 119
<211> LENGTH: 6
<212> TYPE: PRT
```

```
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 119

Leu Leu Pro Val Arg Ser
1               5

<210> SEQ ID NO 120
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 120

Leu Leu Thr Val Ser Ser
1               5

<210> SEQ ID NO 121
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 121

Leu Phe Thr Val Ser Ser
1               5

<210> SEQ ID NO 122
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 122

Leu Val Ser Lys Glu Ser
1               5

<210> SEQ ID NO 123
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 123

Leu Phe Thr Ala Ser Ser
1               5

<210> SEQ ID NO 124
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
```

Synthetic peptide"

<400> SEQUENCE: 124

Leu Leu Pro Val Arg Ser
1               5

<210> SEQ ID NO 125
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 125

Val Asn Asn Lys Glu Ser Ser Asn Glu Pro Gly
1               5                   10

<210> SEQ ID NO 126
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 126

Ser His Ala Arg Lys Ser Arg Asn
1               5

<210> SEQ ID NO 127
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 127

Leu Leu Pro Ala Arg Ser Trp Ser
1               5

<210> SEQ ID NO 128
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 128

Leu Leu Pro Ala Arg Ser Trp Ser
1               5

<210> SEQ ID NO 129
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 129

Glu Ile Phe Pro
1

<210> SEQ ID NO 130
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 130

Ser Trp Pro Asn
1

<210> SEQ ID NO 131
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 131

Glu Thr Asn
1

<210> SEQ ID NO 132
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 132

Ser His Ala Arg Lys Ser
1               5

<210> SEQ ID NO 133
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 133

Ile Asn Asp Lys Gly Thr Ser Arg Glu Pro Gly
1               5                   10

<210> SEQ ID NO 134
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 134

Pro His Ala Gly Ala Lys Arg Asp
1               5

```
<210> SEQ ID NO 135
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 135

Leu Ser Thr Ala Ser Ser Trp Ser
1               5

<210> SEQ ID NO 136
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 136

Leu Ser Thr Ala Ser Ser Trp Ser
1               5

<210> SEQ ID NO 137
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 137

Glu Ile Phe Pro
1

<210> SEQ ID NO 138
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 138

Ser Trp Pro Asn
1

<210> SEQ ID NO 139
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 139

Thr Val Thr
1

<210> SEQ ID NO 140
<211> LENGTH: 6
<212> TYPE: PRT
<213> ORGANISM: Artificial Sequence
```

```
<220> FEATURE:
<221> NAME/KEY: source
<223> OTHER INFORMATION: /note="Description of Artificial Sequence:
      Synthetic peptide"

<400> SEQUENCE: 140

Pro His Ala Gly Ala Lys
1               5

<210> SEQ ID NO 141
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 141

Val Asn Asn Lys Glu Ser Ser Asn Glu Pro Gly
1               5                   10

<210> SEQ ID NO 142
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 142

Ser His Ala Arg Lys Ser Arg Asn
1               5

<210> SEQ ID NO 143
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 143

Leu Leu Pro Ala Arg Ser Trp Ser
1               5

<210> SEQ ID NO 144
<211> LENGTH: 72
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 144

Leu Leu Pro Ala Arg Ser Trp Ser Tyr Ile Val Glu Thr Pro Asn Pro
1               5                   10                  15

Glu Asn Gly Thr Cys Tyr Pro Gly Tyr Phe Ala Asp Tyr Glu Glu Leu
            20                  25                  30

Arg Glu Gln Leu Ser Ser Val Ser Ser Phe Glu Arg Phe Glu Ile Phe
        35                  40                  45

Pro Lys Glu Ser Ser Trp Pro Asn His Glu Thr Asn Gly Val Ser Ala
    50                  55                  60
```

Ser Cys Ser His Ala Arg Lys Ser
65                  70

<210> SEQ ID NO 145
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 145

Ile Asn Asp Lys Gly Thr Ser Arg Glu Pro Gly
1               5                   10

<210> SEQ ID NO 146
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 146

Pro His Ala Gly Ala Lys Arg Asp
1               5

<210> SEQ ID NO 147
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 147

Leu Ser Thr Ala Ser Ser Trp Ser
1               5

<210> SEQ ID NO 148
<211> LENGTH: 72
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 148

Leu Ser Thr Ala Ser Ser Trp Ser Tyr Ile Val Glu Thr Pro Asn Pro
1               5                   10                  15

Glu Asn Gly Thr Cys Tyr Pro Gly Tyr Phe Ala Asp Tyr Glu Glu Leu
            20                  25                  30

Arg Glu Gln Leu Ser Ser Val Ser Ser Phe Glu Arg Phe Glu Ile Phe
        35                  40                  45

Pro Lys Glu Ser Ser Trp Pro Asn His Thr Val Thr Gly Val Ser Ala
    50                  55                  60

Ser Cys Pro His Ala Gly Ala Lys
65                  70

<210> SEQ ID NO 149
<211> LENGTH: 4
<212> TYPE: PRT

<213> ORGANISM: Influenza virus

<400> SEQUENCE: 149

Val Asp Gly Trp
1

<210> SEQ ID NO 150
<211> LENGTH: 15
<212> TYPE: PRT
<213> ORGANISM: Influenza virus

<400> SEQUENCE: 150

Ser Ser Pro Asn Lys Gly Ser Ser Tyr Pro Lys Ser Lys Ser Val
1 5 10 15

<210> SEQ ID NO 151
<211> LENGTH: 8
<212> TYPE: PRT
<213> ORGANISM: Influenza virus

<400> SEQUENCE: 151

Ile Ile Pro Lys Ser Ser Trp Ser
1 5

<210> SEQ ID NO 152
<211> LENGTH: 7
<212> TYPE: PRT
<213> ORGANISM: Influenza virus

<400> SEQUENCE: 152

Ile Ile Trp Glu Ser Lys Asn
1 5

<210> SEQ ID NO 153
<211> LENGTH: 8
<212> TYPE: PRT
<213> ORGANISM: Influenza virus

<400> SEQUENCE: 153

Gln Ile Ile Pro Glu Ala Ser Leu
1 5

<210> SEQ ID NO 154
<211> LENGTH: 7
<212> TYPE: PRT
<213> ORGANISM: Influenza virus

<400> SEQUENCE: 154

Ser Trp Ser Tyr Asn Asn Thr
1 5

<210> SEQ ID NO 155
<211> LENGTH: 9
<212> TYPE: PRT
<213> ORGANISM: Influenza virus

<400> SEQUENCE: 155

Asn Phe Asp Lys Leu Tyr Ile Trp Gly
1 5

<210> SEQ ID NO 156
<211> LENGTH: 13
<212> TYPE: PRT
<213> ORGANISM: Influenza virus

<400> SEQUENCE: 156

Pro Asn Lys Lys Gly Asn Ser Pro Lys Leu Ser Lys Ser
1               5                   10

<210> SEQ ID NO 157
<211> LENGTH: 5
<212> TYPE: PRT
<213> ORGANISM: Influenza virus

<400> SEQUENCE: 157

Val Asn Asn Lys Glu
1               5

<210> SEQ ID NO 158
<211> LENGTH: 66
<212> TYPE: PRT
<213> ORGANISM: Influenza virus

<400> SEQUENCE: 158

Phe Glu Ile Phe Pro Lys Thr Ser Ser Trp Pro Asn His Glu Thr Thr
1               5                   10                  15

Lys Gly Val Thr Ala Ala Cys Ser Tyr Ala Gly Ala Ser Ser Phe Tyr
            20                  25                  30

Arg Asn Leu Leu Trp Leu Thr Lys Lys Gly Ser Ser Tyr Pro Lys Leu
        35                  40                  45

Ser Lys Ser Tyr Val Asn Asn Lys Gly Lys Glu Val Leu Val Leu Trp
    50                  55                  60

Gly Val
65

<210> SEQ ID NO 159
<211> LENGTH: 62
<212> TYPE: PRT
<213> ORGANISM: Influenza virus

<400> SEQUENCE: 159

Asn Asn Glu Ser Phe Asn Trp Thr Gly Val Thr Gln Asn Gly Thr Ser
1               5                   10                  15

Ser Ala Cys Lys Arg Arg Ser Asn Asn Ser Phe Phe Ser Arg Leu Asn
20 25 30

Trp Leu Thr Gln Leu Lys Phe Lys Tyr Pro Ala Leu Lys Val Thr Met
35 40 45

Pro Asn Asn Glu Lys Phe Asp Lys Leu Tyr Ile Trp Gly Val
50 55 60

<210> SEQ ID NO 160
<211> LENGTH: 43
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 160

Glu Ile Phe Pro Ser Trp Pro Asn Asn Thr Asn Ser His Ala Gly Lys
1 5 10 15

Ser Glu Lys Glu Gly Ser Pro Lys Leu Lys Asn Ser Tyr Val Asn Asn
20 25 30

Lys Gly Lys Glu Val Leu Val Leu Trp Gly Ser
35 40

-continued

<210> SEQ ID NO 161
<211> LENGTH: 43
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 161

Glu Ile Phe Pro Ser Trp Pro Asn Asp Ser Asn Pro His Ala Gly Ala
1               5                   10                  15

Lys Lys Lys Gly Asn Ser Pro Lys Leu Ser Asn Ser Tyr Ile Asn Asp
            20                  25                  30

Lys Gly Lys Glu Val Leu Val Leu Trp Gly Thr
        35                  40

<210> SEQ ID NO 162
<211> LENGTH: 43
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 162

Glu Ile Phe Pro Ser Trp Pro Asn Thr Val Thr Ser His Asn Gly Lys
1               5                   10                  15

Ser Gly Lys Asn Gly Leu Pro Asn Leu Ser Lys Ser Tyr Ala Asn Asn
            20                  25                  30

Lys Glu Lys Glu Val Leu Val Leu Trp Gly Asn
        35                  40

<210> SEQ ID NO 163
<211> LENGTH: 43
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 163

Glu Ile Phe Pro Ser Trp Pro Lys Asp Pro Asn Ser His Asn Gly Glu
1               5                   10                  15

Ser Glu Lys Asn Gly Ser Pro Asn Leu Ser Lys Ser Tyr Ile Asn Asp
            20                  25                  30

Lys Gly Lys Lys Val Leu Val Leu Trp Gly Asn
        35                  40

<210> SEQ ID NO 164
<211> LENGTH: 43
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 164

Glu Ile Phe Pro Ser Trp Pro Asn Asn Val Thr Pro His Ala Gly Ala
1               5                   10                  15

Lys Glu Lys Asn Gly Leu Pro Asn Leu Ser Lys Ser Tyr Val Asn Asn
            20                  25                  30

Lys Glu Lys Glu Ile Leu Val Leu Trp Gly Asn
        35                  40

<210> SEQ ID NO 165
<211> LENGTH: 43
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 165

Glu Ile Phe Pro Ser Trp Pro Asn Thr Thr Arg Ser His Lys Gly Lys
1               5                   10                  15

Ser Gly Lys Asn Gly Leu Pro Asn Leu Ser Met Ser Tyr Val Asn Asn
            20                  25                  30

Lys Glu Arg Glu Val Leu Val Leu Trp Gly Asn
        35                  40

<210> SEQ ID NO 166
<211> LENGTH: 73
<212> TYPE: PRT
<213> ORGANISM: Influenza virus

<400> SEQUENCE: 166

Phe Glu Arg Phe Glu Ile Phe Pro Lys Glu Ser Ser Trp Pro Asn His
1               5                   10                  15

Asn Thr Asn Gly Val Ser Ala Ser Cys Ser His Ala Gly Lys Ser Ser
            20                  25                  30

Phe Tyr Arg Asn Leu Leu Trp Leu Thr Glu Lys Glu Gly Ser Tyr Pro
        35                  40                  45

Lys Leu Lys Asn Ser Tyr Val Asn Asn Lys Gly Lys Glu Val Leu Val
    50                  55                  60

Leu Trp Gly Val His His Pro Pro Ser
65                  70

<210> SEQ ID NO 167
<211> LENGTH: 73
<212> TYPE: PRT
<213> ORGANISM: Influenza virus

<400> SEQUENCE: 167

Phe

```
<400> SEQUENCE: 168

Phe Glu Arg Phe Glu Ile Phe Pro Lys Glu Ser Ser Trp Pro Asn His
1               5                   10                  15

Thr Val Thr Gly Val Ser Ala Ser Cys Ser His Asn Gly Lys Ser Ser
            20                  25                  30

Phe Tyr Arg Asn Leu Leu Trp Leu Thr Gly Lys Asn Gly Leu Tyr Pro
        35                  40                  45

Asn Leu Ser Lys Ser Tyr Ala Asn Asn Lys Lys Glu Val Leu Val
    50                  55                  60

Leu Trp Gly Val His His Pro Pro Asn
65                  70

<210> SEQ ID NO 169
<211> LENGTH: 73
<212> TYPE: PRT
<213> ORGANISM: Influenza virus

<400> SEQUENCE: 169

Phe Glu Arg Phe Glu Ile Phe Pro Lys Glu Ser Ser Trp Pro Lys His
1               5                   10                  15

Asp Pro Asn Gly Val Ser Ala Ser Cys Ser His Asn Gly Glu Ser Ser
            20                  25                  30

Phe Tyr Arg Asn Leu Leu Trp Leu Thr Glu Lys Asn Gly Ser Tyr Pro
        35                  40                  45

Asn Leu Ser Lys Ser Tyr Ile Asn Asp Lys Gly Lys Val Leu Val
    50                  55                  60

Leu Trp Gly Val His His Pro Pro Asn
65                  70

<210> SEQ ID NO 170
<211> LENGTH: 73
<212> TYPE: PRT
<213> ORGANISM: Influenza virus

<400> SEQUENCE: 170

Phe Glu Arg Phe Glu Ile Phe Pro Lys Glu Ser Ser Trp Pro Asn His
1               5                   10                  15

Asn Val Thr Gly Val Ser Ala Ser Cys Pro His Ala Gly Ala Lys Ser
            20                  25                  30

Phe Tyr Arg Asn Leu Leu Trp Leu Thr Glu Lys Asn Gly Leu Tyr Pro
        35                  40                  45

Asn Leu Ser Lys Ser Tyr Val Asn Asn Lys Glu Lys Glu Ile Leu Val
    50                  55                  60

Leu Trp Gly Val His His Pro Pro Asn
65                  70

<210> SEQ ID NO 171
<211> LENGTH: 73
<212> TYPE: PRT
<213> ORGANISM: Influenza virus

<400> SEQUENCE: 171

Phe Glu Arg Phe Glu Ile Phe Pro Lys Glu Ser Ser Trp Pro Asn His
1               5                   10                  15

Thr Thr Arg Gly Val Ser Ala Ser Cys Ser His Lys Gly Lys Ser Ser
            20                  25                  30

Phe Tyr Arg Asn Leu Leu Trp Leu Thr Gly Lys Asn Gly Leu Tyr Pro
        35                  40                  45
```

```
Asn Leu Ser Met Ser Tyr Val Asn Asn Lys Glu Arg Glu Val Leu Val
    50                  55                  60

Leu Trp Gly Val His His Pro Pro Asn
65                  70

<210> SEQ ID NO 172
<211> LENGTH: 8
<212> TYPE: PRT
<213> ORGANISM: Influenza virus

<400> SEQUENCE: 172

Cys Asn Thr Lys Cys Gln Thr Pro
1               5

<210> SEQ ID NO 173
<211> LENGTH: 13
<212> TYPE: PRT
<213> ORGANISM: Influenza virus

<400> SEQUENCE: 173

Ser Ser Arg Ile Ser Ile Tyr Trp Thr Ile Val Lys Pro
1               5                   10
```